(12) United States Patent
Jo et al.

(10) Patent No.: US 7,196,081 B2
(45) Date of Patent: *Mar. 27, 2007

(54) COMPOUNDS WITH HYDROXYCARBONYL-HALOGENOALKYL SIDE CHAINS

(75) Inventors: JaeChon Jo, Seoul (KR); HeeAn Kwon, Kyonggi-do (KR); HyunSuk Lim, Kyonggi-do (KR); JaeYoung Choi, Seoul (KR); Kazumi Morikawa, Shizuoka (JP); Yoshitake Kanbe, Shizuoka (JP); Masahiro Nishimoto, Shizuoka (JP); MyungHwa Kim, Shizuoka (JP); Yoshikazu Nishimura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 415 days.

This patent is subject to a terminal disclaimer.

(21) Appl. No.: 10/281,990

(22) Filed: Oct. 29, 2002

(65) Prior Publication Data
US 2003/0130347 A1    Jul. 10, 2003

Related U.S. Application Data

(62) Division of application No. 10/149,752, filed as application No. PCT/JP00/08810 on Dec. 13, 2000, now Pat. No. 6,737,417.

(30) Foreign Application Priority Data

| Dec. 13, 1999 | (JP) | ................................. 11-353640 |
| Apr. 3, 2000 | (JP) | ............................. 2000-100567 |
| Jun. 21, 2000 | (JP) | ............................. 2000-186684 |
| Jul. 31, 2000 | (JP) | ............................. 2000-232091 |
| Nov. 24, 2000 | (JP) | ............................. 2000-357793 |

(51) Int. Cl.
| C07D 265/36 | (2006.01) |
| C07D 303/18 | (2006.01) |
| C07D 209/12 | (2006.01) |
| C07D 333/56 | (2006.01) |
| A61K 31/20 | (2006.01) |
| A61K 31/538 | (2006.01) |
| A61P 35/00 | (2006.01) |
| A61K 31/565 | (2006.01) |
| A61K 31/381 | (2006.01) |
| C07D 311/60 | (2006.01) |

(52) U.S. Cl. ................ 514/230.5; 514/412; 514/443; 514/456; 514/520; 514/570; 544/105; 548/452; 549/23; 549/49

(58) Field of Classification Search ............... 562/466; 560/56, 65; 514/520, 570, 412, 443, 456; 544/105; 548/452; 549/23, 49
See application file for complete search history.

(56) References Cited

U.S. PATENT DOCUMENTS

| 6,552,068 | B1 * | 4/2003 | Kanbe et al. | ............... 514/432 |
| 6,552,069 | B1 * | 4/2003 | Jo et al. | ..................... 514/432 |
| 6,555,571 | B2 * | 4/2003 | Jo et al. | ..................... 514/432 |
| 6,610,733 | B2 * | 8/2003 | Park et al. | .................. 514/434 |
| 6,737,417 | B2 * | 5/2004 | Jo et al. | ..................... 514/177 |

FOREIGN PATENT DOCUMENTS

| EP | 0 367 576 A2 | 5/1990 |
| EP | 0 670 162 A1 | 9/1995 |
| EP | 1 219 631 A1 | 7/2002 |
| FR | 2765216 | * 12/1998 |
| WO | WO 99/65893 A1 | 12/1999 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*

* cited by examiner

*Primary Examiner*—Venkataraman Balasubramanian
(74) *Attorney, Agent, or Firm*—Browdy and Neimark, PLLC

(57) ABSTRACT

The present invention provides a compound consisting of a moiety and a group chemically bonded to said moiety, wherein said moiety contains a compound having low activity following oral administration or its parent scaffold and said group has the following general formula (1):

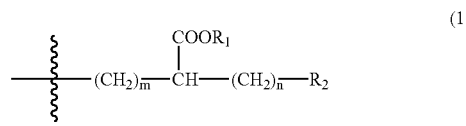

in which
  $R_1$ represents a hydrogen atom, etc.,
  $R_2$ represents a $C_1$–$C_7$ halogenoalkyl group, etc.,
  m represents an integer of 2 to 14, and
  n represents an integer of 2 to 7,
or enantiomers of the compound, or hydrates or pharmaceutically acceptable salts of the compound or enantiomers thereof. The above compound is advantageous in pharmaceutical use because the group of general formula (1) allows compounds such as anti-estrogenic ones to show a significantly increased activity following oral administration when attached to the parent scaffolds of the compounds.

14 Claims, No Drawings

COMPOUNDS WITH HYDROXYCARBONYL-HALOGENOALKYL SIDE CHAINS

This is a division of parent application Ser. No. 10/149,752, filed Jun. 13, 2002, now U.S. Pat. No. 6,737,417 which is the national stage under 35 U.S.C. §371 of international application PCT/JP00/08810.

TECHNICAL FIELD

The present invention relates to hydroxycarbonyl-halogenoalkyl derivatives designed to significantly increase oral activity of compounds having low activity following oral administration, compounds having anti-tumor activity, compounds having estrogenic activity or compounds having anti-estrogenic activity.

BACKGROUND ART

In treating diseases caused by abnormal tissue growth that is dependent upon a certain sexual steroidal hormone such as estrogen, it is highly important to significantly inhibit, more preferably completely eliminate, the effect induced by the hormone. For this purpose, it is desirable to reduce the level of hormone capable of acting on the steroidal hormone receptor site. For instance, anti-estrogenic agents are commonly administered for alternative or combination therapy to limit the production of estrogen to the amount less than required to activate the receptor site. However, such conventional technique for blocking estrogen production could not sufficiently inhibit the effect induced through the estrogen receptor. Practically, even when estrogen is completely absent, some of the receptors may be activated. It was therefore considered that estrogen antagonists could provide better therapeutic effect in comparison to the technique for blocking only the production of sexual steroidal hormone. Thus, numerous estrogen antagonists have been developed. For example, many patent publications including U.S. Pat. Nos. 4,760,061, 4,732,912, 4,904,661, 5,395,842 and WO 96/22092 disclose various anti-estrogenic compounds. Sometimes, however, prior art antagonists may themselves act as agonists, and therefore activate rather than block the receptor. For example, Tamoxifen has been most widely used as an anti-estrogenic agent. However, this agent has a disadvantage that it exhibits estrogenic activity in some organs (see, M. Harper and A. Walpole, J. Reprod. Fertile., 1967, 13, 101).

As another non-steroidal anti-estrogenic compound, WO 93/10741 discloses a benzopyran derivative having an aminoethoxyphenyl substituent(s) (Endorecherche), the typical compound of which is EM-343 having the following structure:

EM-343

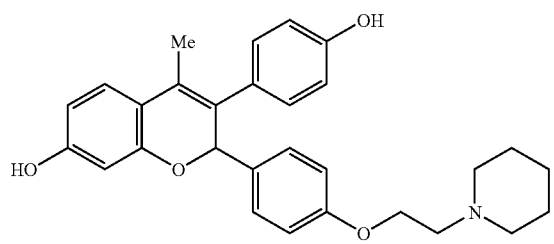

Said compound also has the agonistic effect. It is therefore required to develop an anti-estrogenic compound which is substantially or completely free of agonistic effect and which can effectively block the estrogen receptor.

In addition, it has been known that 7α-substituted derivatives of estradiol, for example, 7α-$(CH_2)_{10}$CONMeBu derivatives, are steroidal anti-estrogenic agents without agonistic effect (see, EP-A 0138504, U.S. Pat. No. 4,659,516). Further, an estradiol derivative having a 7α-$(CH_2)_9$SOC$_5$H$_6$F$_5$ substituent has also been disclosed as a 7α-substituted derivative of estradiol (see, Wakeling et al., Cancer Res., 1991, 51, 3867).

Non-steroidal anti-estrogenic agents without agonistic effect have been first reported by Wakeling et al. in 1987 (see, A. Wakeling and Bowler, J. Endocrinol., 1987, 112, R7). Meanwhile, U.S. Pat. No. 4,904,661 discloses phenol derivatives having anti-estrogenic activity. These phenol derivatives generally have a naphthalene scaffold and include, typically, the following compounds:

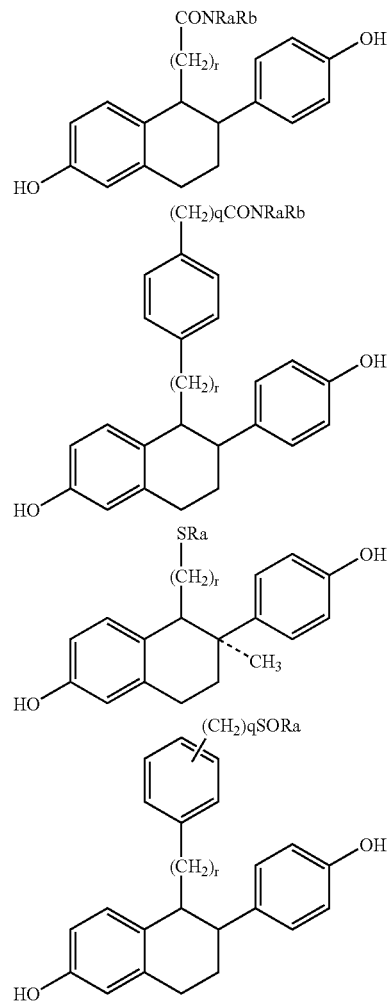

Some chroman and thiochroman derivatives have been reported as anti-estrogenic compounds having no agonistic effect (WO 98/25916). Although the existing anti-estrogenic compounds having no agonistic effect show a substantial therapeutic effect when administered via intravenous or subcutaneous injection, they show a highly reduced therapeutic effect when administered orally, due to their low bioavailability by oral route. Therefore, for convenience's sake in the case of administration, it is desired to develop anti-estrogenic compounds which show a sufficient effect when administered orally and at the same time have no agonistic effect. Also, it is generally desired to develop agents which show a sufficient effect when administered orally.

DISCLOSURE OF THE INVENTION

The object of the present invention is to provide hydroxycarbonyl-halogenoalkyl derivatives designed to significantly increase oral activity of compounds having low activity following oral administration, compounds having anti-tumor activity, compounds having estrogenic activity or compounds having anti-estrogenic activity by enhancing their absorption from the intestinal tract and/or improving their stability against metabolism.

Our research efforts were directed to achieving the above object, and we have found that a side chain of general formula (1) allowed estrogenic compounds to show a significantly increased activity by oral route when attached to the parent scaffolds of the compounds. The present invention has been accomplished on the basis of this finding.

Namely, the present invention provides a compound consisting of a moiety and a group chemically bonded to said moiety, wherein said moiety contains a compound having low activity following oral administration or its parent scaffold and said group has the following general formula (1):

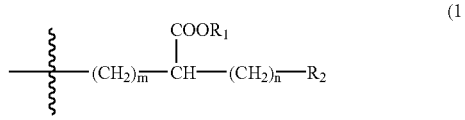
(1)

in which
$R_1$ represents a hydrogen atom or a salt-forming metal,
$R_2$ represents a linear or branched $C_1$–$C_7$ halogenoalkyl group,
m represents an integer of 2 to 14, and
n represents an integer of 2 to 7, or enantiomers of the first-mentioned compound, or hydrates or pharmaceutically acceptable salts of the compound or enantiomers thereof.

The present invention also provides a compound consisting of a moiety and a group chemically bonded to said moiety, wherein said moiety contains a compound having anti-tumor activity or its parent scaffold and said group has the following general formula (1):

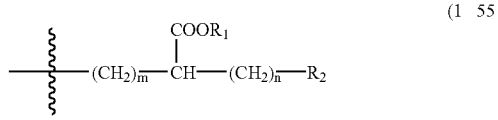
(1)

in which
$R_1$ represents a hydrogen atom or a salt-forming metal,
$R_2$ represents a linear or branched $C_1$–$C_7$ halogenoalkyl group,
m represents an integer of 2 to 14, and
n represents an integer of 2 to 7, or enantiomers of the first-mentioned compound, or hydrates or pharmaceutically acceptable salts of the first-mentioned compound or enantiomers thereof.

The present invention further provides a compound consisting of a moiety and a group chemically bonded to a moiety, wherein said moiety contains a compound having estrogenic activity or its parent scaffold or a compound having anti-estrogenic activity or its parent scaffold and said group has the following general formula (1):

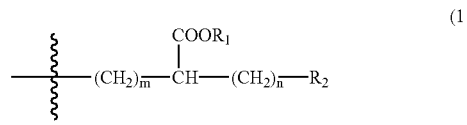
(1)

in which
$R_1$ represents a hydrogen atom or a salt-forming metal,
$R_2$ represents a linear or branched $C_1$–$C_7$ halogenoalkyl group,
m represents an integer of 2 to 14, and
n represents an integer of 2 to 7, or enantiomers of the first-mentioned compound, or hydrates or pharmaceutically acceptable salts of the first-mentioned compound or enantiomers.

The present invention even further provides a compound having the following general formula (2):

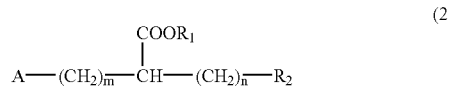
(2)

in which
$R_1$ represents a hydrogen atom or a salt-forming metal,
$R_2$ represents a linear or branched $C_1$–$C_7$ halogenoalkyl group,
m represents an integer of 2 to 14,
n represents an integer of 2 to 7, and
A represents a group selected from the following formulae (3) to (8) and (10) to (26):

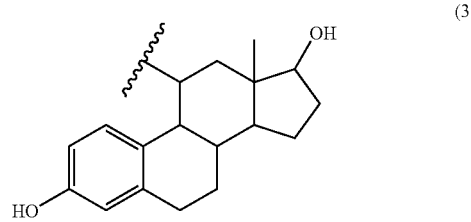
(3)

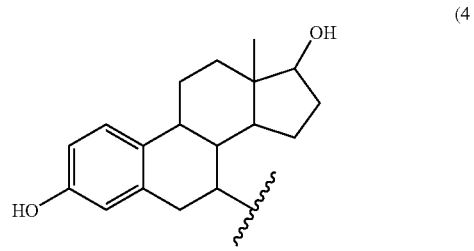
(4)

-continued
(5)
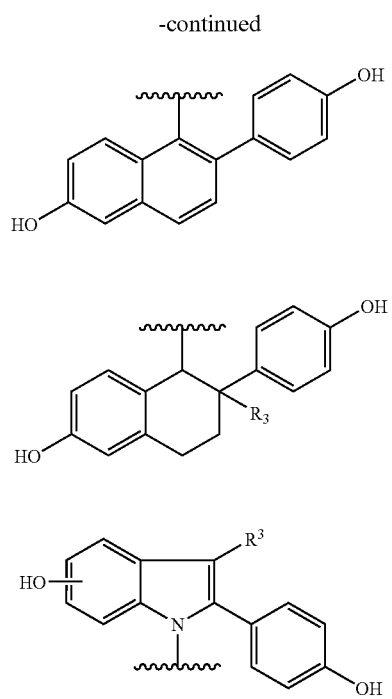
(6)
(7)
(8)
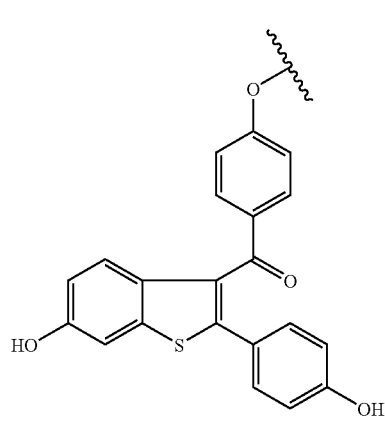
(10)
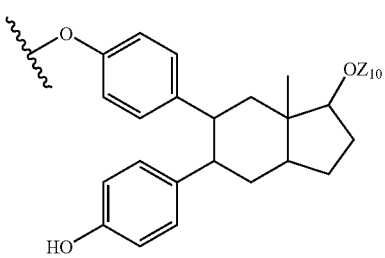
(11)
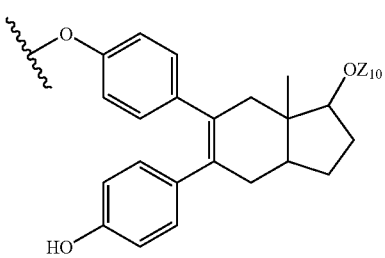
-continued
(12)
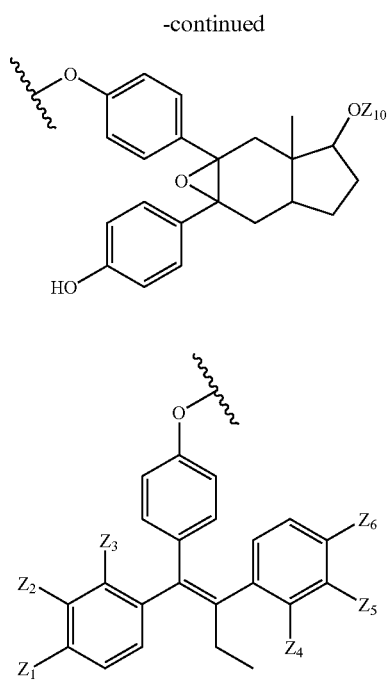
(13)
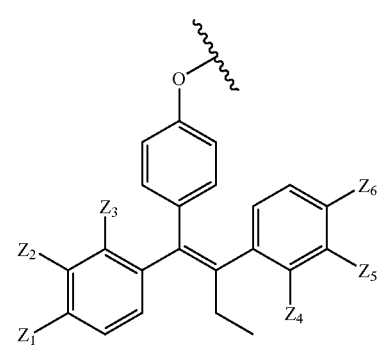
(14)
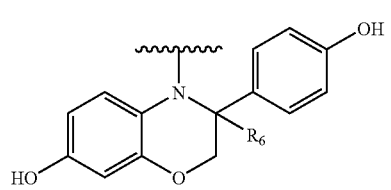
(15)
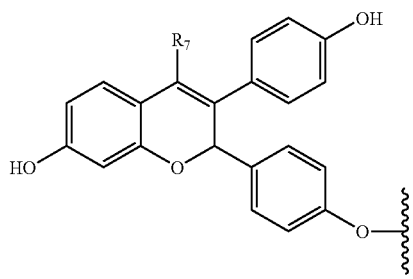
(16)
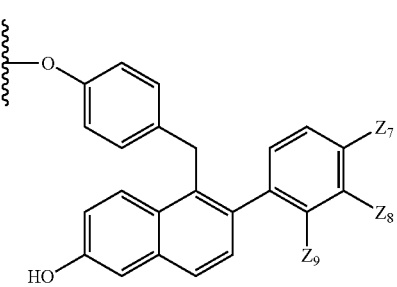
(17)
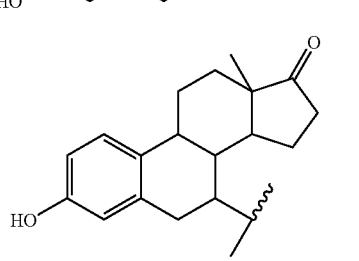

-continued

(18)
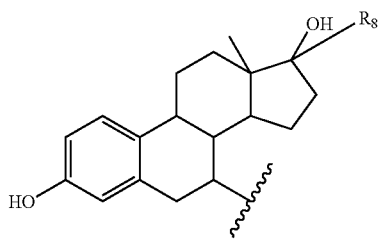

(19)
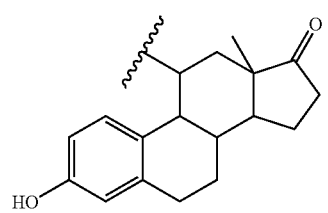

(20)
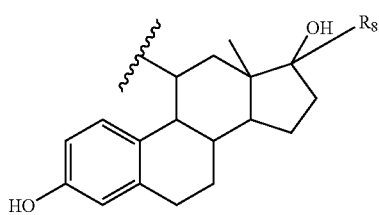

(21)
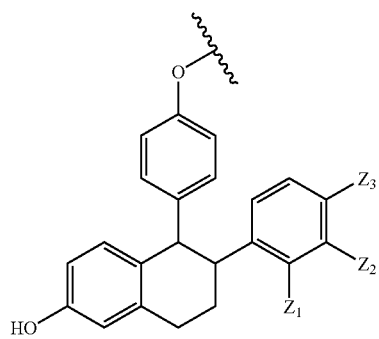

(22)
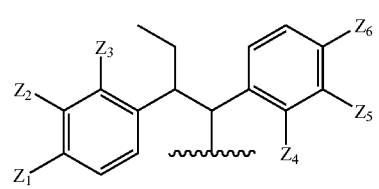

(23)
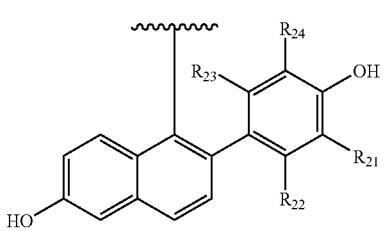

-continued

(24)
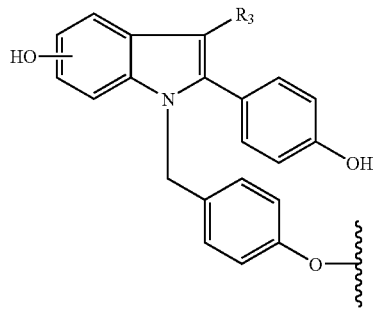

(25)
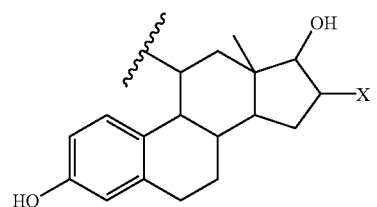

(26)
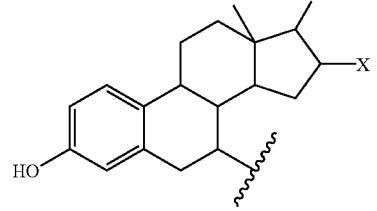

in which in formulae (6), (7), (14) and (24), each of $R_3$ and $R_6$ represents a linear or branched $C_1$–$C_5$ alkyl group, in formulae (10), (11) and (12), $Z_{10}$ represents a hydrogen atom or an acyl group, in formulae (13), (21) and (22), each of $Z_1$, $Z_2$, $Z_3$, $Z_4$, $Z_5$ and $Z_6$ independently represents a hydrogen atom, a hydroxyl group or a linear or branched $C_1$–$C_5$ alkyl group, in formula (15), $R_7$ represents a hydrogen atom or a linear or branched $C_1$–$C_5$ alkyl group, in formula (16), each of $Z_7$, $Z_8$ and $Z_9$ independently represents a hydrogen atom or a hydroxyl group, in formulae (18) and (20), $R_8$ represents a linear or branched $C_1$–$C_5$ alkyl group, a linear or branched $C_2$–$C_5$ alkenyl group or a linear or branched $C_2$–$C_5$ alkynyl group, in formula (23), each of $R_{21}$, $R_{22}$, $R_{23}$ and $R_{24}$ independently represents a hydrogen atom, a linear or branched $C_1$–$C_5$ alkyl group, a linear or branched $C_1$–$C_7$ halogenoalkyl group, a halogen atom or an acyl group, and in formulae (25) and (26), X represents a halogen atom, or enantiomers of the compound, or hydrates or pharmaceutically acceptable salts of the compound or enantiomers thereof.

Furthermore, the present invention provides a pharmaceutical composition comprising a compound of general formula (2) as an active ingredient. The present invention also provides an anti-estrogenic pharmaceutical composition comprising the above compound as an active ingredient. The present invention further provides a therapeutic agent for breast cancer comprising a compound of general formula (2) as an active ingredient.

As used herein, the term "parent scaffold(s)" refers to a partial structure shared by a class of compounds having the same or similar pharmacological effects or physicochemical properties. The parent scaffolds include, but are not limited to, the following structures: steroid, indole, naphthalene, benzofuran, benzothiophene, benzopyran, benzoxazine, 3,4-diphenyl-[4.3.0]-nonane, 4-(1,2-diphenyl-1-butenyl)phenol, flavone, erythromycin, alkaloid, cephalosporin, β-lactam, and derivatives thereof.

Compounds having low activity following oral administration refer to those compound which are incapable of showing adequate activity for a desired pharmacological effect when administered orally because they are poorly absorbed from the intestinal tract or rapidly metabolized in the body. Examples include certain types of anti-tumor compounds, certain types of estrogenic compounds (e.g., estradiol) and anti-estrogenic compounds.

Compounds having anti-tumor activity include all types of compounds capable of inhibiting tumor growth. The present invention is particularly advantageous to those compounds showing low activity by oral route.

Compounds having estrogenic activity refer to those compounds which have affinity for the estrogen receptor and enhance the signaling mediated by the estrogen receptor. Examples include estradiol.

Compounds having anti-estrogenic activity refer to those compounds which have an antagonistic activity against estrogen's pharmacological effects. Examples include the compounds described in the prior art reports mentioned above.

The present invention provides compounds wherein a moiety is chemically bonded to a group, wherein said moiety containing a compound having low activity following oral administration, a compound having anti-tumor activity, a compound having estrogenic activity or a compound having anti-estrogenic activity or the parent scaffolds of these compounds and said group having the general formula (1). As used herein, the term "chemically bonded" means that the group is bonded through a covalent bond and the like, including a C—C bond, a C—O bond, a C—N bond, etc. The moiety containing the above-mentioned compounds or their parent scaffolds may take any structure as long as these bonds are possible. A C—C bond is preferably used to improve stability against metabolism and hence activity by oral route.

Salt-forming metals as $R_1$ include, but are not limited to, alkali metals such as sodium and potassium, alkaline earth metals such as magnesium and calcium, rare earth metals such as cerium and samarium, as well as zinc and tin. Among these, alkali metals and alkaline earth metals are preferred.

$R_1$ may preferably be a hydrogen atom, an alkali metal and an alkaline earth metal.

Halogens in the linear or branched $C_1$–$C_7$ halogenoalkyl groups as $R_2$ include fluorine, chlorine, bromine and iodine, with fluorine being preferred. $R_2$ may contain one or more halogen atoms. When $R_2$ contains two or more halogen atoms, they may be the same or different, preferably the same halogen atoms. In particular, $R_2$ is preferably a perhalogenoalkyl group. Alkyls in the linear or branched $C_1$–$C_7$ halogenoalkyl groups under consideration include, but are not limited to, methyl, ethyl, n-propyl, i-propyl, n-butyl, i-butyl, sec-butyl, tert-butyl, n-pentyl, 1-methylbutyl, 2-methylbutyl, 3-methylbutyl, 1,1-dimethylpropyl, 1,2-dimethyl-propyl, 2,2-dimethylpropyl, 1-ethylpropyl, n-hexyl and n-heptyl. Preferred are linear or branched $C_1$–$C_4$ alkyls, i.e., methyl, ethyl, n-propyl, i-propyl and n-butyl.

Examples of the linear or branched $C_1$–$C_7$ perhalogenoalkyl group as $R_2$ include the above-listed linear or branched $C_1$–$C_7$ alkyl groups, provided that they are perhalogenated, preferably perfluorinated. Also preferred are perhalogenated linear or branched $C_1$–$C_5$ alkyl groups and a group of the following general formula (9):

in which each of $R_4$ and $R_5$ which may be the same or different represents a linear or branched $C_1$–$C_3$ perhalogenoalkyl group. Among them, perfluorinated groups are preferred. More specifically, a perfluoromethyl group, a perfluoroethyl group, a perfluoro-n-propyl group and a perfluoro-n-butyl group are particularly preferred.

In the case where $R_2$ in general formula (2) is a group of general formula (9), examples of the linear or branched $C_1$–$C_3$ perhalogenoalkyl group as $R_4$ and $R_5$ include the above-listed linear or branched $C_1$–$C_3$ alkyl groups, provided that they are perhalogenated, preferably perfluorinated. Further, perhalogenated $C_1$ alkyl groups are preferred and a perfluorinated group is particularly preferred. More specifically, a perfluoromethyl group is preferred.

In the case where $R_2$ in general formula (2) is a group of general formula (9), $R_2$ is preferably a 1,1,1,3,3,3-hexafluoroisopropyl group.

Having the definition given above, $R_2$ is preferably a perfluoroethyl group, a perfluoro-n-propyl group, a perfluoro-n-butyl group, and a 1,1,1,3,3,3-hexafluoro-isopropyl group.

Examples of the linear or branched $C_1$–$C_5$ alkyl group as used herein include, but are not limited to, methyl, ethyl, n-propyl, i-propyl, n-butyl, i-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl and 1-ethylpropyl.

Examples of the linear or branched $C_2$–$C_5$ alkenyl group as used herein include, but are not limited to, vinyl, allyl, 1-butenyl, 2-butenyl and 3-butenyl.

Examples of the linear or branched $C_2$–$C_5$ alkynyl group as used herein include, but are not limited to, ethynyl, propynyl, 1-butynyl, 2-butynyl and 3-butynyl.

Examples of the acyl group as used herein include, but are not limited to, alkylcarbonyl groups such as formyl, acetyl, propionyl, butyryl, isobutyryl, valeryl, isovaleryl, pivaloyl, caproyl and phenylacetyl; alkenylcarbonyl groups such as acryloyl, propyoloyl, methacryloyl, crotonoyl and isocrotonoyl; and arylcarbonyl groups such as benzoyl.

Examples of the linear or branched $C_1$–$C_7$ halogenoalkyl group as $R_{21}$, $R_{22}$, $R_{23}$ and $R_{24}$ may be the same groups as previously listed for $R_2$.

Group A may preferably be any one of the groups having formulae (3) to (8) and (10) to (23), particularly groups having formulae (3) to (6), (17) to (20) and (23), and more particularly groups having formulae (3), (4) and (17) to (20).

m may preferably be an integer of 4 to 10.

n may preferably be an integer of 2 to 7.

The group of general formula (1), which is one component of the compound according to the present invention, has an asymmetric center, while the other component may have an asymmetric center. Further, the compound of general formula (2) according to the present invention may have an asymmetric center in group A in addition to the asymmetric center in the group of general formula (1). For this reason, the compounds of the present invention have enantiomers. All individual enantiomers and mixtures thereof are intended to be within the scope of the present invention. When group A having an asymmetric center is a steroid scaffold represented by any one of formulae (3), (4) and (17) to (20), the group of general formula (1) is preferably attached to the steroid parent scaffold at 7α- or 11β-position.

Also, in the general formulae(1) and (2), both compounds with R- and S-configuration of the asymmetric carbon to which carboxylic acid or its metal salt is attached are preferable.

Among compounds of general formula (2), preferred are those compounds in which $R_1$ is a hydrogen atom, an alkali metal or an alkaline earth metal; $R_2$ is a perfluoroethyl group, a perfluoro-n-propyl group, a perfluoro-n-butyl group or a 1,1,1,3,3,3-hexafluoroisopropyl group; m is an integer of 4 to 10; and n is an integer of 2 to 6.

The compounds of the present invention may be obtained as hydrates.

Pharmaceutically acceptable salts include, but are not limited to, the above-mentioned metal salts, for example, sodium, potassium and calcium salts.

The compound according to the present invention may be administered as a pharmaceutical composition in any dosage form suitable for the intended route of administration, in combination with one or more pharmaceutically acceptable diluents, wetting agents, emulsifiers, dispersants, auxiliary agents, preservatives, buffers, binders, stabilizers and the like. The compound and composition may be administered parenterally or orally.

The dose of the compound can be suitably determined according to the physique, age and physical condition of a patient, severity of the disease to be treated, elapsed time after onset of the disease, etc. Because the compound of the present invention is expected to show a significantly high activity by oral route, it is generally used in an amount of 0.1 to 500 mg/day when orally administered and in an amount of 0.1–1000 mg/day to 0.1–1000 mg/month when parenterally administered (by intravenous, intramuscular, or subcutaneous route) for adult patient.

BEST MODE FOR CARRYING OUT THE INVENTION

The compound of general formula (1), particularly the compound of general formula (2), can be prepared according to any one of the following Reaction Schemes A to K and 1 to 19. In these Reaction Schemes A to K and 1 to 19 (i.e., Processes A to K and 1 to 19), $R_2$, $R_3$, $R_6$, $R_7$, $Z_1$, $Z_2$, $Z_3$, $Z_4$, $Z_5$, $Z_6$, $Z_7$, $Z_8$, $Z_9$, $Z_{10}$, m and n are as defined above in general formulae (1) and (2); each of $R_{11}$, $R_{12}$, $R_{13}$ and $R_{16}$ represents a protecting group; $R_{33}$ represents a linear or branched alkyl group; each of $Y_1$, $Y_2$, $Y_3$, $Y_4$, $Y_5$ and $Y_6$ independently represents a hydrogen atom, an alkyl group (e.g., a linear or branched $C_1$–$C_5$ alkyl group) or $OR_{11}$; each of $L_1$ and $L_2$ represents a leaving group; X represents a halogen atom; $m_1$ is m-2; $R_8$ represents a linear or branched $C_1$–$C_5$ alkyl group, a linear or branched $C_2$–$C_5$ alkenyl group or a linear or branched $C_2$–$C_5$ alkynyl group.

The compound of the present invention may include various stereoisomers because it contains one or more asymmetric carbon atoms. To obtain a single stereoisomer, there are two techniques, one of which uses a chiral column to resolve a mixture of stereoisomers and the other involves asymmetric synthesis. The chiral column technique may be carried out using a column commercially available, from DAICEL under the trade name of CHIRALPAK-OT(+), OP(+) or AD, or CHIRALCEL-OA, OB, OJ, OK, OC, OD, OF or OG, for example. Regarding asymmetric synthesis, Processes 14 to 16 illustrate the asymmetric synthesis of the inventive compound with respect to an asymmetric carbon atom, to which a side chain carboxyl group is attached.

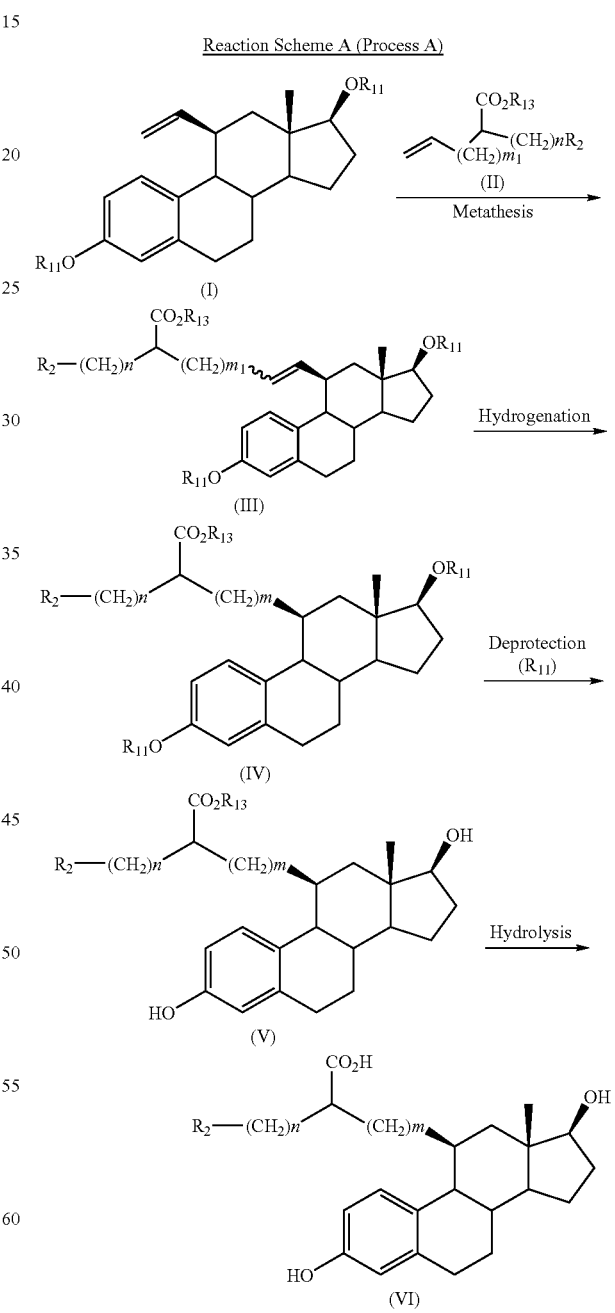

Note: Compound (I) can be synthesized by the method described in J. Org. Chem., 60(1995) 5316–5318.

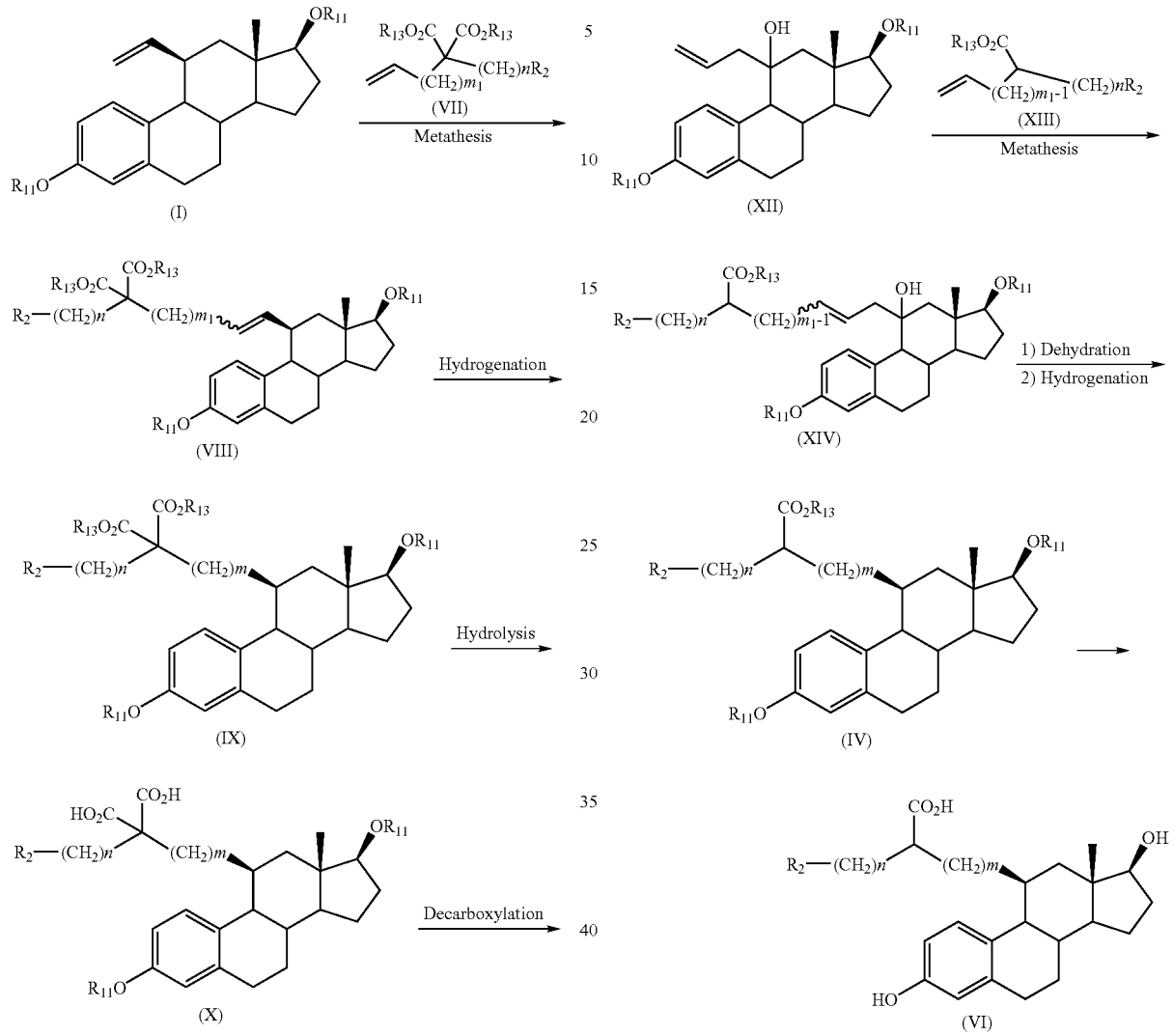

-continued

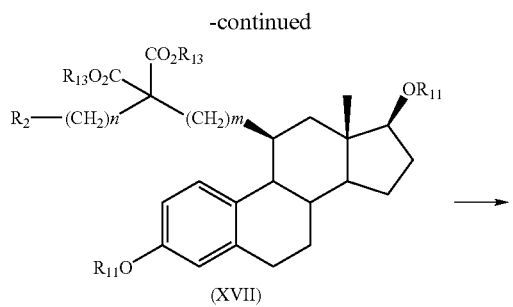
(XVII)

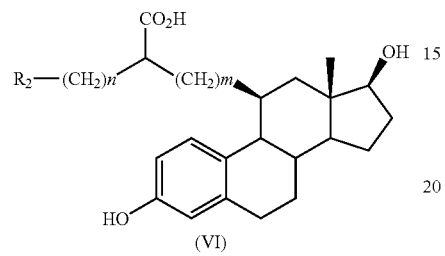
(VI)

Reaction Scheme E (Process E)

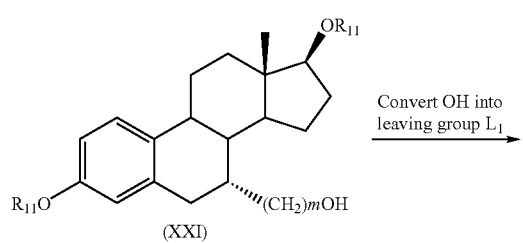
(XXI)

Convert OH into leaving group $L_1$ →

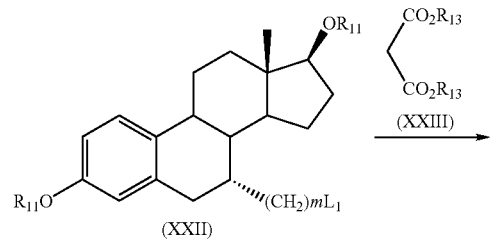
(XXII)

$\begin{array}{c}CO_2R_{13}\\CO_2R_{13}\end{array}$ (XXIII)

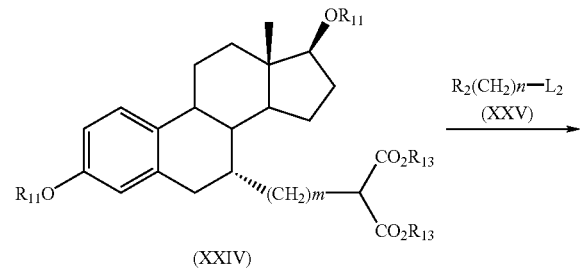
(XXIV)

$R_2(CH_2)n\text{—}L_2$ (XXV) →

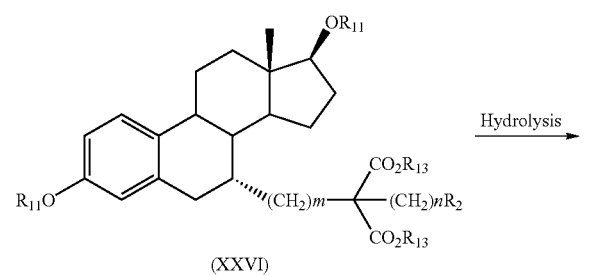
(XXVI)

Hydrolysis →

-continued

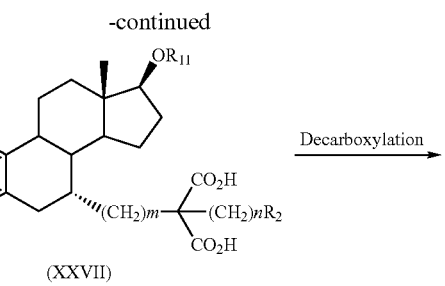
(XXVII)

Decarboxylation →

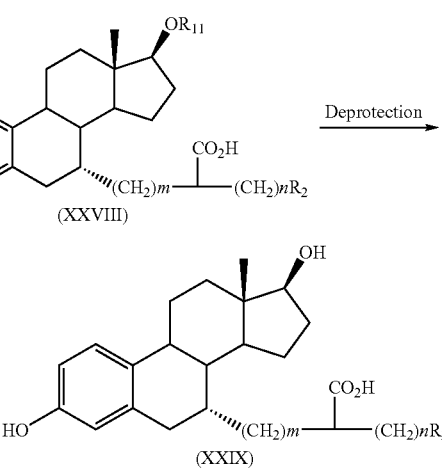
(XXVIII)

Deprotection →

(XXIX)

Note: Compound (XXI) can be synthesized by the method described in DE4218743A1.

Reaction Scheme F (Process F)

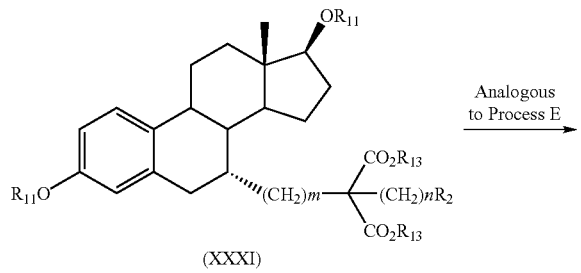
(XXII)

$\begin{array}{c}R_{13}O_2C\\R_{13}O_2C\end{array}$ $(CH_2)n\text{—}R_2$ (XXX) →

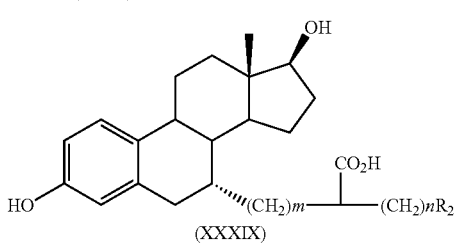
(XXXI)

Analogous to Process E (XXXIX)

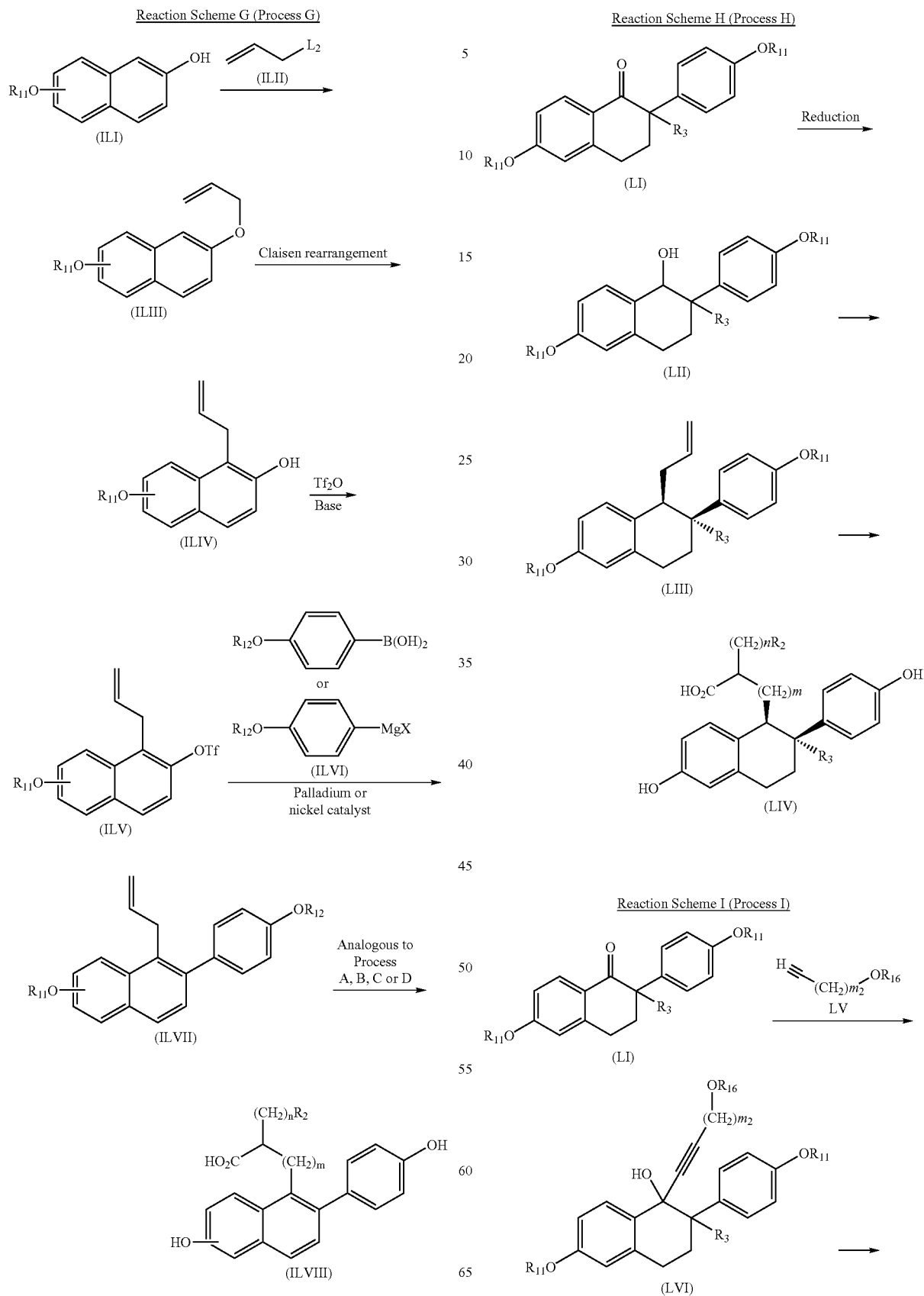

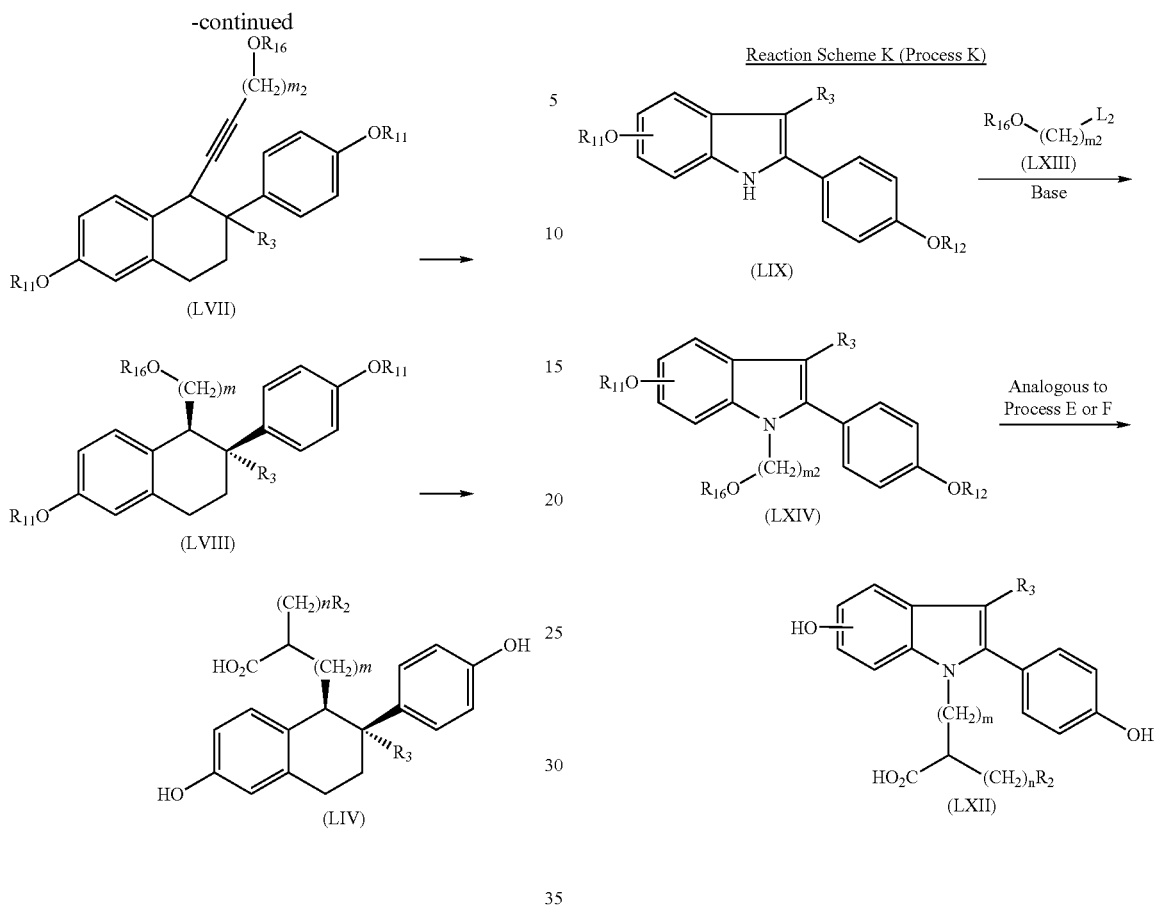
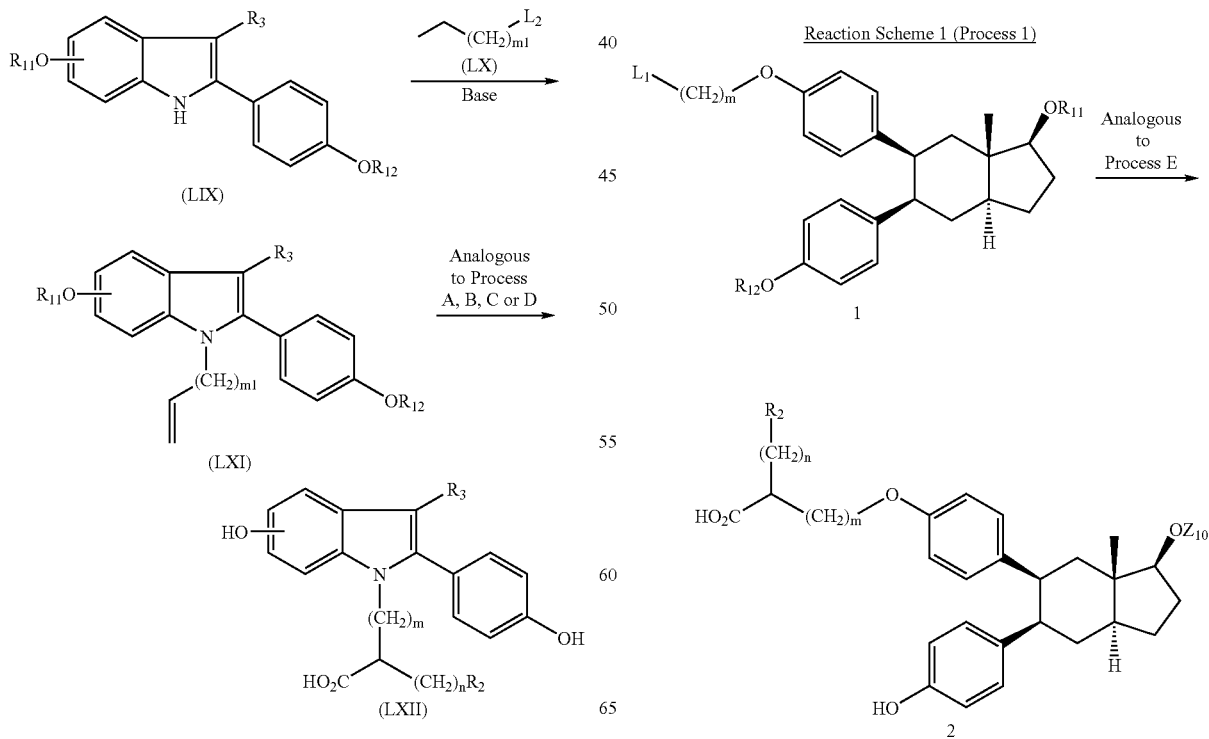

-continued
Reaction Scheme 2 (Process 2)
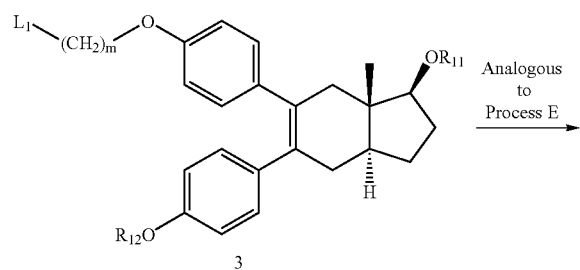
3
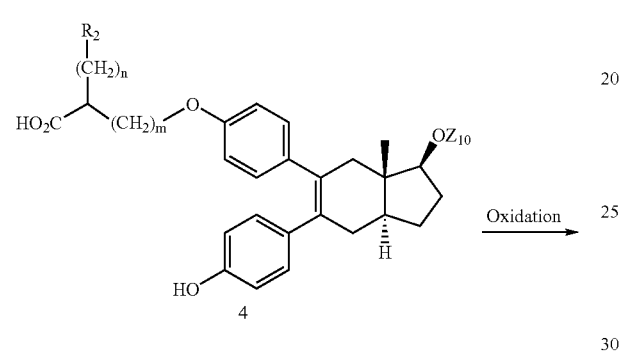
4
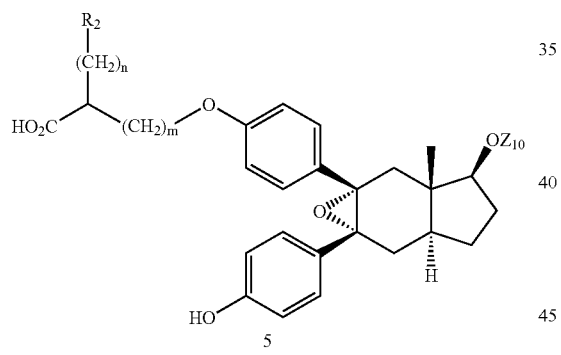
5
Reaction Scheme 3 (Process 3)
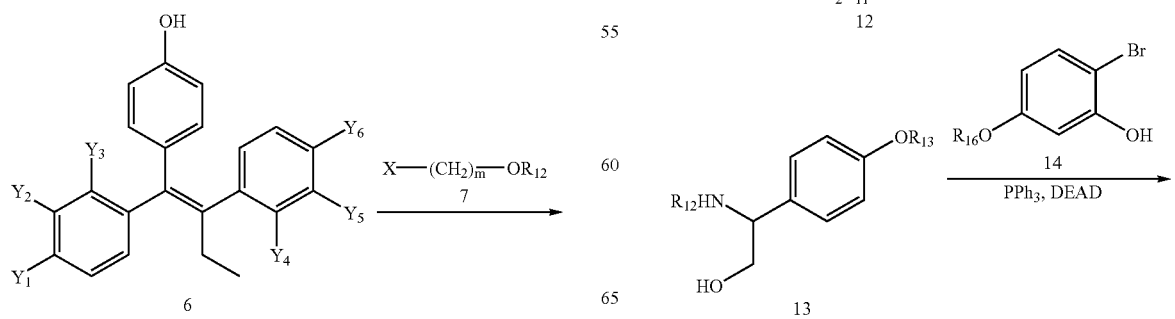
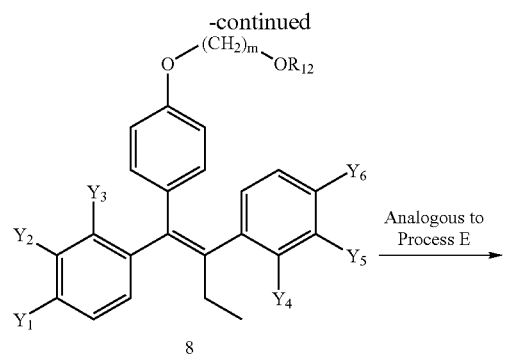
8
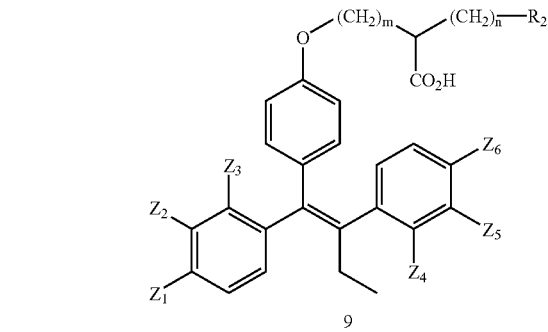
9
Reaction Scheme 4 (Process 4)
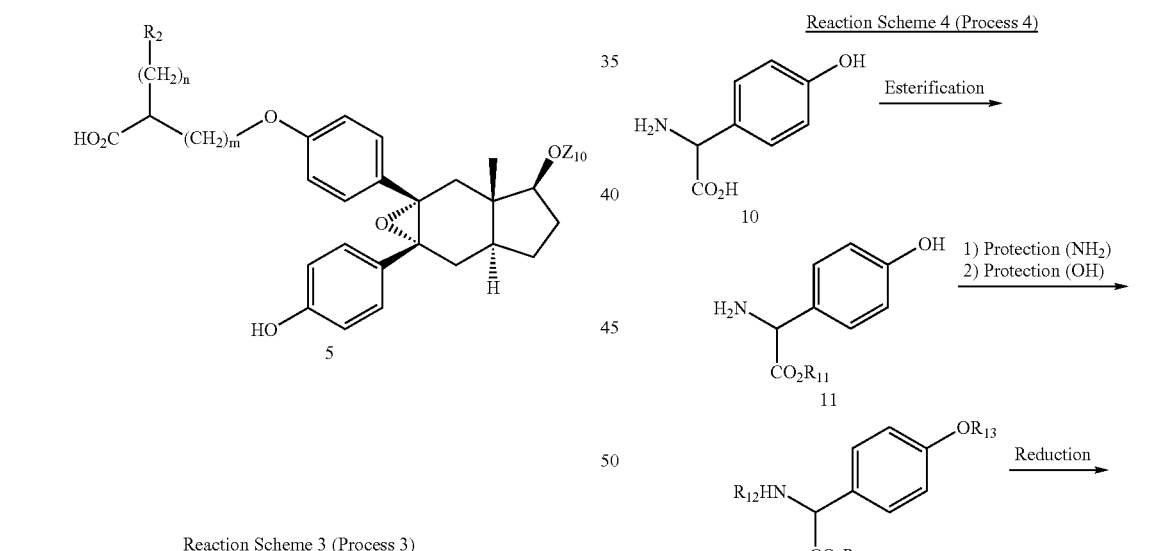

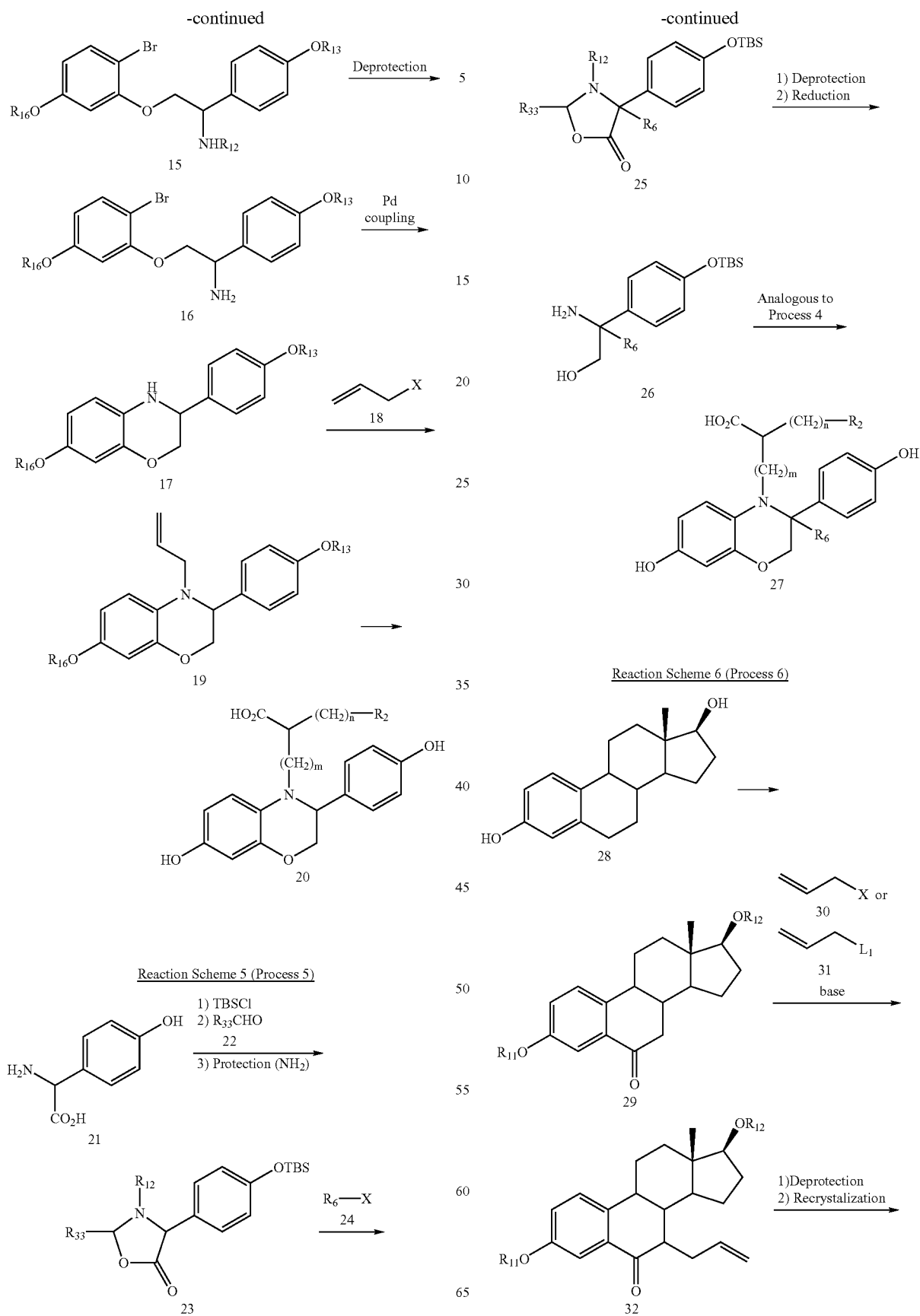

-continued

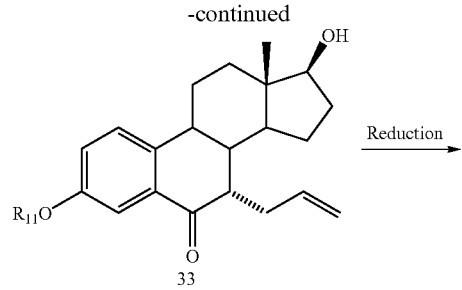
33

Reduction →

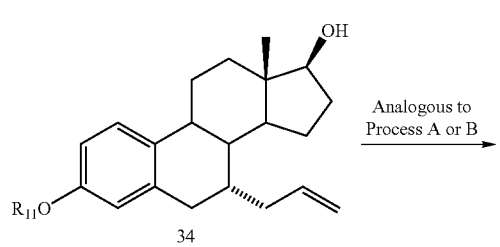
34

Analogous to Process A or B →

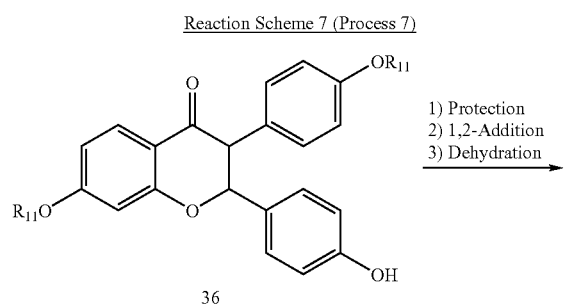
35

Reaction Scheme 7 (Process 7)

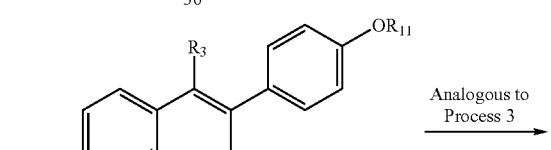
36

1) Protection
2) 1,2-Addition
3) Dehydration →

37

Analogous to Process 3 →

38

Reaction Scheme 8 (Process 8)

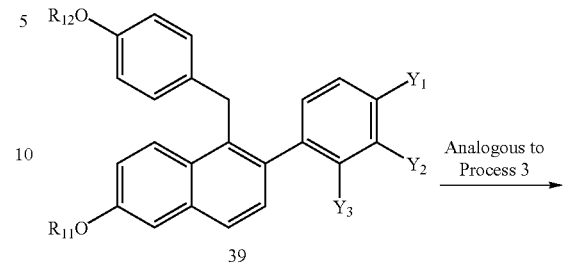
39

Analogous to Process 3 →

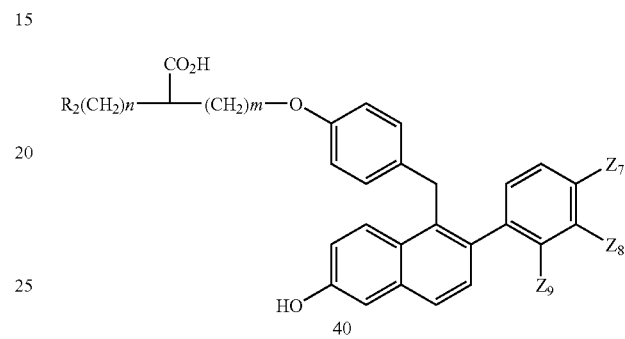
40

Reaction Scheme 9 (Process 9)

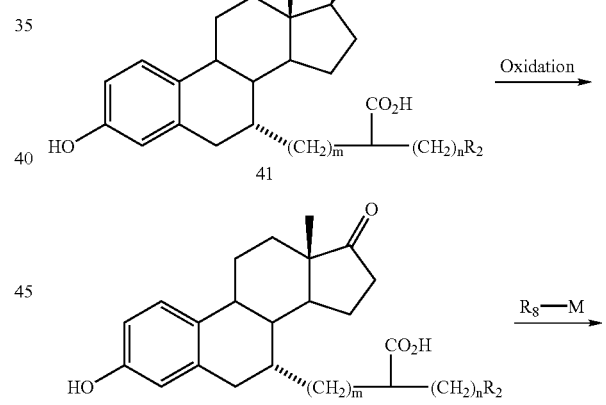
41

Oxidation →

42

$R_8$—M →

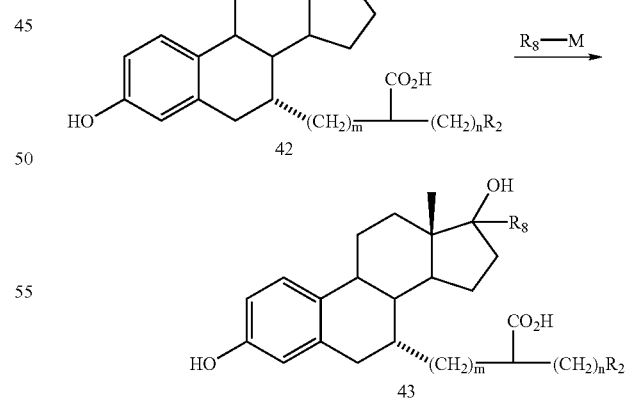
43 in which $R_8$ represents a linear or branched $C_1$–$C_5$ alkyl group, a linear or branched $C_2$–$C_5$ alkenyl group or a linear or branched $C_2$–$C_5$ alkynyl group, and M represents a metal.

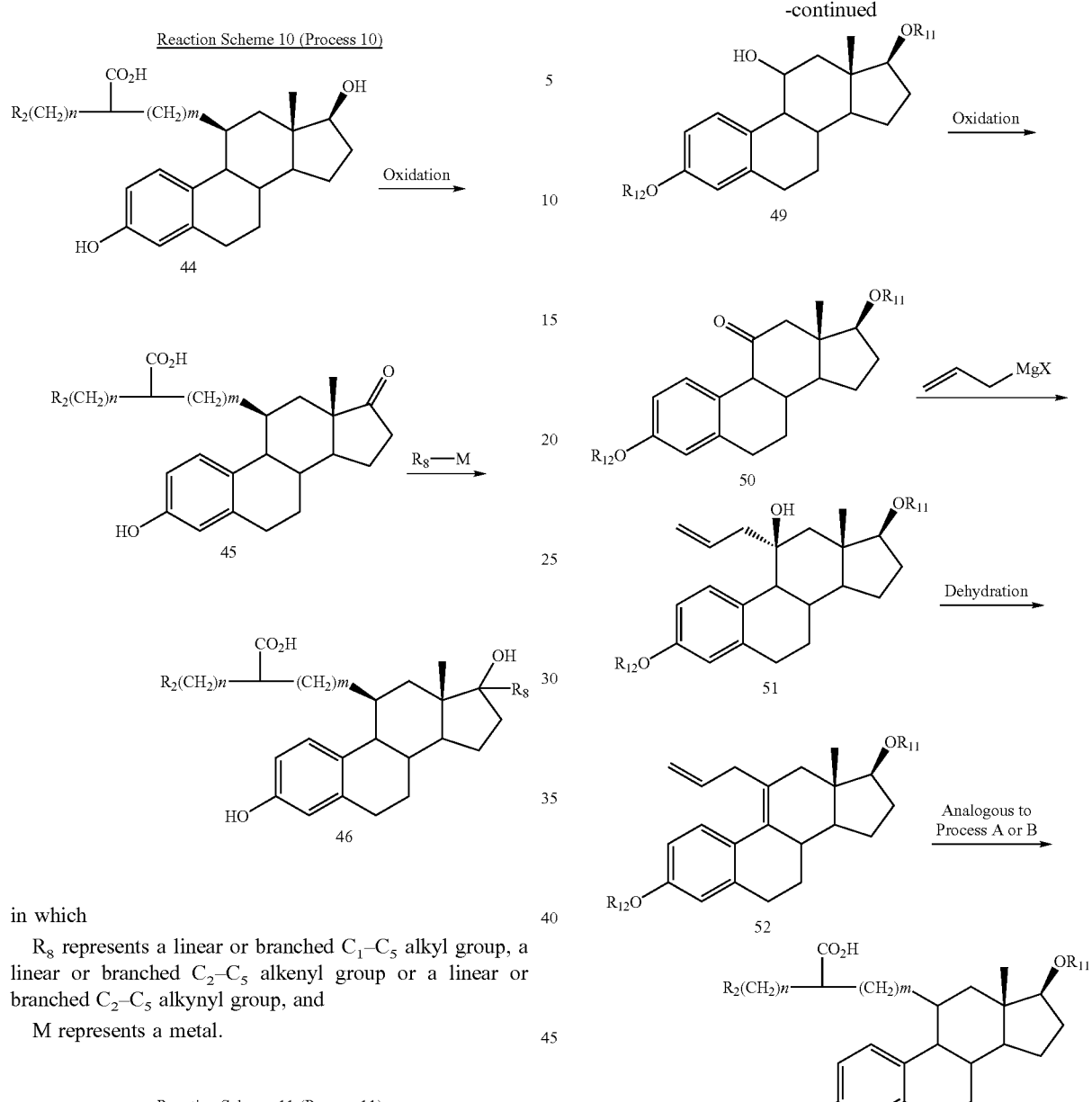
in which
R$_8$ represents a linear or branched C$_1$–C$_5$ alkyl group, a linear or branched C$_2$–C$_5$ alkenyl group or a linear or branched C$_2$–C$_5$ alkynyl group, and
M represents a metal.
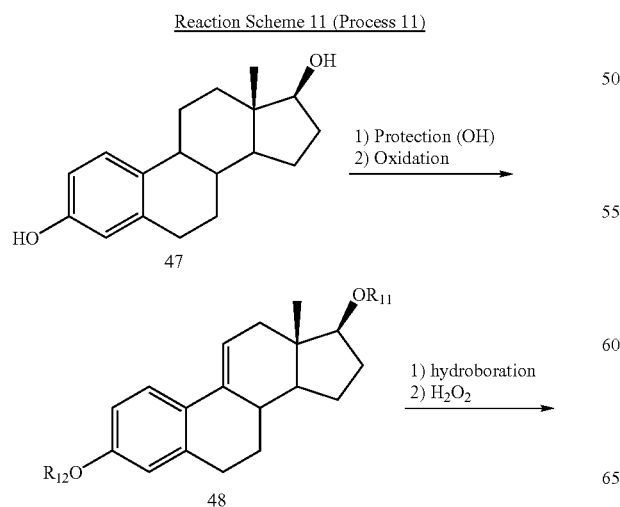
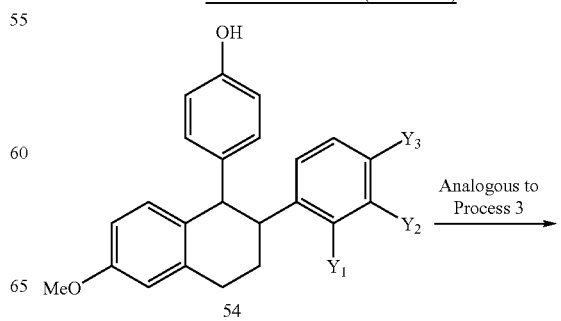

-continued

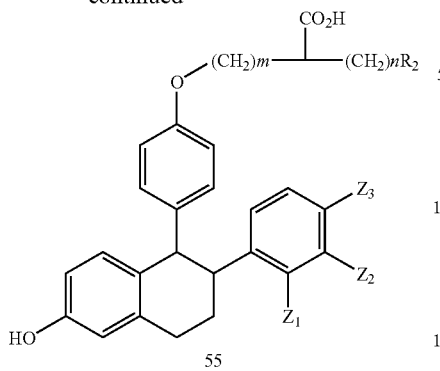

in which
each of $Y_1$, $Y_2$ and $Y_3$ independently represents a hydrogen atom, an alkyl group (e.g., a linear or branched $C_1$–$C_5$ alkyl group) or $OR_{11}$, and
each of $Z_1$, $Z_2$ and $Z_3$ independently represents a hydrogen atom, a hydroxyl group or a linear or branched $C_1$–$C_5$ alkyl group.

Reaction Scheme 13 (Process 13)

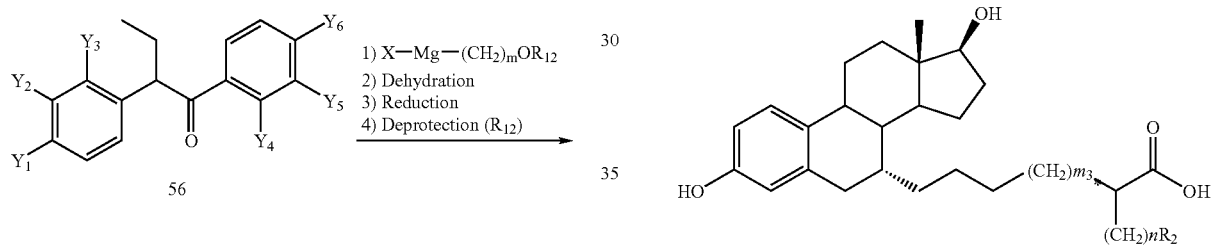

in which
each of $Y_1$, $Y_2$, $Y_3$, $Y_4$, $Y_5$ and $Y_6$ independently represents a hydrogen atom, an alkyl group (e.g., a linear or branched $C_1$–$C_5$ alkyl group) or $OR_{11}$, and
each of $Z_1$, $Z_2$, $Z_3$, $Z_4$, $Z_5$ and $Z_6$ independently represents a hydrogen atom, a hydroxyl group or a linear or branched $C_1$–$C_5$ alkyl group.

Reaction Scheme 14 (Process 14)

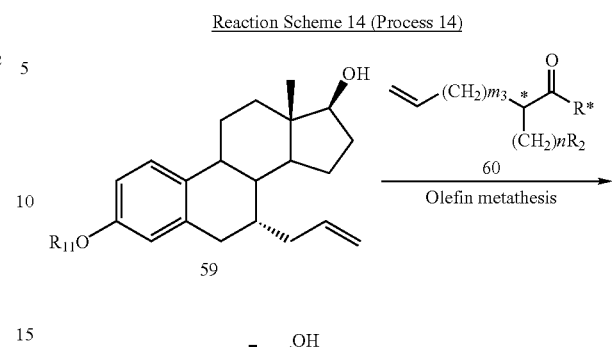

Examples of R* include:

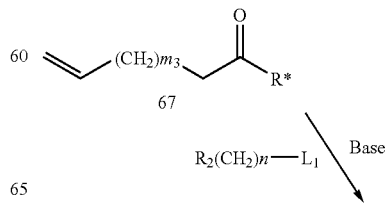

Reaction Scheme 15 (Process 15)

-continued
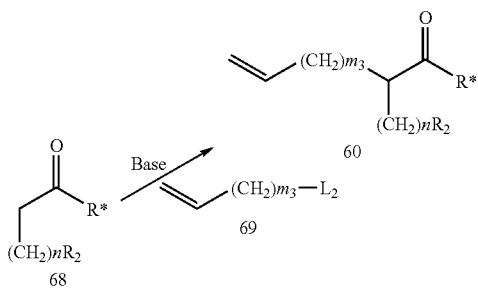
Examples of R* include:
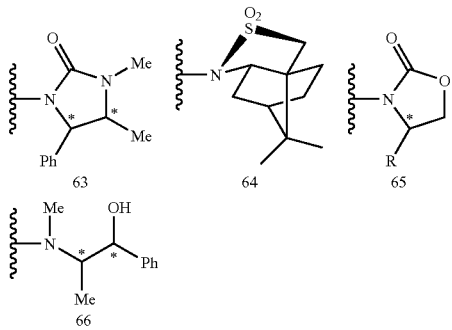
In the above Reaction Schemes 14 and 15 (Processes 14 and 15), $R_2$, $R_{11}$, $R_{12}$, X, m, n, X, $L_1$ and $L_2$ are as defined above, R* represents a chiral auxiliary, and m and $m_3$ are integers that satisfy the relation $m = m_3 + 3$.
Reaction Scheme 16 (Process 16)
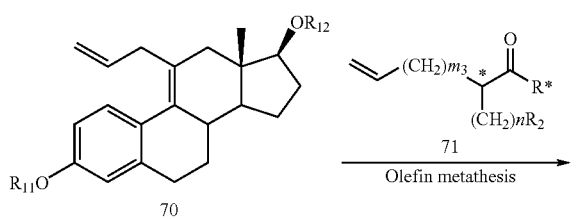
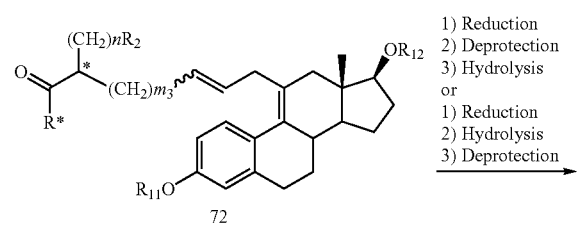
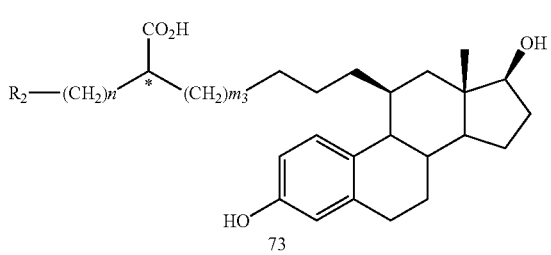
-continued
Examples of R* include:
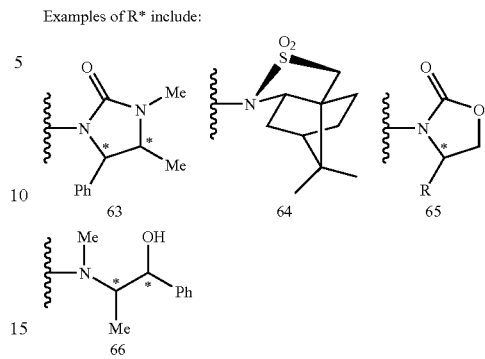
Reaction Scheme 17 (Process 17)
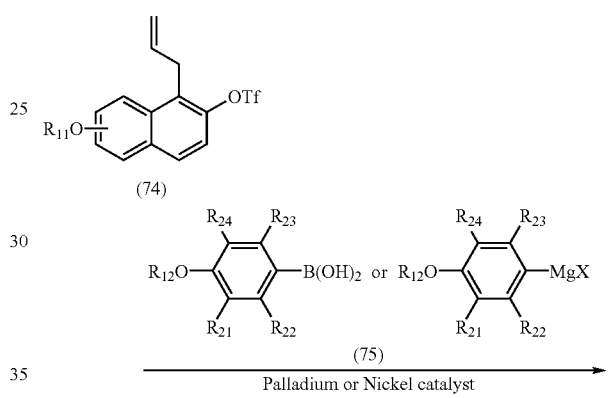
Reaction Scheme 18 (Process 18)

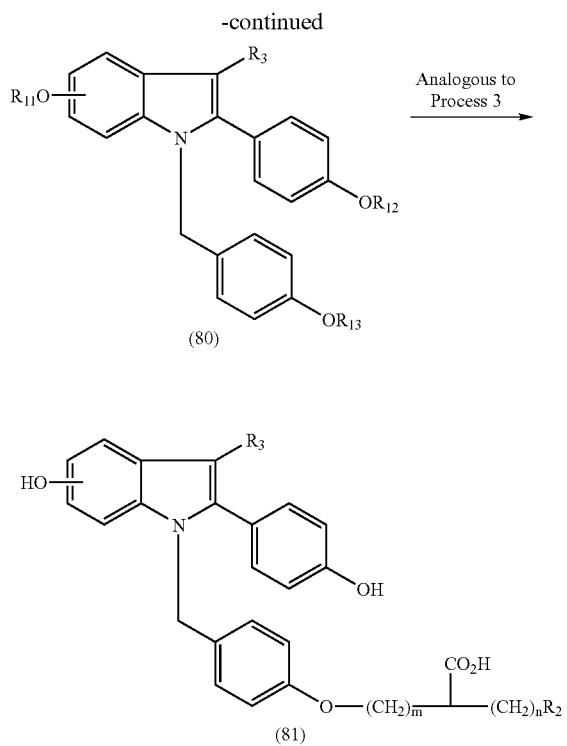

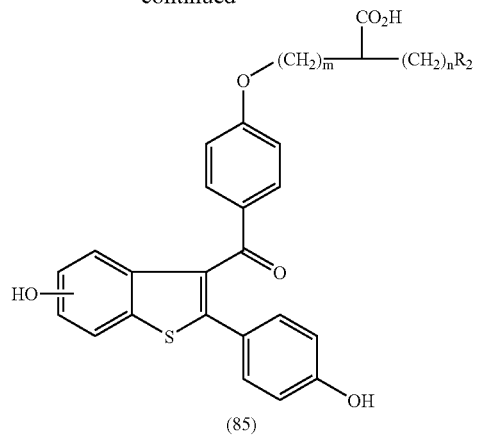

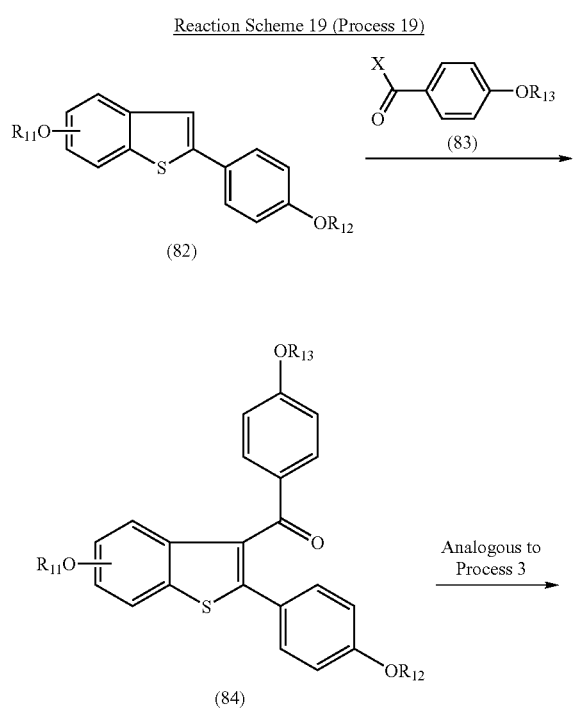

[Process A]

Process A illustrates the synthesis of compound (VI) starting with compound (I). Compound (I) can be synthesized by the method described in J. Org. Chem., 60(1995) 5316–5318.

Step 1: Preparation of Compound (III)

In the presence of a catalyst such as benzylidene-bis(tricyclohexylphosphine)dichlororuthenium, compound (I) is reacted with compound (II) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (III).

Step 2: Preparation of Compound (IV)

Using a catalyst (e.g., palladium on activated carbon, palladium hydroxide, platinum oxide or Wilkinson's catalyst), compound (III) is hydrogenated in an inert solvent (e.g., methanol, ethanol, ethyl acetate, tetrahydrofuran, dioxane, dichloromethane, dichloroethane, chloroform or benzene) at a temperature ranging from room temperature to the boiling point of the reaction mixture, preferably at the boiling point of the reaction mixture, to give compound (IV).

Step 3: Preparation of Compound (V)

When $R_{11}$ is, for example, a methyl group, compound (IV) is treated with an acid (e.g., hydrogen chloride, sulfuric acid, hydrogen bromide, pyridine hydrochloride or boron tribromide) at a temperature ranging from −78° C. to the boiling point of the reaction mixture to give compound (V).

Step 4: Preparation of Compound (VI)

Compound (V) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (VI).

[Process B]

As shown below, compound (VI) given by Process A can also be prepared starting with compound (I) in the following manner.

Step 1: Preparation of Compound (VIII)

In the presence of a catalyst such as benzylidene-bis(tricyclohexylphosphine)dichlororuthenium, compound (I) is reacted with compound (VII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (VIII).

Step 2: Preparation of Compound (IX)

Using a catalyst (e.g., palladium on activated carbon, palladium hydroxide, platinum oxide or Wilkinson's catalyst), compound (VIII) is hydrogenated in an inert solvent (e.g., methanol, ethanol, ethyl acetate, tetrahydrofuran, dioxane, dichloromethane, dichloroethane, chloroform or benzene) at a temperature ranging from room temperature to the boiling point of the reaction mixture, preferably at the boiling point of the reaction mixture, to give compound (IX).

Step 3: Preparation of Compound (X)

Compound (IX) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (X).

Step 4: Preparation of Compound (XI)

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (X) is heated to a temperature ranging from 50° C. to the boiling point of the reaction mixture to give compound (XI).

Step 5: Preparation of Compound (VI)

When $R_{11}$ is, for example, a methyl group, compound (XI) is treated with an acid (e.g., hydrogen chloride, sulfuric acid, hydrogen bromide, pyridine hydrochloride or boron tribromide) at a temperature ranging from −78° C. to the boiling point of the reaction mixture to give compound (VI).

[Process C]

As shown below, compound (VI) given by Processes A and B can also be prepared starting with compound (XII) in the following manner.

Step 1: Preparation of Compound (XIV)

In the presence of a catalyst such as benzylidene-bis(tricyclohexylphosphine)dichlororuthenium, compound (XII) is reacted with compound (XIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XIV).

Step 2: Preparation of Compound (IV)

Compound (XIV) is dehydrated using an acid (e.g., hydrochloric acid, hydrobromic acid, hydrobromic acid/acetic acid) in an inert solvent (e.g., methanol, ethanol) at a temperature ranging from room temperature to the boiling point of the reaction mixture, preferably at 50° C., and further processed by hydrogenation analogous to Process A to give compound (IV).

Step 3: Preparation of Compound (VI)

Compound (IV) is subjected to hydrolysis and deprotection analogous to Process A or B to give compound (VI).

[Process D]

As shown below, compound (VI) given by Processes A, B and C can also be prepared starting with compound (XII) in the following manner.

Step 1: Preparation of Compound (XVI)

In the presence of a catalyst such as benzylidene-bis(tricyclohexylphosphine)dichlororuthenium, compound (XII) is reacted with compound (XV) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XVI).

Step 2: Preparation of Compound (XVII)

Compound (XVI) is dehydrated using an acid (e.g., hydrochloric acid, hydrobromic acid, hydrobromic acid/acetic acid) in an inert solvent (e.g., methanol, ethanol) at a temperature ranging from room temperature to the boiling point of the reaction mixture, preferably at 50° C., and further processed by hydrogenation analogous to Process A to give compound (XVII).

Step 3: Preparation of Compound (VI)

Compound (XVII) is subjected to hydrolysis, decarboxylation and deprotection by a procedure analogous to Process A or B to give compound (VI).

Compound (XII) used as a starting material in Processes C and D can be prepared according to the method described in Tetrahedron., 30(1977) pp. 609–616.

[Process E]

Process E illustrates the synthesis of compound (XXIX) starting with compound (XXI).

Step 1: Preparation of Compound (XXII)

In the presence of an organic base (e.g., triethylamine or pyridine), compound (XXI) is treated with an acid chloride (e.g., methanesulfonyl chloride or p-toluenesulfonyl chloride) in an inert solvent (e.g., tetrahydrofuran, dioxane, dichloromethane, dichloroethane or chloroform, preferably dichloromethane) at a temperature ranging from room temperature to the boiling point of the reaction mixture, preferably at room temperature, to convert $(CH_2)_m OH$ in compound (XXI) into $(CH_2)_m$-$L_1$, in which $L_1$ is —O—$SO_2CH_3$ or —O—$SO_2$—$C_6H_4$-p-$CH_3$, for example. The compound thus obtained is then treated with a metal halide (e.g., sodium iodide or potassium iodide) in an inert solvent (e.g., acetone, tetrahydrofuran, dioxane, dichloromethane, dichloroethane or chloroform, preferably acetone) at a temperature ranging from room temperature to the boiling point of the reaction mixture, preferably at the boiling point of the reaction mixture, to give compound (XXII).

Step 2: Preparation of Compound (XXIV)

In the presence of a base (e.g., sodium hydride, sodium hydroxide or potassium t-butoxide), compound (XXII) is reacted with a malonic ester (XXIII) (e.g., diethyl malonate or dimethyl malonate) in an inert solvent (e.g., tetrahydrofuran, dioxane, dichloromethane, dichloroethane or chloroform, preferably tetrahydrofuran) at a temperature ranging from room temperature to the boiling point of the reaction mixture to give compound (XXIV).

Step 3: Preparation of Compound (XXVI)

In the presence of a base (e.g., sodium hydride, sodium hydroxide or potassium t-butoxide), compound (XXIV) is reacted with an alkyl halide (XXV), in which $L_2$ represents a halogen atom, in an inert solvent (e.g., tetrahydrofuran, dioxane, dichloromethane, dichloroethane or chloroform, preferably tetrahydrofuran) at a temperature ranging from room temperature to the boiling point of the reaction mixture to give compound (XXVI).

Step 4: Preparation of Compound (XXVII)

Compound (XXVI) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (XXVII).

Step 5: Preparation of Compound (XXVIII)

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XXVII) is heated to a temperature ranging from 50° C. to the boiling point of the reaction mixture to give compound (XXVIII).

Step 6: Preparation of Compound (XXIX)

When $R_{11}$ is, for example, a methyl group, compound (XXVIII) is treated with an acid (e.g., hydrogen chloride, sulfuric acid, hydrogen bromide, pyridine hydrochloride or boron tribromide) at a temperature ranging from −78° C. to the boiling point of the reaction mixture to give compound (XXIX).

Compound (XXI) used as a starting material in Process E can be prepared according to the method described in DE4218743A1.

[Process F]

Compound (XXIX) given by Process E can also be prepared starting with compound (XXII) according to the following steps.

Step 1: Preparation of Compound (XXXI)

In the presence of a base (e.g., sodium hydride, sodium hydroxide or potassium t-butoxide), compound (XXII) is reacted with compound (XXX) in an inert solvent (e.g., tetrahydrofuran, dioxane, dichloromethane, dichloroethane or chloroform, preferably tetrahydrofuran) at a temperature ranging from −78° C. to the boiling point of the reaction mixture to give compound (XXXI).

Step 2: Preparation of Compound (XXIX)

Compound (XXXI) is converted into compound (XXIX) by a procedure analogous to Process E.

[Process G]

Process G illustrates the synthesis of compound (ILVIII) starting with compound (ILI).

Step 1: Preparation of Compound (ILIII)

In the presence of a base (e.g., sodium carbonate, potassium carbonate, sodium hydroxide, potassium hydroxide, barium hydroxide, lithium hydroxide, sodium hydride, preferably potassium carbonate), compound (ILI) is reacted with compound (ILII) in an inert solvent (e.g., acetone, methyl ethyl ketone, tetrahydrofuran, preferably acetone) at a temperature ranging from −78° C. to the boiling point of the reaction mixture, preferably at room temperature, to give compound (ILIII).

Step 2: Preparation of Compound (ILIV) Via Claisen Rearrangement

Compound (ILIII) is dissolved in an inert solvent (e.g., N,N-dimethyl aniline, N,N-diethyl aniline, nitrobenzene, dichlorobenzene, dibromobenzene, preferably N,N-dimethyl aniline) and then heated to a temperature ranging from 180° C. to the boiling point of the reaction mixture, preferably from 180° C. to 200° C., to give compound (ILIV).

Step 3: Preparation of Compound (ILV)

In the presence of a base (e.g., triethylamine, diethylisopropylamine, pyridine, sodium carbonate, potassium carbonate, sodium hydroxide, potassium hydroxide, sodium hydride, preferably pyridine), compound (ILIV) is reacted with $Tf_2O$ (trifluoromethanesulfonic anhydride) in an inert solvent (e.g., dichloromethane, chloroform, benzene, toluene, preferably dichloromethane) at a temperature ranging from 0° C. to room temperature to give compound (ILV).

Step 4: Preparation of Compound (ILVII)

In the presence of a palladium or nickel catalyst, compound (ILV) is reacted with compound (ILVI) in an inert solvent (e.g., ether, tetrahydrofuran, dioxane, dimethylformamide, water, preferably dioxane) at a temperature ranging from room temperature to the boiling point of the reaction mixture, preferably at the boiling point of the reaction mixture, to give compound (ILVII).

Step 5: Preparation of Compound (ILVIII)

Compound (ILVII) is converted into compound (ILVIII) by a procedure analogous to Process A, B, C or D.

[Process H]

Process H illustrates the synthesis of compound (LIV) starting with compound (LI) synthesized by the method described in U.S. Pat. No. 4,904,661.

Step 1: Preparation of Compound (LII)

Compound (LI) is reacted with a reducing agent (e.g., lithium aluminum hydride, diisobutylaluminum hydride, sodium borohydride) in an inert solvent (e.g., tetrahydrofuran, dioxane, diethyl ether) at a temperature ranging from 0° C. to the boiling point of the reaction mixture, preferably from 0° C. to 50° C., to give compound (LII).

Step 2: Preparation of Compound (LIII)

In the presence of a suitable acid (e.g., zinc iodide, boron trifluoride), compound (LII) is reacted with allyl-trimethylsilane in an inert solvent (e.g., dichloroethane, dichloromethane, chloroform) at a temperature ranging from 0° C. to the boiling point of the reaction mixture, preferably from 0° C. to 50° C., to give compound (LIII).

Step 3: Preparation of Compound (LIV)

Compound (LIII) is subjected to analogous procedure to Process A, B, C or D, that is, metathesis, reduction, hydrolysis, decarboxylation, deprotection, etc. to give compound (LIV).

[Process I]

Compound (LIV) can also be synthesized starting with compound (LI) in the following manner.

Step 1: Preparation of Compound (LVI)

In the presence of a base (e.g., sodium hydride, n-butyllithium, t-butyllithium, lithium diisopropylamide, potassium tert-butoxide), compound (LI) is reacted with compound (LV) in an inert solvent (e.g., tetrahydrofuran, dioxane, diethyl ether) at a temperature ranging from −78° C. to the boiling point of the reaction mixture, preferably from −78° C. to 0° C., to give compound (LVI).

Step 2: Preparation of Compound (LVII)

In the presence of a suitable acid (e.g., zinc iodide, boron trifluoride), compound (LVI) is reacted with sodium cyanoborohydride in an inert solvent (e.g., dichloroethane, dichloromethane, chloroform) at a temperature ranging from 0° C. to the boiling point of the reaction mixture, preferably from 0° C. to 50° C., to give compound (LVII).

Step 3: Preparation of Compound (LVIII)

In the presence of a catalyst (e.g., palladium on activated carbon, palladium hydroxide, platinum oxide), compound (LVII) is hydrogenated in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature, to give compound (LVIII). Compound (LVIII) can be directly prepared form compound (LVI) through hydrogenation using a catalyst (e.g., palladium on activated carbon, palladium hydroxide or platinum oxide) in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature.

Step 4: Preparation of Compound (LIV)

Compound (LVIII) is reacted by a procedure analogous to Process E or F to give compound (LIV).

[Process J]

Process J illustrates the synthesis of compound (LXII) starting with compound (LIX).

Step 1: Preparation of Compound (LXI)

In the presence of a base (e.g., sodium hydride, n-butyllithium, potassium tert-butoxide), compound (LIX) is reacted with compound (LX) in an inert solvent (e.g., dimethylformamide, tetrahydrofuran, dioxane, diethyl ether, dimethyl sulfoxide) at a temperature ranging from 0° C. to the boiling point of the reaction mixture, preferably from 0° C. to 50° C., to give compound (LXI).

Step 2: Preparation of Compound (LXII)

Compound (LXI) is subjected to metathesis, reduction, hydrolysis and deprotection by a procedure analogous to Process A, B, C or D to give compound (LXII).

[Process K]

Compound (LXII) can also be synthesized starting with compound (LIX) in the following manner.

Step 1: Preparation of Compound (LXIV)

In the presence of a base (e.g., sodium hydride, n-butyllithium, potassium tert-butoxide), compound (LIX) is reacted with compound (LXIII) in an inert solvent (e.g., dimethylformamide, tetrahydrofuran, dioxane, diethyl ether, dimethyl sulfoxide) at a temperature ranging from 0° C. to the boiling point of the reaction mixture, preferably from 0° C. to 50° C., to give compound (LXIV).

Step 2: Preparation of Compound (LXII)

Compound (LXIV) is reacted by a procedure analogous to Process E or F to give compound (LXII).

Compounds of general formula (2) in which group A is represented by formula (8) can be prepared, for example, as shown in Examples 6 to 10 by the same or equivalent procedure.

[Process 1]

Compound 2 is prepared starting with compound 1 by a procedure analogous to Process E. Compound 1 used as a starting material can be prepared according to the method described in WO99/64393.

[Process 2]

Compound 4 is prepared starting with compound 3 by a procedure analogous to Process E. Compound 5 can be obtained by oxidizing compound 4 according to the method described in WO99/64393. Compound 3 used as a starting material can be prepared according to the method described in WO99/64393.

[Process 3]

Process 3 illustrates the synthesis of compound 9 starting with compound 6. Compound 6 used as a starting material can be synthesized by, for example, the methods described in J. Org. Chem., 50(1985) 2121–2123 and J. Org. Chem., 61(1996) 3890–3893.

Step 1: Preparation of Compound 8

In the presence of a base (e.g., sodium hydride, n-butyllithium, potassium tert-butoxide), compound 6 is reacted with compound 7 in an inert solvent (e.g., dimethylformamide, tetrahydrofuran, dioxane, diethyl ether, dimethyl sulfoxide) at a temperature ranging from 0° C. to the boiling point of the reaction mixture, preferably from 0° C. to 50° C., to give compound 8.

Step 2: Preparation of Compound 9 Compound 8 is reacted by a procedure analogous to Process E to give compound 9.

[Process 4]

Process 4 illustrates the synthesis of compound 20 starting with compound 10.

Step 1: Preparation of Compound 11

In the presence of an acid catalyst such as sulfuric acid, compound 10 is heated in an alcohol (e.g., methanol, ethanol) at a temperature ranging from −78° C. to the boiling point of the reaction mixture, preferably at the boiling point of the reaction mixture, to give compound 11.

Step 2: Preparation of Compound 12

Amino and hydroxyl groups of compound 11 prepared in Step 1 are protected to give compound 12.

Step 3: Preparation of Compound 13

Compound 12 is treated with a reducing agent (e.g., lithium borohydride, etc.) in a solvent (e.g., methanol, ethanol or ethanol/tetrahydrofuran) at a temperature ranging from −78° C. to the boiling point of the reaction mixture, preferably at room temperature, to give compound 13.

Step 4: Preparation of Compound 15

Compound 13 is subjected to Mitsunobu reaction with compound 14 to give compound 15.

Step 5: Preparation of Compound 16

Compound 15 is subjected to deprotection of the amino group to give compound 16.

Step 6: Preparation of Compound 17

In the presence of a base (e.g., potassium carbonate, potassium t-butoxide, sodium t-butoxide), compound 16 is reacted by addition of a metal catalyst such as palladium along with a ligand such as diphenylphosphino ferrocene or 2,2-bis(diphenylphosphino)-1,1'-binaphthyl, preferably by addition of a tris(dibenzylideneacetone)dipalladium catalyst along with 2,2-bis(diphenylphosphino)-1,1'-binaphthyl, in an inert solvent (e.g., benzene, toluene, xylene, dioxane or tetrahydrofuran) at a temperature ranging from −78° C. to the boiling point of the reaction mixture, preferably at 100° C., to give compound 17.

Step 7: Preparation of Compound 19

In the presence of a base (e.g., sodium hydride, n-butyllithium, potassium tert-butoxide, potassium carbonate) and, if necessary, by addition of a reagent such as sodium iodide, compound 17 is reacted with compound 18 in an inert solvent (e.g., dimethylformamide, tetrahydrofuran, dioxane, diethyl ether, dimethyl sulfoxide, acetone) at a temperature ranging from 0° C. to the boiling point of the reaction mixture, preferably at the boiling point of the reaction mixture, to give compound 19.

Step 8: Preparation of Compound 20

Compound 19 is reacted by a procedure analogous to Process A or B to give compound 20.

[Process 5]

Process 5 illustrates the synthesis of compound 27 starting with compound 21.

Step 1: Preparation of Compound 23

Compound 21 is subjected to protection with TBS, then reacted with aldehyde 22, and then protected at its amino group, to give compound 23.

Step 2: Preparation of Compound 25

Compound 23 prepared in Step 1 is alkylated with compound 24 to give compound 25.

Step 3: Preparation of Compound 26

Compound 25 is subjected to deprotection of the amino group and then treated with a reducing agent (e.g., lithium aluminum hydride, etc.) in a solvent (e.g., tetrahydrofuran, ether) at a temperature ranging from −78° C. to the boiling point of the reaction mixture, preferably at room temperature, to give compound 26.

Step 4: Preparation of Compound 27

Compound 26 is reacted by a procedure analogous to Process 4 to give compound 27.

[Process 6]

Process 6 illustrates the synthesis of compound 35 starting with compound 28.

Compound 35 can be synthesized starting with compound 28 in the following manner.

Step 1: Preparation of Compound 29

Compound 29 is prepared from compound 28 by the method described in Synthesis, 12(1995) 1493–1495 or by an equivalent method.

Step 2: Preparation of Compound 32

In the presence of a base (e.g., lithium hexamethyldisilazide, sodium hexamethyl-disilazide, potassium hexamethyl-disilazide, sodium hydride, n-butyllithium, t-butyllithium, lithium diisopropylamide, potassium tert-butoxide, aqueous potassium hydroxide, aqueous sodium hydroxide), compound 29 is reacted with compound 30 or 31 in an inert solvent (e.g., 1,2-dimethoxyethane, tetrahydrofuran, dioxane, t-butyl methyl ether, diethyl ether, dimethyl sulfoxide, N,N-dimethylformamide, N,N-dimethylacetamide, toluene) at a temperature ranging from −78° C. to the boiling point of the reaction mixture, preferably from −78° C. to 0° C., to give compound 32.

Step 3: Preparation of Compound 33

Compound 32 is isomerized under a basic condition (e.g., tetrabutylammonium fluoride/tetrahydrofuran, sodium methoxide/methanol, sodium ethoxide/ethanol, potassium methoxide/methanol, sodium methoxide/propanol, aqueous potassium hydroxide, aqueous sodium hydroxide), followed by deprotection of $R_{12}$ and purification via recrystallization, to give a single isomer of formula 33. In the case where $R_{12}$ is a t-butyldimethylsilyl group, compound 32 is isomerized simultaneously with the removal of TBS by treatment with tetrabutylammonium fluoride and further purified via recrystallization to give the single isomer of formula 33.

Step 4: Preparation of Compound 34

In the presence of a suitable acid (e.g., trifluoroacetic acid, boron trifluoride etherate, titanium tetrachloride, aluminum chloride, trifluoromethanesulfonic acid, hydrochloric acid, sulfuric acid), compound 33 is reacted with triethylsilane in an inert solvent (e.g., dichloroethane, dichloromethane, chloroform, t-butyl methyl ether, toluene) at a temperature ranging from 0° C. to the boiling point of the reaction mixture, preferably from 0° C. to room temperature, to give compound 34.

Step 5: Preparation of Compound 35

Compound 34 is reacted by a procedure analogous to Process A or B to give compound 35.

[Process 7]

Process 7 illustrates the synthesis of compound 38 starting with compound 36.

Compound 38 can be synthesized starting with compound 37 by a procedure analogous to Process 3. Compounds 36 and 37 used as starting materials can be synthesized by the methods described in J. Med. Chem., 40(1997) 2117–2122 and J. Med. Chem., 33(1990) 3222–3229 or by equivalent methods.

[Process 8]

Process 8 illustrates the synthesis of compound 40 starting with compound 39.

Compound 40 can be synthesized starting with compound 39 by a procedure analogous to Process 3. Compound 39 used as a starting material can be synthesized by, for example, the methods described in EP0826670A1 and J. Org. Chem., 60(1995) 739–741.

[Process 9]

Compound 42 or 43 can be synthesized in the following manner. Compound 42 can be synthesized from compound 41 by Jones oxidation, PCC oxidation, Swern oxidation, or ruthenium oxidation (e.g., TPAP) of the 17-hydroxyl group. Compound 42 is further reacted with $R_8$-M, in which $R_8$ represents a lower alkyl group or a lower alkenyl group or a lower alkynyl group and M represents a metal such as lithium, sodium, potassium, magnesium, calcium or aluminum, in an inert solvent (e.g., dimethyl sulfoxide, tetrahydrofuran, ether, dimethylformamide) at a temperature ranging from −78° C. to the boiling point of the reaction mixture, preferably from 0° C. to room temperature, to give compound 43.

Compound 41 used as a starting material can be synthesized by Process E, F or 6.

[Process 10]

Compound 45 or 46 can be synthesized in the following manner. Compound 45 can be synthesized from compound 44 by Jones oxidation, PCC oxidation, Swern oxidation, or ruthenium oxidation (e.g., TPAP) of the 17-hydroxyl group. Compound 45 is further reacted with $R_8$-M, in which $R_8$ represents a lower alkyl group or a lower alkenyl group or a lower alkynyl group and M represents a metal such as lithium, sodium, potassium, magnesium, calcium or aluminum, in an inert solvent (e.g., dimethyl sulfoxide, tetrahydrofuran, ether, dimethylformamide) at a temperature ranging from −78° C. to the boiling point of the reaction mixture, preferably from 0° C. to room temperature, to give compound 46.

Compound 44 used as a starting material can be synthesized by Process A, B, C or D.

[Process 11]

Compound 53 can be synthesized in the following manner.

Compound 47 is subjected to protection of its hydroxyl groups, and then oxidized between 9- and 11-position using DDQ (2,3-dichloro-5,6-dicyanobenzoquinone) and the like to give compound 48.

Compound 48 is converted into compound 49 by the method described in J. Org. Chem., 1995, 60, 5316–5318.

Compound 49 is subjected to Swern oxidation, Jones oxidation, PCC oxidation, or ruthenium oxidation (e.g., TPAP) to give compound 50.

Compound 50 is reacted with an organometallic reagent (e.g., allylmagnesium halide) in an inert solvent (e.g., tetrahydrofuran, ether) at a temperature ranging from −78° C. to the boiling point of the reaction mixture, preferably from −48° C. to room temperature, to give compound 51.

Compound 51 is dehydrated to remove its hydroxyl group using thionyl chloride/pyridine and the like to give compound 52.

Compound 52 can be converted into compound 53 by Process A, B, C or D.

[Process 12]

Compound 55 can be synthesized by subjecting compound 54 to reactions analogous to Process 3. Compound 54 can be synthesized according to documented methods (Drugs Future, 1978, 3, 211–215; J. Med. Chem., 1967, 10, 78–84; J. Med. Chem., 1998, 41, 2928–2931).

[Process 13]

Compound 56 can be converted into compound 57 by the following steps: 1) 1,2-addition with X—Mg—$(CH_2)_m$ $OR_{12}$, 2) dehydration, 3) reduction and 4) deprotection ($R_{12}$), and then subjected to reactions analogous to Scheme E to give compound 58.

[Process 14]

In the presence of a catalyst such as benzylidene-bis(tricyclohexylphosphine)dichlororuthenium, compound 59 is reacted with chiral olefin 60 in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound 61. Compound 61 is then subjected to the following reactions in the order stated, (a) reduction, deprotection and hydrolysis or (b) reduction, hydrolysis and deprotection, to give compound 62.

(a) Reduction, Deprotection and Hydrolysis
1) Reduction

In the presence of a catalyst (e.g., palladium on activated carbon, palladium hydroxide, platinum oxide or Wilkinson's catalyst), compound 61 is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Deprotection

Next, deprotection of the phenolic hydroxyl group is carried out to give a deprotected product.

3) Hydrolysis

By way of example, if R* is a group of formula 63, the deprotected product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a dimethoxyethane/water mixture, a methanol/water mixture, an ethanol/water mixture) at a temperature ranging from room temperature to the boiling point of the reaction mixture, preferably at room temperature, to give compound 62.

(b) Reduction, Hydrolysis and Deprotection
1) Reduction

In the presence of a catalyst (e.g., palladium on activated carbon, palladium hydroxide, platinum oxide or Wilkinson's catalyst), compound 61 is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Hydrolysis

By way of example, if R* is a group of formula 63, the reduced product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a dimethoxyethane/water mixture, a methanol/water mixture, an ethanol/water mixture) at a temperature ranging from room temperature to the boiling point of the reaction mixture, preferably at room temperature, to give a carboxylic acid.

3) Deprotection

Next, deprotection of the phenolic hydroxyl group is carried out to give compound 62.

The chiral olefin of formula 60 used in the above process can be synthesized as shown in Reaction Scheme 15.

[Process 15]

[Synthesis of Chiral Olefin]

In the presence of a base (e.g., lithium diisopropylamide, lithium hexamethyl-disilazide, sodium hexamethyl-disilazide, butyllithium) and HMPA, compound 67 is reacted with $R_2(CH_2)_n$-$L_1$ in an inert solvent (e.g., tetrahydrofuran, toluene, diethyl ether, hexane, preferably tetrahydrofuran) at a temperature ranging from −78° C. to the boiling point of the reaction mixture, preferably from −30° C. to room temperature, to give compound 60.

Chiral olefin 60 can also be synthesized in the following manner.

In the presence of a base (e.g., lithium diisopropylamide, lithium hexamethyl-disilazide, sodium hexamethyl-disilazide, butyllithium) and HMPA, compound 68 is reacted with compound 69 in an inert solvent (e.g., tetrahydrofuran, toluene, diethyl ether, hexane, preferably tetrahydrofuran) at a temperature ranging from −78° C. to the boiling point of the reaction mixture, preferably from −30° C. to room temperature, to give compound 60.

[Process 16]

Compound 70 can be converted into compound 73 by a procedure analogous to Process 14.

[Process 17]

Compound 75 having substituents $R_{21}$, $R_{22}$, $R_{23}$ and $R_{24}$ on its benzene ring can be converted into compound 77 by a procedure analogous to Process G. Each of $R_{21}$, $R_{22}$, $R_{23}$ and $R_{24}$ independently represents a hydrogen atom, a linear or branched $C_1$–$C_5$ alkyl group, a linear or branched $C_1$–$C_7$ halogenoalkyl group, a halogen atom or an acyl group.

[Process 18]

Compound 78 is reacted with compound 79 in the presence of a base to give compound 80. Compound 81 can be synthesized from compound 80 according to Processes 3 and K.

[Process 19]

Compound 82 synthesized according to the method described in J. Chem., 1057(1984) is subjected to Friedel-Craft reaction with compound 83 and then treated according to Process 3.

EXAMPLES

The invention is more specifically explained by the following examples. However, it should be understood that the present invention is not limited to these example in any manner. In order to explain the effectiveness of the compounds according to the present invention, representative compounds were tested for their anti-estrogenic activity in the test example shown below. Table 1 shows chemical structures of the compounds prepared in the Examples.

TABLE 1

| Example No. | Chemical structure |
|---|---|
| 3 | *(structure shown)* |
| 4 | *(structure shown)* |
| 5 | *(structure shown)* |
| 6 | *(structure shown)* |

TABLE 1-continued
| Example No. | Chemical structure |
|---|---|
| 7 | 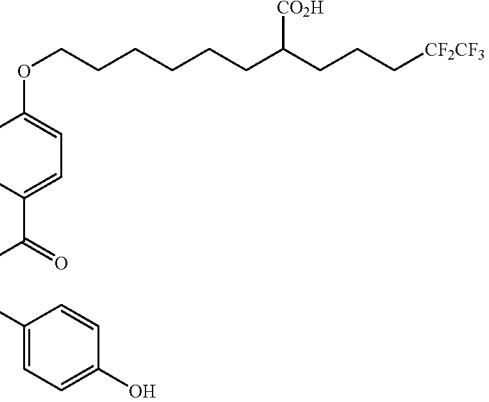 |
| 8 | 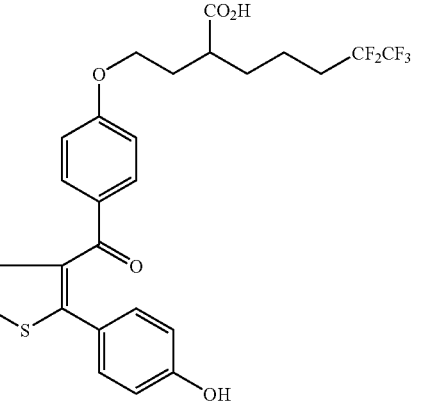 |
| 9 | 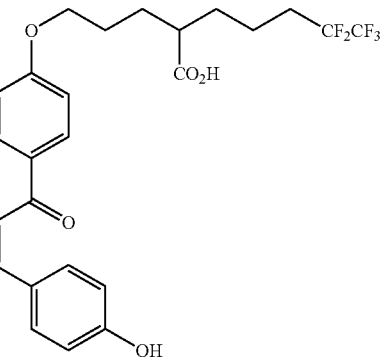 |
| 10 | 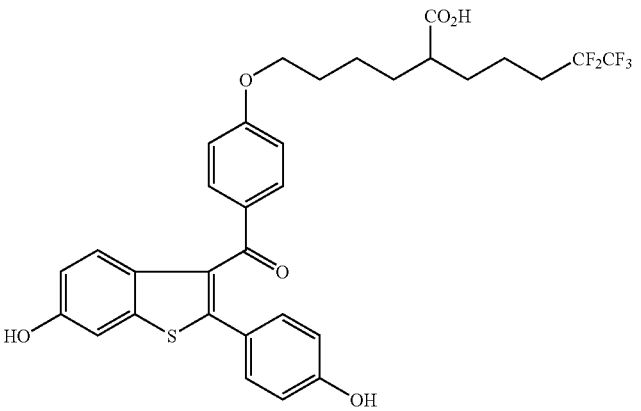 |

TABLE 1-continued
| Example No. | Chemical structure |
|---|---|
| 11 | 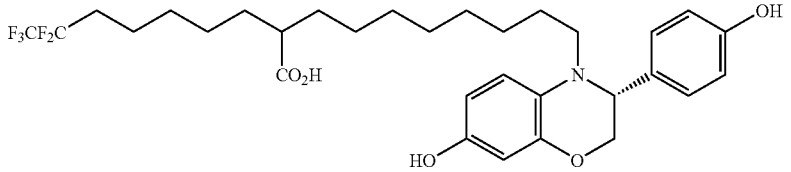 |
| 12 | 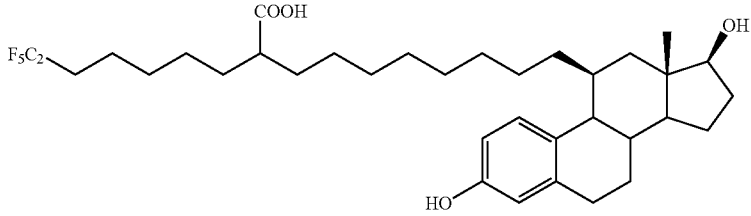 |
| 13 | 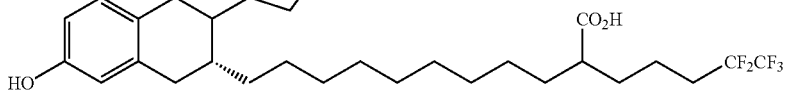 |
| 14 | 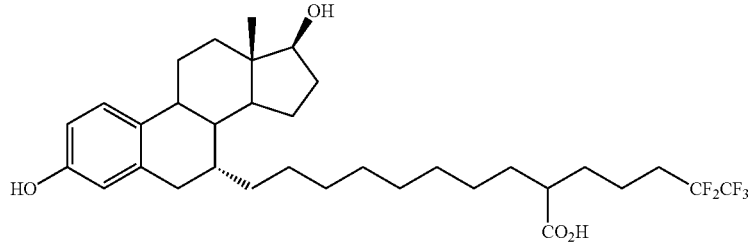 |
| 15 | 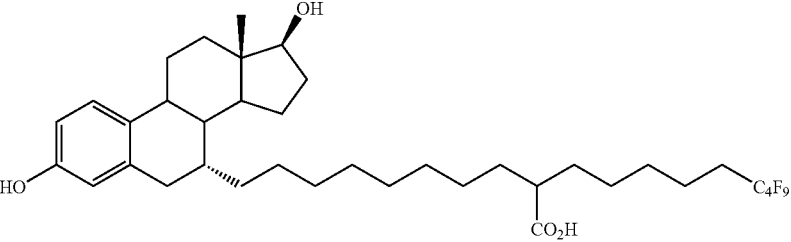 |
| 16 | 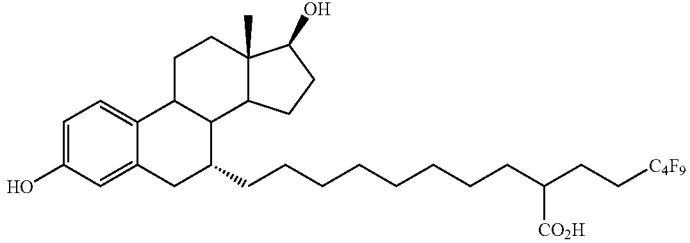 |

TABLE 1-continued

| Example No. | Chemical structure |
| --- | --- |
| 17 | 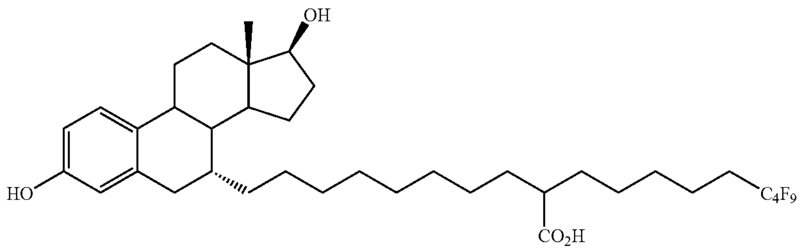 |
| 18 | 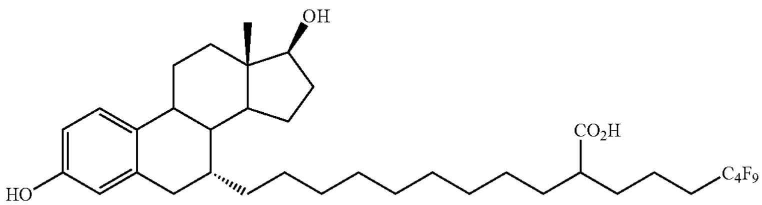 |
| 19 | 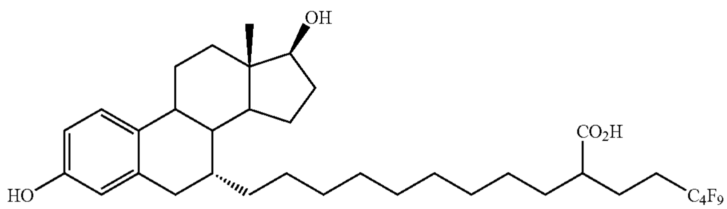 |
| 20 | 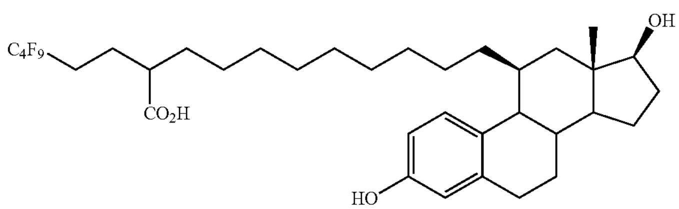 |
| 21 | 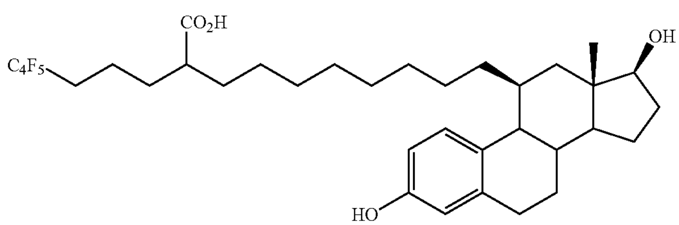 |
| 22 | 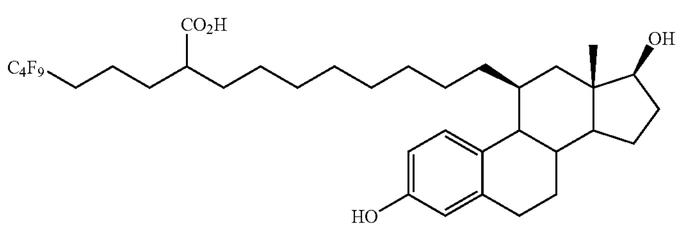 |
| 23 | 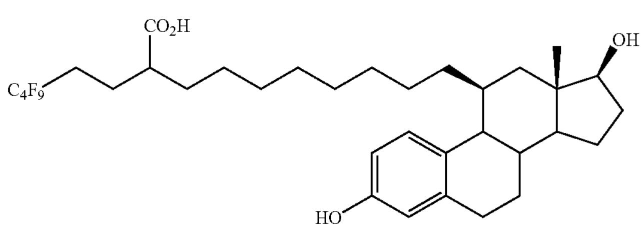 |

TABLE 1-continued
| Example No. | Chemical structure |
|---|---|
| 24 | 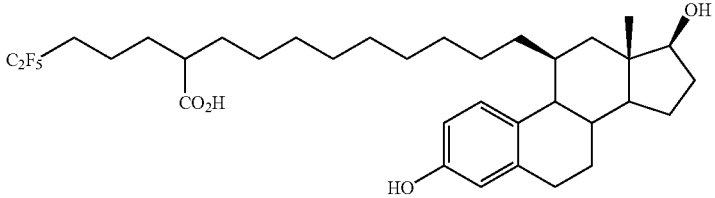 |
| 25 | 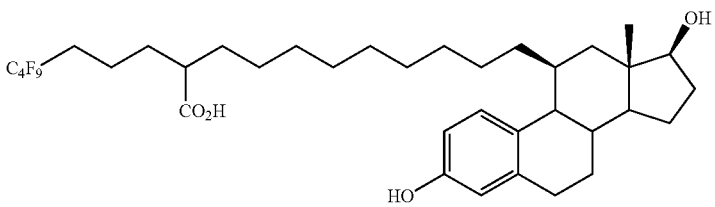 |
| 26 | 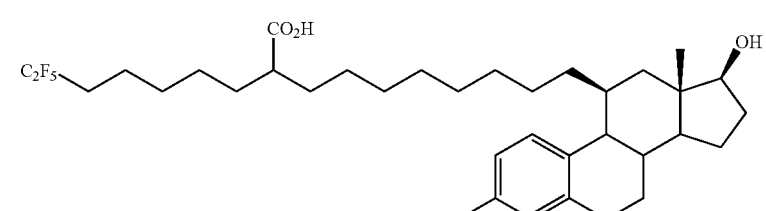 |
| 27 | 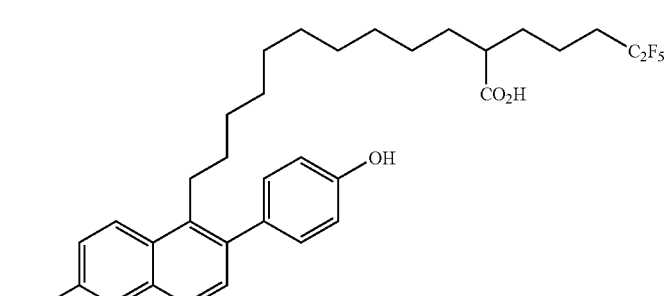 |
| 28 | 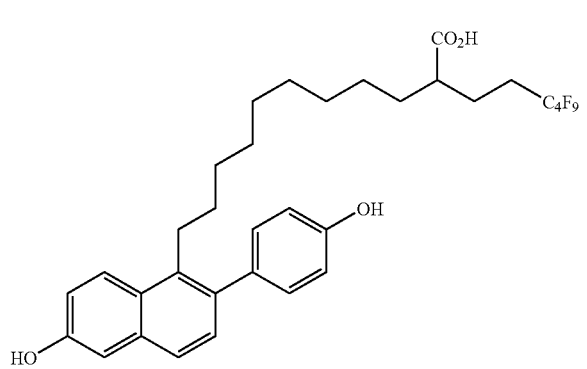 |
| 29 | 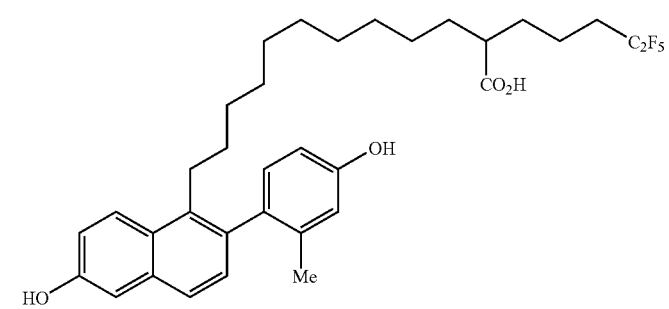 |

TABLE 1-continued
| Example No. | Chemical structure |
|---|---|
| 30 | 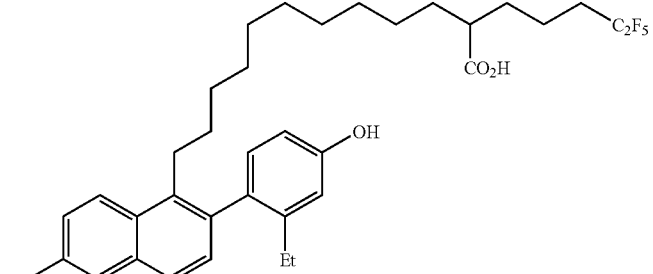 |
| 31 | 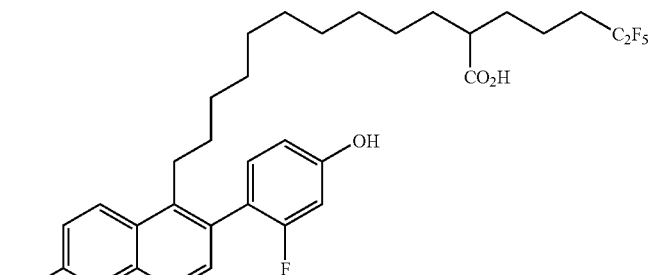 |
| 32 | 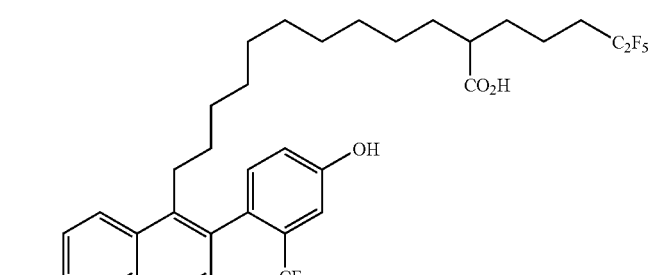 |
| 33 | 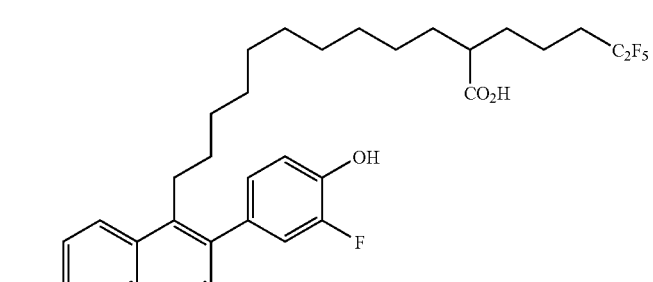 |
| 34 | 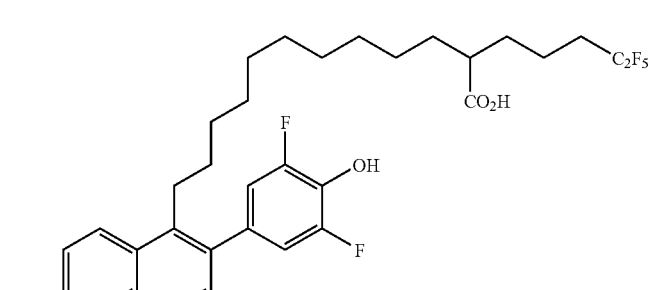 |

TABLE 1-continued
| Example No. | Chemical structure |
| --- | --- |
| 35 | 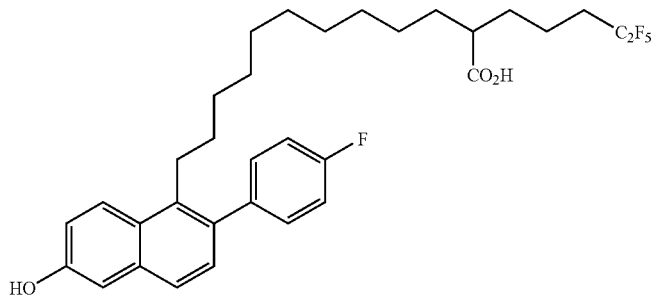 |
| 36 | 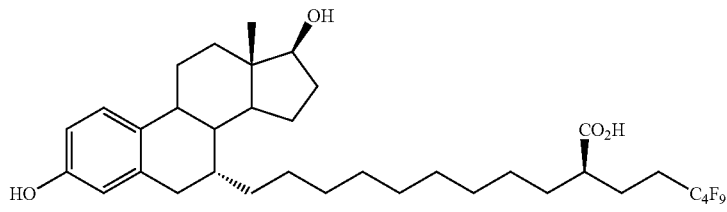 |
| 37 | 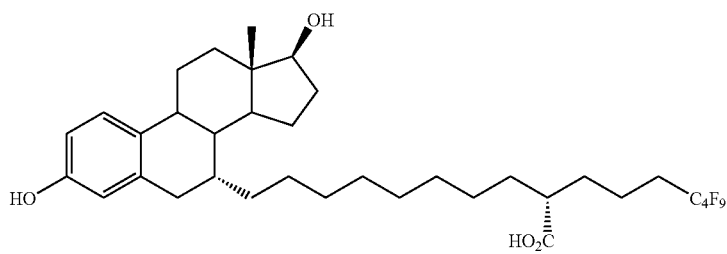 |
| 38 | 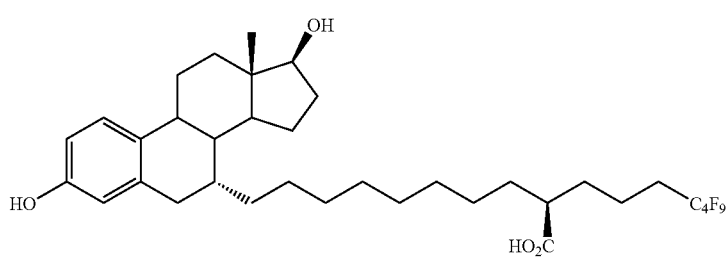 |
| 39 | 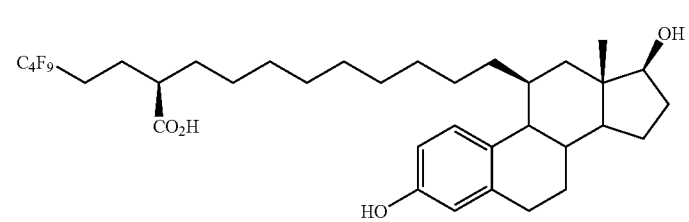 |

Example 1

Synthesis of 6-methoxy-2-(4-methoxyphenyl)-1-(2-propenyl)naphthalene (Step 1)

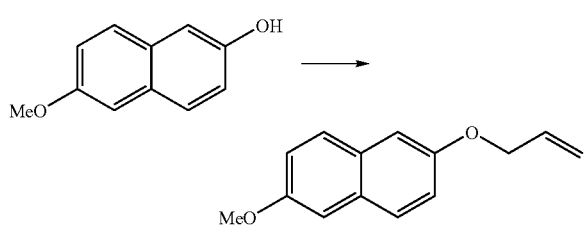

6-Methoxy-2-naphthol (22.1 g, 127.0 mmol) was dissolved in acetone (200 ml). Potassium carbonate (70.2 g, 508.0 mmol) and allyl bromide (16.5 ml, 191.0 mmol) were added to the resulting solution followed by stirring for 2 days at room temperature. After the reaction mixture was filtered, the organic solvent was distilled off under reduced pressure. Water was added to the residue, which was then extracted with ethyl acetate. The organic layer was washed with saturated aqueous sodium chloride and dried over anhydrous sodium sulfate. The organic solvent was distilled off again to give 6-methoxy-2-(2-propenyloxy)naphthalene (24.9 g, Yield 91%) as a crude product.

$^1$H-NMR(270 MHz, CDCl$_3$): δ 7.66–7.60 (m, 2H, Ar—H), 7.18–7.10 (m, 4H, Ar—H), 6.20–6.05 (m, 1H, CH$_2$=CHCH$_2$—), 5.45 (dd, J=18.8, 1.3 Hz, 1H, CH$_2$=CHCH$_2$—), 5.31 (dd, J10.5, 1.3 Hz, 1H, CH$_2$=CHCH$_2$—), 4.62 (d, J=5.3 Hz, 2H, CH$_2$=CHCH$_2$—), 3.90 (s, 3H, —OCH$_3$).

(Step 2)

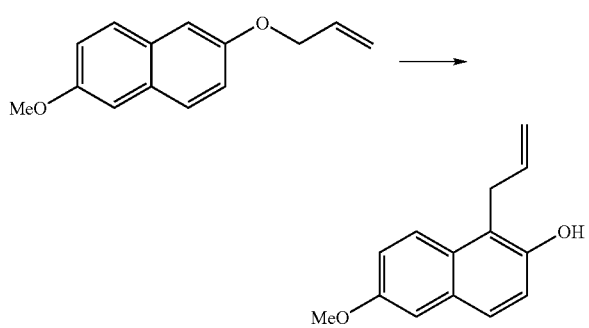

6-Methoxy-2-(2-propenyloxy)naphthalene (24.9 g, 116.2 mmol) was dissolved in N,N-dimethyl aniline (100 ml) followed by heating under reflux for 15 hours. After the organic solvent was distilled off under reduced pressure, 2N aqueous hydrochloric acid was added to the residue, which was then extracted with ethyl acetate. The organic layer was washed with saturated aqueous sodium chloride and dried over anhydrous sodium sulfate. After distilling off the solvent, the residue was purified by silica gel column chromatography (eluent: ethyl acetate/hexane=1/4), followed by recrystallization from ethyl acetate/hexane, to give 6-methoxy-1-(2-propenyl)-2-naphthol (20.3 g, Yield 82%).

$^1$H-NMR(270 MHz, CDCl$_3$): δ 7.80 (d, J=9.3 Hz, 1H, Ar—H), 7.56 (d, J=8.9 Hz, 1H, Ar—H), 7.16 (dd, J=9.3, 2.7 Hz, 1H, Ar—H), 7.11 (d, J=2.7 Hz, 1H, Ar—H), 7.07 (d, J=8.9 Hz, 1H, Ar—H), 6.13–5.98 (m, 1H, CH$_2$=CHCH$_2$—), 5.10 (dd, J=10.0, 1.3 Hz, 1H, CH$_2$=CHCH$_2$—), 5.04 (dd, J=17.5, 1.3 Hz, 1H, CH$_2$=CHCH$_2$—), 4.93 (s, 1H, —OH), 3.90 (s, 3H, —OCH$_3$), 3.79 (d, J=5.9 Hz, 2H, CH$_2$=CHCH$_2$—).

(Step 3)

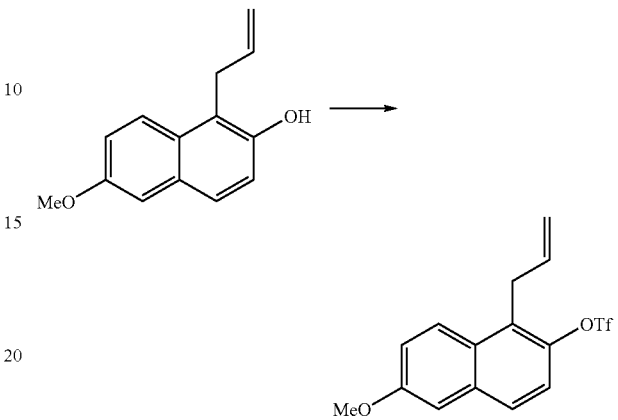

6-Methoxy-1-(2-propenyl)-2-naphthol (18.77 g, 87.6 mmol) was dissolved in dichloromethane (300 ml). To this solution, pyridine (21.3 ml, 262.8 mmol) and trifluoromethanesulfonic anhydride (22.1 ml, 131.4 mmol) were added dropwise at 0° C., and the resulting mixture was stirred for 30 minutes. After the reaction was completed, water was added at 0° C. to the reaction mixture, which was then extracted with ethyl acetate. The organic layer was washed with dilute hydrochloric acid and saturated aqueous sodium chloride, and then dried over anhydrous sodium sulfate. After distilling off the solvent, the residue was purified by silica gel column chromatography (eluent: ethyl acetate/hexane=1/9) to give 6-methoxy-1-(2-propenyl)-2-naphthyl trifluoromethanesulfonate (30.8 g, Yield 100%).

$^1$H-NMR(270 MHz, CDCl$_3$): δ 7.95 (d, J=9.3 Hz, 1H, Ar—H), 7.69 (d, J=8.9 Hz, 1H, Ar—H), 7.35 (d, J=8.9 Hz, 1H, Ar—H), 7.25 (dd, J=9.3, 2.7 Hz, 1H, Ar—H), 7.17 (d, J=2.7 Hz, 1H, Ar—H), 6.07–5.94 (m, 1H, CH$_2$=CHCH$_2$—), 5.10 (dd, J=10.0, 1.3 Hz, 1H, CH$_2$=CHCH$_2$—), 5.02 (dd, J=17.2, 1.3 Hz, 1H, CH$_2$=CHCH$_2$—), 3.93 (s, 3H, —OCH$_3$), 3.89 (d, J=5.6 Hz, 2H, CH$_2$=CHCH$_2$—).

(Step 4)

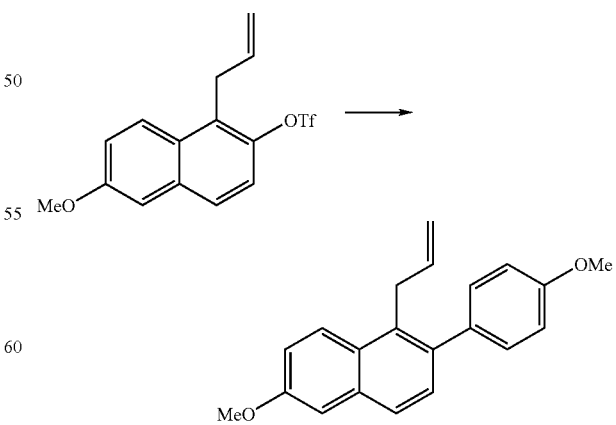

4-Methoxyphenylboronic acid (10.15 g, 66.8 mmol), tripotassium phosphate hydrate (77.6 g, 278.3 mmol) and tetrakis(triphenylphosphine)palladium(0)(1.93 g, 1.67 mmol, 3 mol %) were added to a solution of 6-methoxy-1-(2-propenyl)-2-naphthyl trifluoromethanesulfonate (19.3 g, 55.66 mmol) in dioxane (300 ml), followed by heating under reflux for 8 hours under argon atmosphere. Water was added to the reaction mixture, which was then extracted with ethyl acetate, washed with saturated aqueous sodium chloride, and dried over anhydrous sodium sulfate. After distilling off the solvent, the residue was purified by silica gel column chromatography (eluent: ethyl acetate/hexane=1/9), followed by recrystallization from hexane, to give 6-methoxy-2-(4-methoxyphenyl)-1-(2-propenyl)naphthalene (12.65 g, Yield 75%).

$^1$H-NMR(270 MHz, CDCl$_3$): δ 7.95 (d, J=9.8 Hz, 1H, Ar—H), 7.65 (d, J=8.5 Hz, 1H, Ar—H), 7.35 (d, J=8.9 Hz, 1H, Ar—H), 7.34–7.16 (m, 4H, Ar—H), 6.96 (d, J=8.6 Hz, 2H, Ar—H), 6.16–6.02(m, 1H, CH$_2$=CHCH$_2$—), 5.06 (dd, J=10.2, 1.6 Hz, 1H, CH$_2$=CHCH$_2$—), 4.83 (dd, J=17.2, 1.6 Hz, 1H, CH$_2$=CHCH$_2$—), 3.94 (s, 3H, —OCH$_3$), 3.87 (s, 3H, —OCH$_3$), 3.73 (d, J=5.3 Hz, 2H, CH$_2$=CHCH$_2$—).

Example 2

Synthesis of diethyl 2-(5-hexenyl)-2-(4,4,5,5,5-pentafluoropentyl)malonate

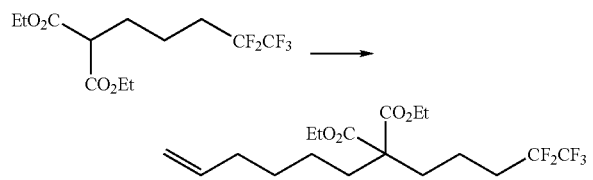

A solution of diethyl 2-(4,4,5,5,5-pentafluoropentyl)malonate (4.0 g, 12.5 mmol) in dimethyl sulfoxide (30 ml) was cooled to 10° C. To this solution, 60% sodium hydride (600 mg, 15 mmol) was added, and the resulting mixture was stirred for 1 hour at room temperature. 6-Bromo-1-hexene (2.5 ml, 18.75 mmol) was slowly added dropwise to the reaction mixture, followed by stirring for 3 hours at room temperature. Water was added to the reaction mixture, which was then extracted with ethyl acetate. The organic layer was washed with water and saturated aqueous sodium chloride, and then dried over anhydrous sodium sulfate. After distilling off the solvent, the residue was purified by silica gel column chromatography (eluent: ethyl acetate/hexane=1/9) to give diethyl 2-(5-hexenyl)-2-(4,4,5,5,5-pentafluoropentyl)malonate (3.86 g, Yield 77%).

$^1$H-NMR(270 MHz, CDCl$_3$): δ 5.82–5.72 (m, 1H, —CH=CH$_2$), 5.02–4.92 (m, 2H, —CH=CH$_2$), 4.19 (q, J=7.3 Hz, 4H, —CO$_2$CH$_2$CH$_3$), 2.10–1.86 (m, 8H), 1.53–1.34 (m, 6H), 1.26 (t, J=7.3 Hz, 6H, —CO$_2$CH$_2$CH$_3$).

Example 3

Synthesis of 9-[6-hydroxy-2-(4-hydroxyphenyl)naphth-1-yl]-2-(4,4,5,5,5-pentafluoropentyl)nonanoic acid (Step 1)

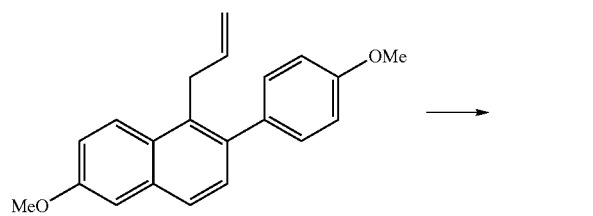

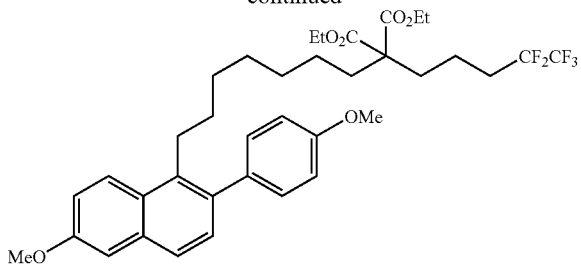

The diethyl 2-(5-hexenyl)-2-(4,4,5,5,5-pentafluoropentyl)-malonate prepared in Example 2 (1.83 g, 4.55 mmol) and benzylidene-bis(tricyclohexylphosphine)dichlororuthenium (94 mg, 0.11 mmol) were added to a solution of 6-methoxy-2-(4-methoxyphenyl)-1-(2-propenyl)naphthalene (692 mg, 2.28 mmol) in dichloromethane (10 ml), followed by heating under reflux for 20 hours under argon atmosphere. After distilling off the solvent, the residue was purified by silica gel flash column chromatography (eluent: hexane/ethyl acetate=10/1) to give the desired olefin (1.8 g) as a mixture of cis- and trans-forms and side chain dimer. This mixture was dissolved in ethyl acetate (20 ml), and 10% palladium carbon (236 mg) was added to the resulting solution followed by stirring for 2 hours at room temperature under hydrogen atmosphere. The catalyst was removed by filtration and the solvent was distilled off under reduced pressure. The residue was purified by silica gel flash column chromatography (eluent: hexane/ethyl acetate=4/1) to give diethyl 2-[7-[6-methoxy-2-(4-methoxyphenyl)napht-1-yl]heptyl]-2-(4,4,5,5,5-pentafluoropentyl)malonate (1.05 g, Yield 68%).

$^1$H-NMR (270 MHz, CDCl$_3$) δ: 7.96 (d, J=9.3 Hz, 1H, Ar—H), 7.59 (d, J=8.2 Hz, 1H, Ar—H), 7.30–7.21 (m, 4H, Ar—H), 7.18–7.15 (m, 1H, Ar—H), 6.97 (d, J=8.6 Hz, 2H, Ar—H), 4.18 (q, J=7.0 Hz, 4H, —CO$_2$CH$_2$CH$_3$), 3.94 (s, 3H, —OCH$_3$), 3.88 (s, 3H, —OCH$_3$), 2.97–2.91 (m, 2H, naphtyl-CH$_2$—), 2.09–2.03 (m, 2H, —CH$_2$CF$_2$), 1.99–1.82 (m, 4H, alkyl-H), 1.55–1.45(m, 6H, alkyl-H), 1.23(t, J=7.0 Hz, 6H, —CO$_2$CH$_2$CH$_3$), 1.10–1.04(m, 6H, alkyl-H).

(Step 2)

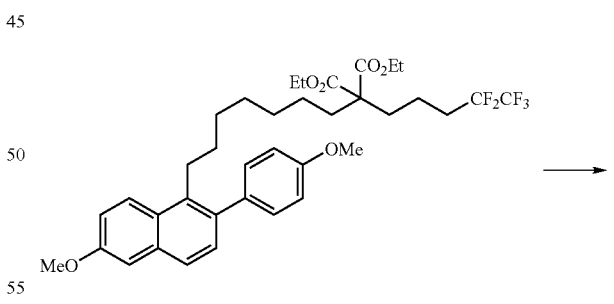

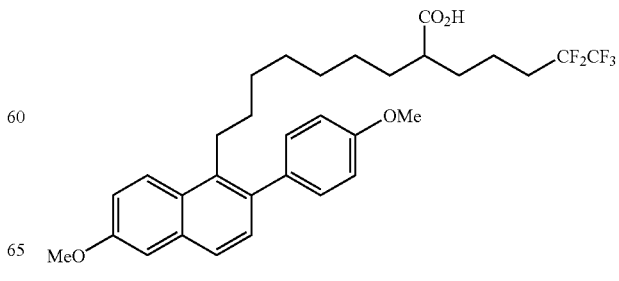

Diethyl 2-[7-[6-methoxy-2-(4-methoxyphenyl)napht-1-yl]heptyl]-2-(4,4,5,5,5-pentafluoropentyl)malonate (1.02 g, 1.5 mmol) was dissolved in ethanol (10 ml). To this solution, sodium hydroxide (1.2 g, 30 mmol) and water (1 ml) were added, and the resulting mixture was heated under reflux for 3 hours. Dilute hydrochloric acid was added to the reaction mixture, which was then extracted with ethyl acetate. The organic layer was washed with saturated aqueous sodium chloride and dried over anhydrous sodium sulfate. The solvent was distilled off to give 2-[7-[6-methoxy-2-(4-methoxyphenyl)napht-1-yl]heptyl]-2-(4,4,5,5,5-pentafluoropentyl)malonic acid (1.0 g).

Next, the resulting 2-[7-[6-methoxy-2-(4-methoxyphenyl)napht-1-yl]heptyl]-2-(4,4,5,5,5-pentafluoropentyl)-malonic acid (1.0 g) was dissolved in dimethyl sulfoxide (10 ml) and the mixture was heated for 4 hours at 120° C. Water was added to the reaction mixture, which was then extracted with ethyl acetate. The organic layer was washed with saturated aqueous sodium chloride and dried over anhydrous sodium sulfate. After distilling off the solvent, the residue was purified by silica gel column chromatography (eluent: ethyl acetate/hexane=1/1) to give 9-[6-methoxy-2-(4-methoxyphenyl)naphth-1-yl]-2-(4,4,5,5,5-pentafluoropentyl) nonanoic acid (820 mg, Yield 94%).

$^1$H-NMR(270 MHz, CDCl$_3$): δ 7.97 (d, J=8.9 Hz, 1H, Ar—H), 7.59 (d, J=8.2 Hz, 1H, Ar—H), 7.30–7.21 (m, 4H, Ar—H), 7.18–7.15 (m, 1H, Ar—H), 6.97 (d, J=8.6 Hz, 2H, Ar—H), 3.94 (s, 3H, OCH$_3$), 3.88 (s, 3H, —OCH$_3$), 2.97–2.91 (m, 2H, naphtyl-CH$_2$—), 2.38–2.35(m, 1H, —CHCO$_2$), 2.09–1.94 (m, 2H, —CH$_2$CF$_2$), 1.73–1.41(m, 8H, alkyl-H), 1.29–1.18(m, 8H, alkyl-H).

(Step 3)

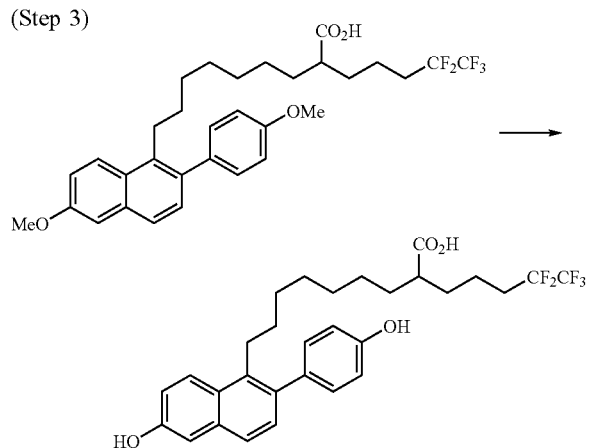

A solution of boron tribromide in dichloromethane (1.0 M, 8.5 ml, 8.47 mmol) was added dropwise to a solution of 9-[6-methoxy-2-(4-methoxyphenyl)naphth-1-yl]-2-(4,4,5,5,5-pentafluoropentyl)nonanoic acid (820 mg, 1.41 mmol) in dichloromethane (20 ml) at −78° C. under argon atmosphere. The reaction mixture was warmed with stirring to 0° C. over 5 hours. Water was added to the reaction mixture, which was then extracted with ethyl acetate. The organic layer was washed with water and saturated aqueous sodium chloride, and then dried over anhydrous magnesium sulfate. After distilling off the solvent, the residue was purified by silica gel column chromatography (eluent: ethyl acetate/hexane=3/2), followed by column chromatography on reversed-phase silica gel RP-18 (eluent: acetonitrile containing 0.1% trifluoroacetic acid/water=3/2), to give 9-[6-hydroxy-2-(4-hydroxyphenyl)naphth-1-yl]-2-(4,4,5,5,5-pentafluoropentyl)nonanoic acid (633 mg, Yield 81%).

$^1$H-NMR(270 MHz, CD$_3$OD): δ 7.93 (d, J=9.9 Hz, 1H, Ar—H), 7.47 (d, J=8.2 Hz, 1H, Ar—H), 7.18–7.11 (m, 5H, Ar—H), 6.85 (d, J=9.3 Hz, 2H, Ar—H), 2.97–2.91 (m, 2H, naphtyl-CH$_2$—), 2.34–2.29 (m, 1H, —CHCO$_2$), 2.20–1.99 (m, 2H, —CH$_2$CF$_2$), 1.62–1.41 (m, 6H, alkyl-H), 1.27–1.18 (m, 10H, alkyl-H).

Example 4

Synthesis of 11-[6-hydroxy-2-(4-hydroxyphenyl)naphth-1-yl]-2-(4,4,5,5,5-pentafluoropentyl)undecanoic acid

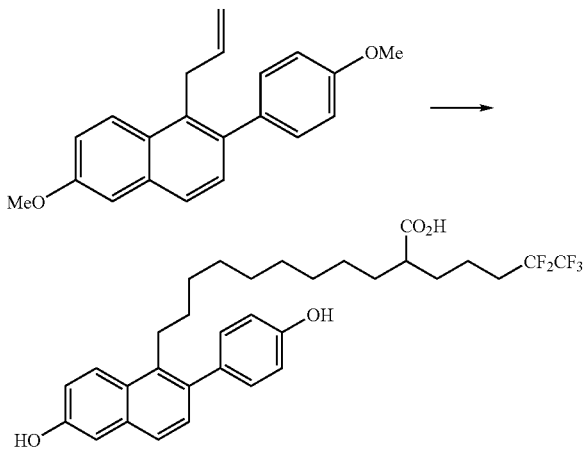

The same procedures as shown in Examples 1, 2 and 3 were repeated to give 11-[6-hydroxy-2-(4-hydroxyphenyl)naphth-1-yl]-2-(4,4,5,5,5-pentafluoropentyl)undecanoic acid.

$^1$H-NMR (270 MHz, CDCl$_3$): δ 7.98(d, 1H), 7.54(d, 1H), 7.33–7.03(m, 5H), 6.88(d, 2H), 2.93(t, 2H), 2.5(m, 1H), 2.2–1.0(m, 22H)

Example 5

Synthesis of 10-[(1RS,2RS)-6-hydroxy-2-(4-hydroxyphenyl)-2-methyl-1,2,3,4-tetrahydro-1-naphthyl]-2-(4,4,5,5,5-pentafluoropentyl)decanoic acid (Step 1)

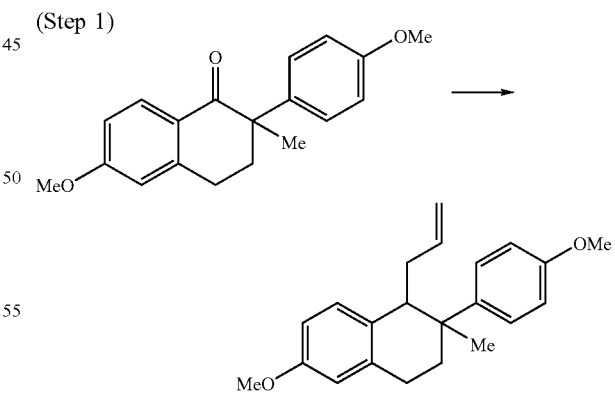

6-Methoxy-2-(4-methoxyphenyl)-2-methyl-1,2,3,4-tetrahydro-naphthalen-1-one was synthesized by the method described in U.S. Pat. No. 4,904,661. A solution of this compound (1.5 g, 5.1 mmol) as dissolved in anhydrous tetrahydrofuran (25 ml) was added dropwise to a solution of lithium aluminum hydride in anhydrous tetrahydrofuran (1M in THF, 2.6 ml, 2.6 mmol) at −78° C. under argon atmosphere. The reaction was continued for 1.5 hours. The reaction mixture was then warmed slowly to room temperature and stirred for 8 hours. Saturated aqueous ammonium chloride was added to the reaction mixture, which was then extracted with ethyl acetate. The organic layer was washed with saturated aqueous sodium bicarbonate, water and saturated aqueous sodium chloride, dried over anhydrous magnesium sulfate, and then evaporated to remove the solvent. The resulting residue was dissolved in 1,2-dichloroethane (35 ml). To this solution, zinc iodide (2.02 g, 6.31 mmol) and allyltrimethylsilane (1.67 ml, 10.52 mmol) were added at 0° C. under argon atmosphere, and the resulting mixture was stirred for 12 hours at room temperature. Water was added to the reaction mixture, which was then extracted with dichloromethane. The organic layer was washed with saturated aqueous sodium bicarbonate, water and saturated aqueous sodium chloride, and then dried over anhydrous magnesium sulfate. After distilling off the solvent, the residue was purified by silica gel flash column chromatography (eluent: hexane/ethyl acetate=60/1) to give (1RS, 2RS)-6-methoxy-2-(4-methoxyphenyl)-2-methyl-1-(2-propenyl)-1,2,3,4-tetrahydronaphthalene (1.27 g, Yield 78%).

$^1$H-NMR (300 MHz, CDCl$_3$): δ 7.31(d, 2H, J=7.5 Hz), 6.97(d, 1H, J=7.9 Hz), 6.88(d, 2H, J=8.7 Hz), 6.68–6.65(m, 2H), 5.53(m, 1H), 4.76–4.57(m, 2H), 3.81(s, 3H), 3.78(s, 3H), 2.99–2.78(m, 2H), 2.81(m, 1H), 2.28(m, 1H), 1.98–1.92(m, 2H), 1.71(m, 1H), 1.17(s, 3H).

(Step 2)

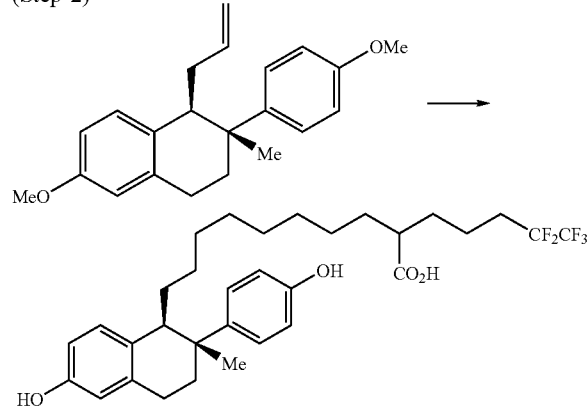

The (1RS,2RS)-6-methoxy-2-(4-methoxyphenyl)-2-methyl-1-(2-propenyl)-1,2,3,4-tetrahydronaphthalene thus prepared was converted into 10-[(1RS,2RS)-6-hydroxy-2-(4-hydroxyphenyl)-2-methyl-1,2,3,4-tetrahydro-1-naphthyl]-2-(4,4,5,5,5-pentafluoropentyl)decanoic acid by a procedure analogous to Example 3.

$^1$H-NMR (300 MHz, CDCl$_3$): δ 7.23(d, 2H, J=7.5 Hz), 6.90(d, 1H, J=7.9 Hz), 6.80(d, 2H, J=8.7 Hz), 6.58(m, 2H), 2.90(m, 2H), 2.60(d, 1H, J=8.7 Hz), 2.37(m, 1H), 2.22(m, 1H), 2.02(m, 2H), 1.87(m, 1H), 1.37–1.75(m, 6H), 0.86–1.26(m, 17H).

Mass (ESI): 585(M+1).

Example 6

Synthesis of 2-[5-[4-[(6-hydroxy-2-(4-hydroxyphenyl)benzo-[b]thiophen-3-yl)carbonyl]phenoxy]pentyl]-6,6,7,7,7-pentafluoroheptanoic acid (Step 1)

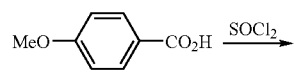

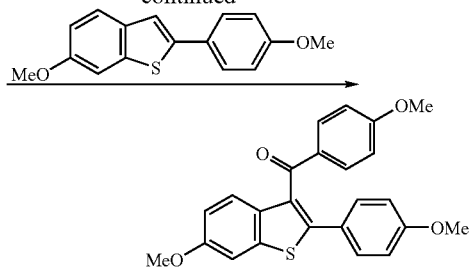

4-Methoxybenzoic acid (450 mg, 2.96 mmol), thionyl chloride (3 ml, 44.4 mmol) and anhydrous dimethylformamide (1 drop) were added to anhydrous chloroform (10 ml), and the resulting mixture was refluxed for 3 hours under argon atmosphere and then cooled to room temperature. After the reaction mixture was concentrated under reduced pressure, the residue was dissolved in anhydrous dichloromethane, and 6-methoxy-2-(4-methoxyphenyl)benzo[b]thiophene (760 mg, 2.8 mmol) synthesized by the method described in J. Med. Chem. 1057(1984) and aluminum chloride (2.37 g, 17.76 mmol) were added to the resulting solution followed by stirring for 4 hours at room temperature. Tetrahydrofuran and ice were added to stop the reaction and the reaction mixture was extracted with ethyl acetate. The organic layer was washed with water and saturated aqueous sodium chloride, and then dried over anhydrous magnesium sulfate. After distilling off the solvent, the filtrate was concentrated under reduced pressure and the resulting residue was purified by silica gel column chromatography (eluent: dichloromethane/hexane=1/1) to give [6-methoxy-2-(4-methoxyphenyl)benzo[b]thiophen-3-yl](4-methoxy-phenyl)-methanone (405 mg, Yield 39%) as a yellow oil.

$^1$H-NMR(300 MHz, CDCl$_3$): δ 7.80–7.75 (m, 2H), 7.52 (d, 1H, J=8.6 Hz), 7.37–7.28 (m, 3H), 6.95 (dd, 1H, J$_1$=8.9 Hz, J$_2$=2.2 Hz), 6.78–6.74 (m, 4H), 3.91 (s, 3H), 3.85 (s, 3H), 3.77 (s, 3H).

(Step 2)

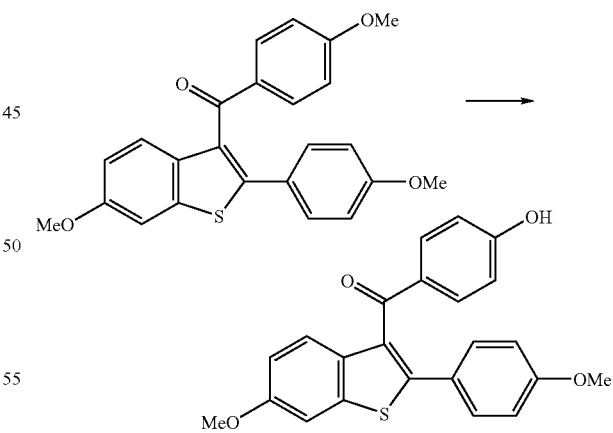

[6-Methoxy-2-(4-methoxyphenyl)benzo[b]thiophen-3-yl](4-methoxyphenyl)methanone (410 mg, 1.02 mmol) was dissolved in anhydrous dimethylformamide (15 ml), and sodium ethanethiolate (170 mg, 2.04 mmol) was added to the resulting solution followed by stirring for 1.5 hours at a temperature of 90° C. to 100° C. under argon atmosphere. The reaction mixture was cooled to room temperature and, after addition of water, was extracted with ethyl acetate. The organic layer was washed with water and saturated aqueous sodium chloride, and then dried over anhydrous magnesium sulfate. After distilling off the solvent, the residue was purified by silica gel column chromatography (eluent: ethyl acetate/hexane=1/1) to give (4-hydroxyphenyl)[6-methoxy-2-(4-methoxyphenyl)benzo[b]thiophen-3-yl]methanone (323 mg, Yield 81.6%) as a yellow oil.

$^1$H-NMR(300 MHz, CDCl$_3$): δ 7.70 (d, 2H, J=9.0), 7.51 (d, 1H, J=8.7), 7.33–7.26 (m, 3H), 6.95 (dd, 1H, J$_1$=8.9 Hz, J$_2$=2.6 Hz), 6.75–6.65 (m, 4H), 3.87 (s, 3H), 3.72 (s, 3H).

(Step 3)

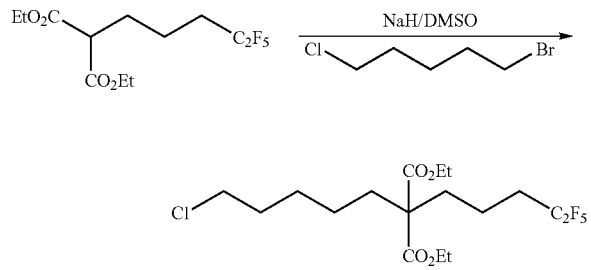

Diethyl 2-(4,4,5,5,5-pentafluoropentyl)malonate (3 g, 9.37 mmol) was dissolved in dimethyl sulfoxide (20 ml), and sodium hydride (60%, 525 mg, 13.11 mmol) was added to the resulting solution followed by stirring for 1 hour at room temperature. 5-Bromo-1-chloropentane (7.4 ml, 56.2 mmol) was added to the reaction mixture, followed by stirring for 1.5 hours at room temperature. The reaction mixture was diluted with water, extracted with ethyl acetate, washed with water and saturated aqueous sodium chloride, and then dried over anhydrous magnesium sulfate. The filtrate was concentrated under reduced pressure and the resulting residue was purified by silica gel column chromatography (eluent: dichloromethane/hexane=1/4) to give diethyl 2-(5-chloropentyl)-2-(4,4,5,5,5-pentafluoropentyl)malonate (3.3 g, Yield 83%) as a colorless oil.

$^1$H-NMR (300 MHz, CDCl$_3$): δ 4.14 (q, 4H, J=7.1 Hz), 3.46(t, 2H, J=6.7 Hz), 2.06–1.64(m, 8H), 1.50–1.36(m, 4H), 1.24–1.10(m, 2H), 1.21(t, 6H, J=7.1 Hz).

(Step 4)

(4-Hydroxyphenyl)[6-methoxy-2-(4-methoxyphenyl)benzo-[b]thiophen-3-yl]methanone (1 g, 2.56 mmol) was dissolved in dimethylformamide (15 ml), and sodium hydride (60%, 143 mg, 3.59 mmol) was added to the resulting solution followed by stirring for 1 hour at room temperature.

Diethyl 2-(5-chloropentyl)-2-(4,4,5,5,5-pentafluoropentyl)-malonate (1.85 g, 4.35 mmol), sodium iodide (769 mg, 5.13 mmol) and tetrabutylammonium iodide (189 mg, 0.51 mmol) were added to the reaction mixture followed by stirring for 24 hours at 60° C. After the reaction mixture was cooled to room temperature, saturated aqueous ammonium chloride was added to the reaction mixture, which was then extracted with ethyl acetate, dried over anhydrous magnesium sulfate and filtered. The filtrate was concentrated under reduced pressure and the resulting residue was purified by silica gel column chromatography (eluent: ethyl acetate/hexane=1/9) to give diethyl 2-[5-[4-[(6-methoxy-2-(4-methoxyphenyl)benzo[b]thiophen-3-yl)-carbonyl]-phenoxy]pentyl]-2-(4,4,5,5,5-pentafluoropentyl)malonate (1.4 g, Yield 70%) as a yellow oil.

$^1$H-NMR (300 MHz, CDCl$_3$): δ 7.73(d, 2H, J=9.1 Hz), 7.48(d, 1H, J=8.5 Hz), 7.32(d, 2H, J=8.6 Hz), 7.27(d, 1H, J=2.3 Hz), 6.91(dd, 1H, J$_1$=8.8 Hz, J$_2$=2.3 Hz), 6.74–6.67 (m, 4H), 4.15(q, 4H, J=7.1 Hz), 3.88(t, 2H, J=6.3 Hz), 3.83(s, 3H), 3.70(s, 3H), 2.08–1.82(m, 6H), 1.75–1.71(m, 2H), 1.53–1.37(m, 6H), 1.21(t, 6H, J=7.1 Hz).

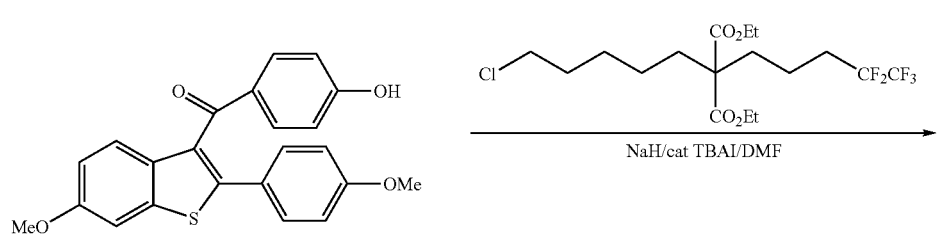

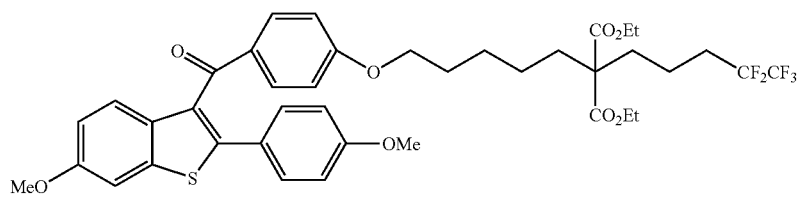

(Step 5)

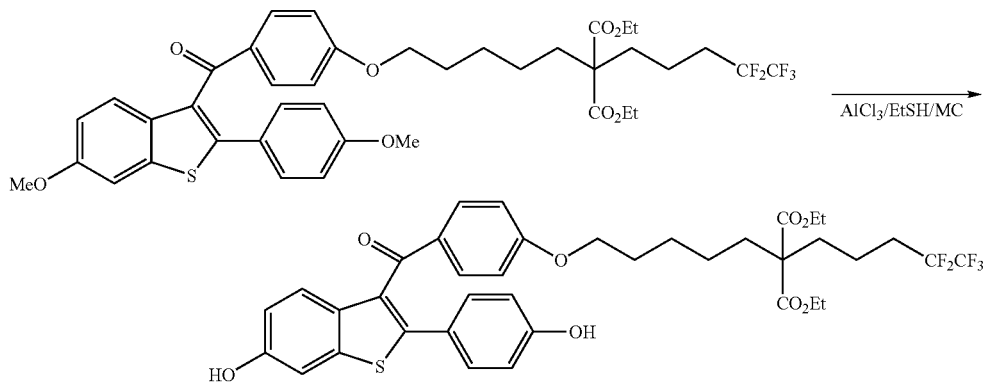

Diethyl 2-[5-[4-[(6-methoxy-2-(4-methoxyphenyl)benzo-[b]thiophen-3-yl)carbonyl]phenoxy]pentyl]-2-(4,4,5,5,5-pentafluoropentyl)malonate (1.58 g, 2.03 mmol) was dissolved in dichloromethane (40 ml), and aluminum chloride (1.62 g, 12.2 mmol) and ethanethiol (0.25 ml, 10.15 mmol) were added to the resulting solution followed by stirring for 1.5 hours at room temperature. After the reaction mixture was cooled to 0° C., tetrahydrofuran (30 ml) was slowly added to the reaction mixture, which was then diluted with water and extracted with ethyl acetate. The organic layer was washed with saturated aqueous sodium chloride, dried over anhydrous magnesium sulfate, and then filtered. The filtrate was concentrated under reduced pressure and the resulting residue was purified by silica gel column chromatography (eluent: ethyl acetate/hexane=1/2) to give diethyl 2-[5-[4-[(6-hydroxy-2-(4-hydroxyphenyl)benzo[b]thiophen-3-yl)carbonyl]phenoxy]pentyl]-2-(4,4,5,5,5-pentafluoropentyl)malonate (1.2 g, Yield 79%) as a brown foam.

$^1$H-NMR (300 MHz, CDCl$_3$): δ 7.73(d, 2H, J=9.1 Hz), 7.38(d, 1H, J=8.6 Hz), 7.18(d, 1H, J=2.3 Hz), 7.14(d, 2H, J=8.6 Hz), 6.79(dd, 1H, J$_1$=8.6 Hz, J$_2$=2.3Hz), 6.72(d, 2H, J=9.1 Hz), 6.57(d, 2H, J=8.6 Hz), 4.17(q, 4H, J=7.2 Hz), 3.91(t, 2H, J=6.1 Hz), 2.10–1.78(m, 6H), 1.74–1.68(m, 2H), 1.54–1.36(m, 4H), 1.26–1.13 (m, 2H), 1.21(t, 6H, J=7.2 Hz).

(Step 6)

Diethyl 2-[5-[4-[(6-hydroxy-2-(4-hydroxyphenyl)benzo-[b]thiophen-3-yl)carbonyl]phenoxy]pentyl]-2-(4,4,5,5,5-pentafluoropentyl)malonate (1.197 g, 1.59 mmol) was dissolved in ethanol (20 ml), and potassium hydroxide (3.58 g, 63.8 mmol) dissolved in water (10 ml) was then added. After stirring for 24 hours at 80° C., the reaction mixture was cooled to room temperature, concentrated under reduced pressure to remove ethanol, adjusted to pH 3 with 3N aqueous hydrochloric acid, and then extracted with ethyl acetate. The organic layer was dried over anhydrous magnesium sulfate and filtered. The filtrate was concentrated under reduced pressure to give 2-[5-[4-[(6-hydroxy-2-(4-hydroxyphenyl)benzo-[b]thiophen-3-yl)carbonyl]phenoxy]pentyl]-2-(4,4,5,5,5-pentafluoropentyl)malonic acid (1.1 g) as a brown product, which was then used for the subsequent reaction without further purification.

$^1$H-NMR (300 MHz, CD$_3$OD): δ 7.68(d, 2H, J=9.0 Hz), 7.38(d, 1H, J=9.0 Hz), 7.24(d, 1H, J=2.0 Hz), 7.18(d, 2H, J=8.6 Hz), 6.85(dd, 1H, J$_1$=9.0 Hz, J$_2$=2.0 Hz), 6.80(d, 2H, J=8.6 Hz), 6.63(d, 2H, J=8.6 Hz), 3.95(t, 2H, J=6.0 Hz), 2.21–1.80(m, 6H), 1.74–1.70(m, 2H), 1.58–1.21(m, 6H).

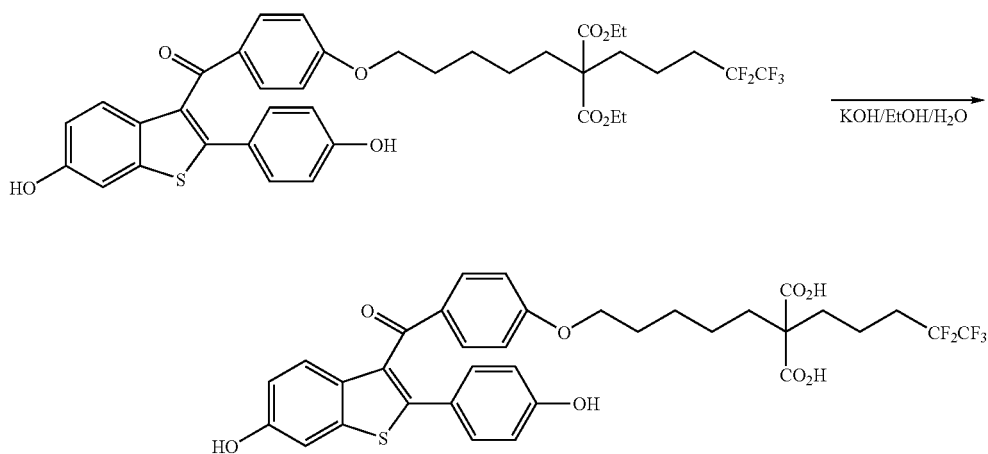

(Step 7)

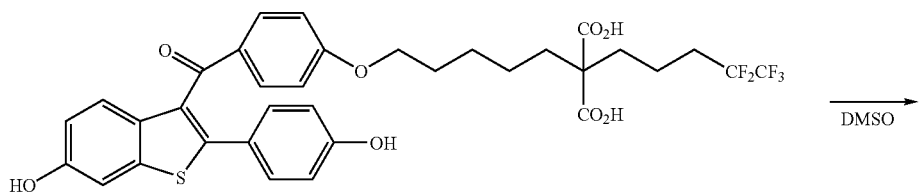

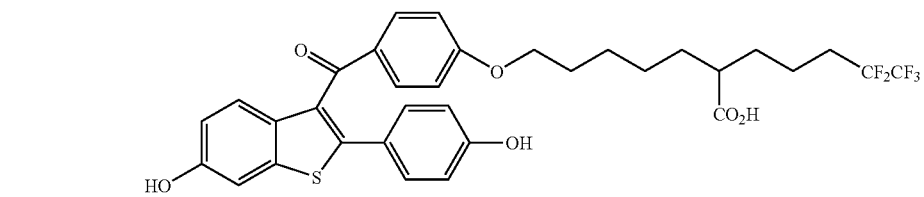

2-[5-[4-[(6-Hydroxy-2-(4-hydroxyphenyl)benzo[b]thiophen-3-yl)carbonyl]-phenoxy]pentyl]-2-(4,4,5,5,5-pentafluoropentyl)malonic acid (1.1 g, 1.58 mmol) was dissolved in dimethyl sulfoxide (10 ml) and stirred for 3 hours at 120° C. The reaction mixture was cooled to room temperature, diluted with water, and then extracted with ethyl acetate. The organic layer was dried over anhydrous magnesium sulfate and filtered. The filtrate was concentrated under reduced pressure and the resulting residue was purified by silica gel column chromatography (eluent: ethyl acetate/hexane=1/1) to give 2-[5-[4-[(6-hydroxy-2-(4-hydroxyphenyl)benzo[b]thiophen-3-yl)carbonyl]phenoxy]pentyl]-6,6,7,7,7-pentafluoroheptanoic acid (732 mg, Yield 71%) as a yellow solid.

$^1$H-NMR (300 MHz, CD$_3$OD): δ 7.68(d, 2H, J=8.8 Hz), 7.38(d, 1H, J=8.8 Hz), 7.25(d, 1H, J=2.3 Hz), 7.18(d, 2H, J=8.6 Hz), 6.85(dd, 1H, J$_1$=8.8 Hz, J$_2$=2.3 Hz), 6.79(d, 2H, J=8.9 Hz), 6.63(d, 2H, J=8.6 Hz), 3.95(t, 2H, J=6.5 Hz), 2.85(m, 1H), 2.15–1.94(m, 2H), 1.78–1.29(m, 12H).

Mass (ESI): 651(M+1).

Example 7

Synthesis of 8-[4-[(6-hydroxy-2-(4-hydroxyphenyl)benzo[b]thiophen-3-yl)carbonyl]phenoxy]-2-(4,4,5,5,5-pentafluoropentyl)octanoic acid

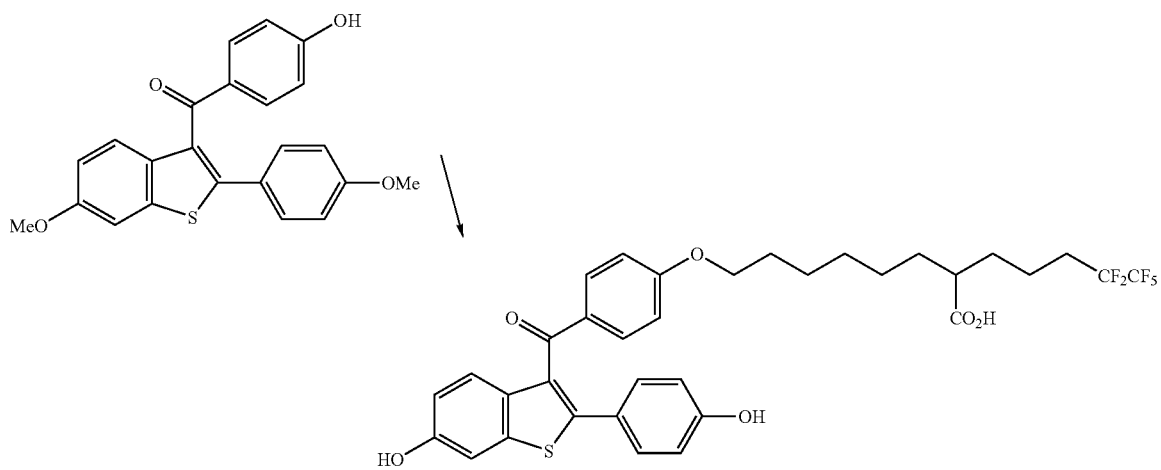

The same procedure as shown in Example 1 was repeated to give 8-[4-[(6-hydroxy-2-(4-hydroxyphenyl)benzo[b]thiophen-3-yl)carbonyl]phenoxy]-2-(4,4,5,5,5-pentafluoropentyl)octanoic acid.

$^1$H-NMR(300 MHz, CDCl$_3$): δ 7.68 (d, 2H, J=8.6 Hz), 7.38 (d, 1H, J=8.7 Hz), 7.24–7.16 (m, 3H), 6.86–6.78 (m, 3H), 6.62 (d, 2H, J=8.3 Hz), 3.95 (t, 2H, J=6.4 Hz), 2.35 (m, 1H), 2.15–1.95 (m, 2H), 1.77–1.25 (1m, 4H).

Mass(ESI): 665 (M+1).

Example 8

Synthesis of 2-[2-[4-[(6-hydroxy-2-(4-hydroxyphenyl)benzo-[b]thiophen-3-yl)carbonyl]-phenoxy]ethyl]-6,6,7,7,7-pentafluoroheptanoic acid

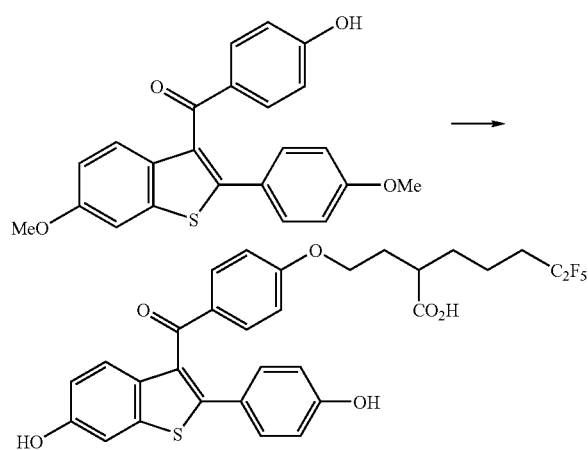

The same procedure as shown in Example 1 was repeated to give 2-[2-[4-[(6-hydroxy-2-(4-hydroxyphenyl)benzo[b]thiophen-3-yl)carbonyl]phenoxy]ethyl]-6,6,7,7,7-pentafluoroheptanoic acid.

$^1$H-NMR (300 MHz, CDCl$_3$+CD$_3$OD): δ 7.70(d, 2H, J=8.9 Hz), 7.50(d, 1H, J=8.8 Hz), 7.26(d, 1H, J=2.2 Hz), 7.20(d, 2H, J=8.6 Hz) 6.90 (dd, 1H, J$_1$=8.8 Hz, J$_2$=2.2 Hz), 6.70(d, 2H, J=8.9 Hz), 6.65(d, 2H, J=8.6 Hz), 4.10–3.90(m, 2H), 2.58(m, 1H), 2.18–1.84(m, 4H), 1.82–1.52(m, 4H).

Example 9

Synthesis of 2-[3-[4-[(6-hydroxy-2-(4-hydroxyphenyl)benzo-[b]thiophen-3-yl)carbonyl]-phenoxy]propyl]-6,6,7,7,7-pentafluoroheptanoic acid

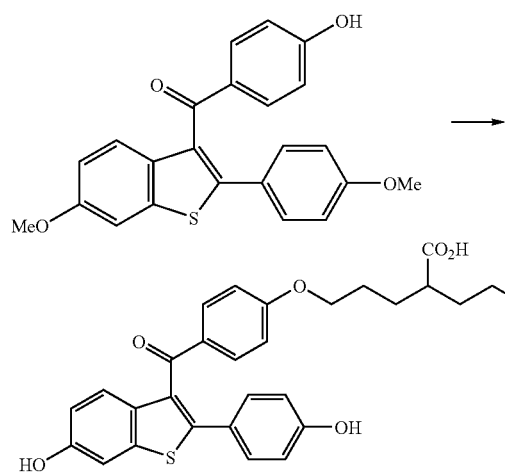

The same procedure as shown in Example 1 was repeated to give 2-[3-[4-[(6-hydroxy-2-(4-hydroxyphenyl)benzo[b]thiophen-3-yl)carbonyl]phenoxy]propyl]-6,6,7,7,7-pentafluoroheptanoic acid.

$^1$H-NMR (300 MHz, CDCl$_3$): δ 7.73(d, 2H, J=8.8 Hz), 7.47(d, 1H, J=8.8 Hz), 7.27(d, 1H, J=2.2 Hz), 7.21(d, 2H, J=8.6 Hz), 6.86(dd, 1H, J$_1$=8.7 Hz, J$_2$=2.3 Hz), 6.73(d, 2H, J=8.9 Hz), 6.67(d, 2H, J=8.6 Hz), 3.94(t, 2H, J=6.1 Hz), 2.39(m, 1H), 2.10–1.97(m, 2H), 1.82–1.55(m, 8H).

Mass(ESI): 623 (M+1)

Example 10

Synthesis of 2-[4-[4-[(6-hydroxy-2-(4-hydroxyphenyl)benzo-[b]thiophen-3-yl)carbonyl]phenoxy]butyl]-6,6,7,7,7-pentafluoroheptanoic acid

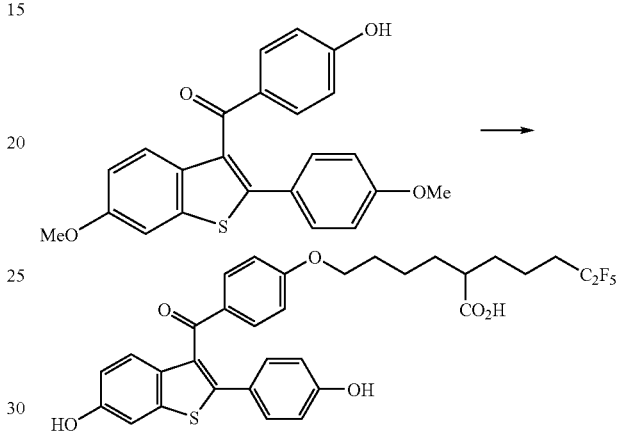

The same procedure as shown in Example 1 was repeated to give 2-[4-[4-[(6-hydroxy-2-(4-hydroxyphenyl)benzo[b]thiophen-3-yl)carbonyl]phenoxy]butyl]-6,6,7,7,7-pentafluoroheptanoic acid.

$^1$H-NMR(300 MHz, CDCl$_3$): 7.71 (d, 2H, J=8.8 Hz), 7.54(d, 1H, J=8.7 Hz), 7.26(d, 1H, J=2.3 Hz), 7.19(d, 2H, J=8.6 Hz), 6.88(dd, 1H, J$_1$=8.8 Hz, J$_2$=2.3 Hz), 6.69(d, 2H, J=8.8 Hz), 6.64(d, 2H, J=8.6), 3.93(t, 2H, J=6.1 Hz), 2.38(m, 1H), 2.15–1.47(m, 12H).

Mass(ESI): 637 (M+1).

Example 11

Synthesis of 10-[(R)-7-hydroxy-3-(4-hydroxyphenyl)-3,4-dihydro-2H-benzo[1,4]oxazine-4-yl]-2-(6,6,7,7,7-pentafluoroheptyl)decanoic acid (Step 1)

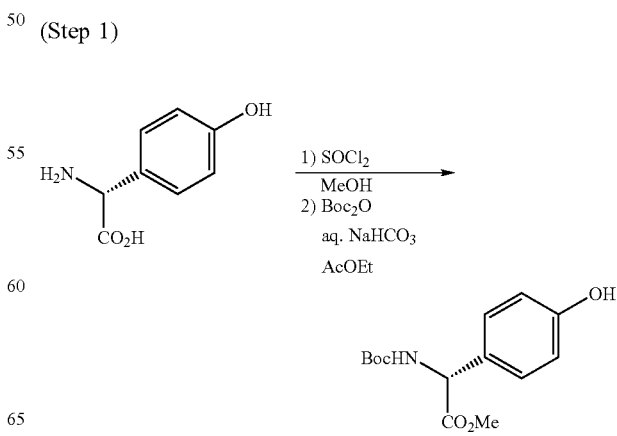

Thionyl chloride (0.65 ml) was added to (R)-4-hydroxyphenylglycine (1.00 g, 5.98 mmol) in methanol (10 ml), followed by stirring overnight at room temperature. The reaction mixture was concentrated under reduced pressure and the residue was dissolved in ethyl acetate (20 ml). Saturated aqueous sodium bicarbonate (20 ml) and di-tert-butyl-dicarbonate (1.57 g, 7.19 mmol) were added to the resulting solution followed by stirring for 4 hours at room temperature. After the reaction mixture was separated into organic and aqueous layers, the organic layer was washed sequentially with water and saturated aqueous sodium chloride, and then dried over anhydrous sodium sulfate. After the organic layer was concentrated under reduced pressure, the resulting solids were washed with ethyl acetate/hexane to give (R)-N-(tert-butoxycarbonyl)-4-hydroxyphenylglycine methyl ester (1.47 g, Yield 87%).

$^1$H-NMR (270 MHz, CDCl$_3$) δ: 7.18(2H, d, J=8.6 Hz), 6.74(2H, d, H=8.6 Hz), 5.71(1H, brs), 5.50–5.60(1H, m), 5.18–5.26(1H, m), 3.71(3H, s), 1.43(9H, s)

(Step 2)

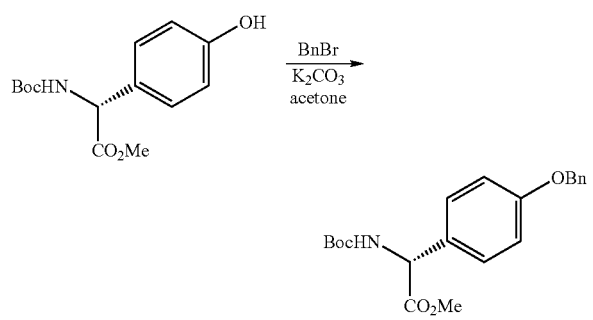

Benzyl bromide (0.66 ml, 5.55 mmol) was added to (R)-(N-tert-butoxycarbonyl)-4-hydroxyphenylglycine methyl ester (1.42 g, 5.05 mmol) and potassium carbonate (768 mg, 5.56 mmol) in acetone (5 ml). The resulting mixture was stirred overnight at room temperature and then heated under reflux for 1 hour. After cooling, the reaction mixture was concentrated under reduced pressure. Ethyl acetate was added to the resulting residue, which was then washed sequentially with water and saturated aqueous sodium chloride and dried over anhydrous sodium sulfate. After the organic layer was concentrated under reduced pressure, the resulting solids were washed with ethyl acetate/hexane to give (R)-N-(tert-butoxycarbonyl)-4-benzyloxyphenylglycine methyl ester (1.67 g, Yield 89%).

$^1$H-NMR (270 MHz, CDCl$_3$) δ: 7.30–7.45(5H, m), 7.27 (2H, d, J=8.6 Hz), 6.95(2H, d, J=8.6 Hz), 6.40–6.55(1H, m), 6.20–6.30(1H, m), 5.05(2H, s), 3.71(3H, s), 1.43(9H, s)

(Step 3)

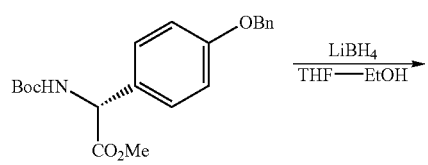

-continued

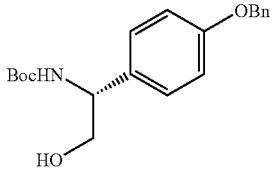

Ethanol (4 ml) was added to (R)-N-(tert-butoxy-carbonyl)-4-benzyloxyphenylglycine methyl ester (200 mg, 0.538 mmol) and lithium tetrahydroborate (23 mg, 1.06 mmol) in tetrahydrofuran (2 ml), followed by stirring overnight at room temperature. The reaction mixture was acidified (pH 4) with 10% citric acid and concentrated under reduced pressure. Ethyl acetate was added to the resulting residue, which was then washed sequentially with water and saturated aqueous sodium chloride and dried over anhydrous sodium sulfate. The organic layer was concentrated under reduced pressure to give (R)-2-(tert-butoxycarbonyl)amino-2-(4-benzyloxyphenyl)ethanol (187 mg, Yield 100%).

$^1$H-NMR (270 MHz, CDCl$_3$) δ: 7.27–7.45(5H, m), 7.21 (2H, d, J=8.6 Hz), 6.96(2H, d, J=8.6 Hz), 5.05–5.20(1H, m), 5.05(2H, s), 5.65–5.80(1H, m), 3.75–3.85(2H, m), 2.35(1H, brs), 1.43(9H, s)

(Step 4)

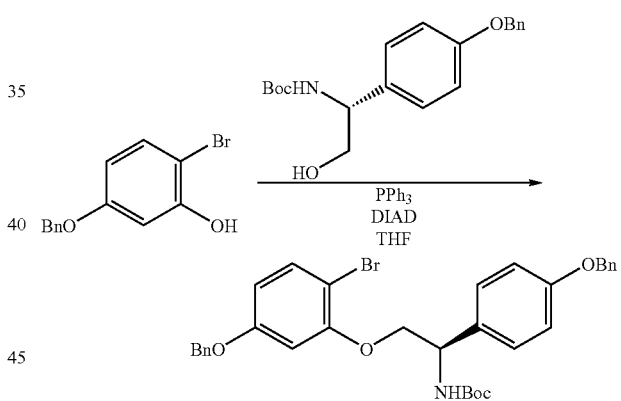

Diisopropylazodicarboxylate (0.10 ml, 0.603 mmol) was added to (R)-2-(tert-butoxycarbonyl)amino-2-(4-benzyloxyphenyl)ethanol (161 mg, 0.469 mmol), 5-benzyloxy-2-bromophenol (131 mg, 0.469 mmol) and triphenylphosphine (160 mg, 0.610 mmol) in tetrahydrofuran (3 ml) under a nitrogen stream, followed by stirring for 5 hours at room temperature. Diisopropylazodicarboxylate (0.05 ml, 0.302 mmol) was added to the reaction mixture followed by stirring for 3 hours at room temperature. Water was added to the reaction mixture, which was then extracted with ethyl acetate. The organic layer was washed sequentially with water and saturated aqueous sodium chloride, dried over anhydrous sodium sulfate, and then concentrated under reduced pressure. The resulting residue was purified by silica gel column chromatography (eluent: ethyl acetate/hexane=1/4, v/v) to give (R)-N-(tert-butoxycarbonyl)-2-(5-benzyloxy-2-bromophenoxy)-1(4-benzyloxyphenyl)ethylamine (214 mg, Yield 75%).

$^1$H-NMR (270 MHz, CDCl$_3$) δ: 7.25–7.45(13H, m), 6.95 (2H, d, J=8.6 Hz), 6.40–6.55(2H, m), 5.35–5.50(1H, m), 5.05(2H, s), 5.00(2H, s), 4.95–5.05(1H, m), 4.05–4.25(2H, m), 1.42(9H, m)

(Step 5)

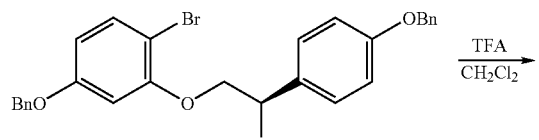

Trifluoroacetic acid (1 ml) was added to (R)-N-(tert-butoxycarbonyl)-2-(5-benzyloxy-2-bromophenoxy)-1-(4-benzyloxyphenyl)ethylamine (200 mg, 0.331 mmol) in methylene chloride (1 ml), followed by stirring for 1 hour at room temperature. The reaction mixture was concentrated under reduced pressure, made basic with saturated aqueous sodium bicarbonate, and then extracted with ethyl acetate. The organic layer was washed with saturated aqueous sodium chloride, dried over anhydrous sodium sulfate, and concentrated under reduced pressure. The resulting residue was purified by silica gel column chromatography (eluent: ethyl acetate/hexane=2/1, v/v) to give (R)-2-(5-benzyloxy-2-bromophenoxy)-1-(4-benzyloxyphenyl)ethylamine (127 mg, Yield 76%).

$^1$H-NMR (270 MHz, CDCl$_3$) δ: 7.25–7.45(13H, m), 6.97 (2H, d, J=8.6 Hz), 6.42–6.53(2H, m), 5.07(2H, s), 5.00(2H, s), 4.42(1H, dd, J=8.9, 3.6 Hz), 4.07(1H, dd, J=8.9, 3.6 Hz), 3.87(1H, dd, J=8.9, 8.9 Hz), 1.77(2H, brs)

(Step 6)

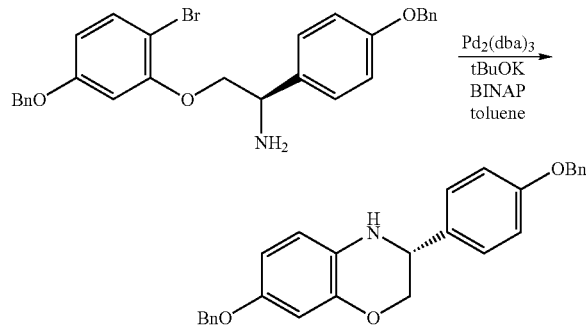

A solution of (R)-2-(5-benzyloxy-2-bromophenoxy)-1-(4-benzyloxyphenyl)ethylamine (120 mg, 0.238 mmol), tris (dibenzylideneacetone)dipalladium (11 mg, 0.012 mmol), 2,2'-bis(diphenylphosphino)-1,1'-binaphthyl (15 mg, 0.024 mmol) and potassium-t-butoxide (37 mg, 0.330 mmol) in toluene (2.5 ml) was stirred for 3 hours at 100° C. under a nitrogen stream. After cooling, water was added to the reaction mixture, which was then extracted with ethyl acetate. The organic layer was washed with saturated aqueous sodium chloride, dried over anhydrous sodium sulfate, and concentrated under reduced pressure. The resulting residue was purified by silica gel column chromatography (eluent: ethyl acetate/hexane=1/5, v/v) to give (R)-7-benzyloxy-3-(4-benzyloxy-phenyl)-3,4-dihydro-2H-benzo[1,4] oxazine (55.4 mg, Yield 55%).

$^1$H-NMR (270 MHz, CDCl$_3$) δ: 7.25–7.50(12H, m), 6.98 (2H, d, J=8.6 Hz), 6.58(1H, d, J=8.6 Hz), 6.55(1H, d, J=2.6 Hz), 6.48(1H, dd, J=8.6, 2.6 Hz), 5.07(2H, s), 4.99(2H, s), 4.39(1H, dd, J=8.9, 2.6 Hz), 4.22(1H, dd, J=10.6, 2.6 Hz), 3.96(1H, dd, 10.6, 8.9 Hz), 3.73(1H, brs)

(Step 7)

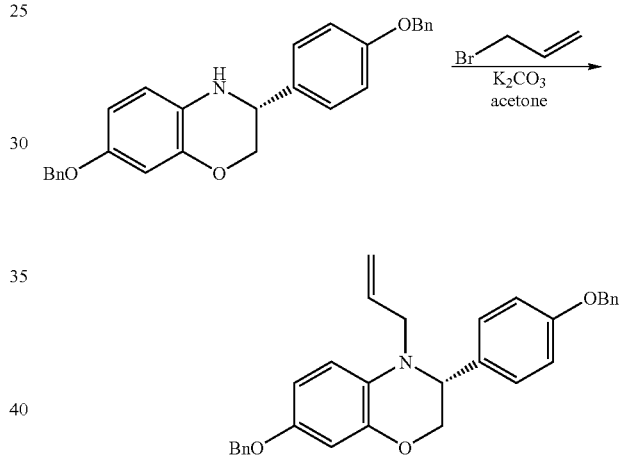

A solution of (R)-7-benzyloxy-3-(4-benzyloxyphenyl)-3,4-dihydro-2H-benzo[1,4]oxazine (47.6 mg, 0.112 mmol), sodium iodide (67 mg, 0.450 mmol), potassium carbonate (31 mg, 0.224 mmol) and allyl bromide (0.04 ml, 0.473 mmol) in acetone (1 ml) was stirred for 3 hours at 50° C. under a nitrogen stream and then heated under reflux for 7 hours. After cooling, water was added to the reaction mixture, which was then extracted with ethyl acetate. The organic layer was washed with saturated aqueous sodium chloride, dried over anhydrous sodium sulfate, and concentrated under reduced pressure. The resulting residue was purified by silica gel column chromatography (eluent: ethyl acetate/hexane=1/5, v/v) to give (R)-4-allyl-7-benzyloxy-3-(4-benzyloxyphenyl)-3,4-dihydro-2H-benzo[1,4]oxazine (44 mg, Yield 85%).

$^1$H-NMR (270 MHz, CDCl$_3$) δ: 7.25–7.45(10H, m), 7.20 (2H, d, J=8.6 Hz), 6.95(2H, d, J=8.6 Hz), 6.74(1H, d, J=9.6 Hz), 6.50–6.56(2H, m), 5.68–5.85(1H, m), 5.06–5.17(2H, m), 5.05(2H, s), 4.98(2H, s), 4.33(1H, d, J=6.9, 3.0 Hz), 4.19(1H, dd, J=10.9, 3.0 Hz), 4.11(1H, dd, J=10.9, 6.9 Hz), 4.85–4.98(1H, m), 3.47(1H, dd, J=16.8, 6.3 Hz)

(Step 8)

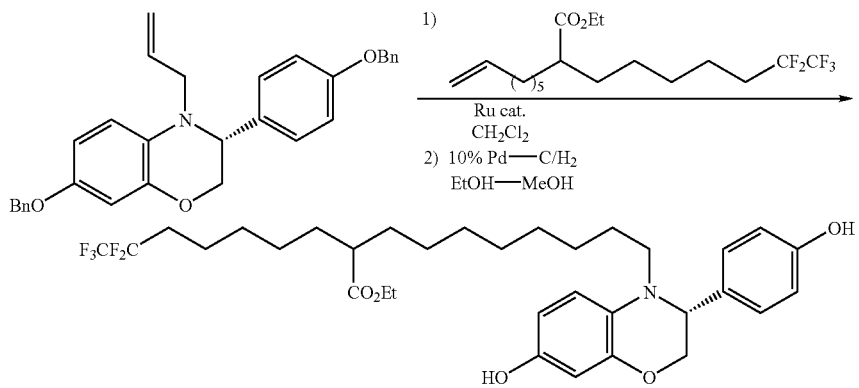

1) A solution of (R)-4-allyl-7-benzyloxy-3-(4-benzyloxyphenyl)-3,4-dihydro-2H-benzo-[1,4]oxazine (177 mg, 0.382 mmol), 2-(6,6,7,7,7-pentafluoroheptyl)-non-8-enoic acid ethyl ester (285 mg, 0.765 mmol) and benzylidene-bis(tricyclohexylphosphine)-dichlororuthenium (16 mg, 0.019 mmol) in dichloromethane(2 ml) was heated under reflux for 5 hours under a nitrogen stream. The reaction mixture was further mixed with 2-(6,6,7,7,7-pentafluoroheptyl)-non-8-enoic acid ethyl ester (71 mg, 0.190 mmol) and benzylidene-bis(tricyclohexylphosphine)-dichlororuthenium (16 mg, 0.019 mmol) and then heated under reflux for 2 hours. After cooling, the reaction mixture was concentrated under reduced pressure. The resulting residue was purified by silica gel column chromatography (eluent: chloroform/hexane=3/1, v/v) to give an oil (197 mg).

2) A mixture of the oil prepared in 1) above and 10% Pd—C (13 mg, 0.012 mmol) in ethanol/methanol (1:1, 3 ml) was stirred for 13 hours at room temperature under a hydrogen stream. After the reaction mixture was filtered through cellite, the mother liquid was concentrated under reduced pressure. The resulting residue was subjected to two additional reduction reactions as stated above. The resulting residue was further purified by silica gel column chromatography (eluent: ethyl acetate/hexane=1/2→1/1, v/v) to give ethyl 10-[(R)-7-hydroxy-3-(4-hydroxyphenyl)-3,4-dihydro-2H-benzo-[1,4]oxazine-4-yl]-2-(6,6,7,7,7-pentafluoroheptyl)decanoate (60.2 mg, Yield 26%).

$^1$H-NMR (270 MHz, CD$_3$OD) δ: 7.13(2H, d, J=8.6 Hz), 6.78(2H, d, J=8.6 Hz), 6.65(1H, d, J=8.6 Hz), 6.36(1H, dd, J=8.6, 2.6 Hz), 6.29(1H, d, J=2.6 Hz), 4.27(1H, dd, J=6.3, 3.0 Hz), 4.00–4.20(4H, m), 3.20–3.35(1H, m), 2.80–2.95 (1H, m), 2.30–2.45(1H, m), 2.00–2.23(2H, m), 1.15–1.70 (25H, m)

(Step 9)

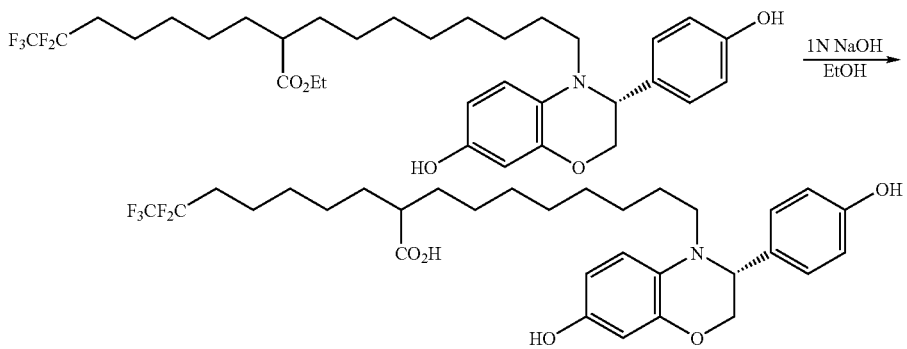

Aqueous sodium hydroxide (1N, 1 ml) was added to ethyl 10-[(R)-7-hydroxy-3-(4-hydroxyphenyl)-3,4-dihydro-2H-benzo[1,4]-oxazine-4-yl]-2-(6,6,7,7,7-pentafluoroheptyl) decanoate (56.8 mg, 0.0902 mmol) in ethanol (1 ml) under a nitrogen stream, followed by stirring for 7 hours at 50° C. After cooling, the reaction mixture was acidified with 1N aqueous hydrochloric acid and extracted with ethyl acetate. The organic layer was washed sequentially with water and saturated aqueous sodium chloride, dried over anhydrous sodium sulfate, and then concentrated under reduced pressure. The resulting residue was purified by silica gel column chromatography (eluent: ethyl acetate/hexane=1/1, v/v) to give 10-[(R)-7-hydroxy-3-(4-hydroxyphenyl)-3,4-dihydro-2H-benzo[1,4]-oxazine-4-yl]-2-(6,6,7,7,7-pentafluoroheptyl)decanoic acid (41.4 mg, Yield 76%).

$^1$H-NMR (270 MHz, CD$_3$OD) δ: 7.13(2H, d, J=8.6 Hz), 6.78(2H, d, J=8.6 Hz), 6.64(1H, d, J=8.6 Hz), 6.37(1H, dd, J=8.6, 2.6 Hz), 6.29(1H, d, J=2.6 Hz), 4.21–4.35(1H, m), 4.12(1H, dd, J=10.6, 3.0 Hz), 4.05(1H, dd, J=10.6, 6.6 Hz), 3.20–3.35(1H, m), 2.82–2.95(1H, m), 2.25–2.38(1H, m), 2.00–2.21(2H, m), 1.10–1.70(22H, m)

Example 12

Synthesis of 10-[3,17β-dihydroxyestra-1,3,5(10)-trien-11β-yl]-2-(6,6,7,7,7-pentafluoroheptyl)decanoic acid

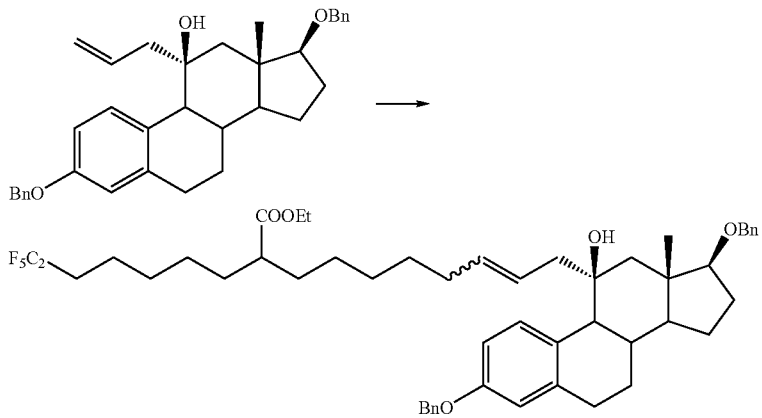

(Step 1)

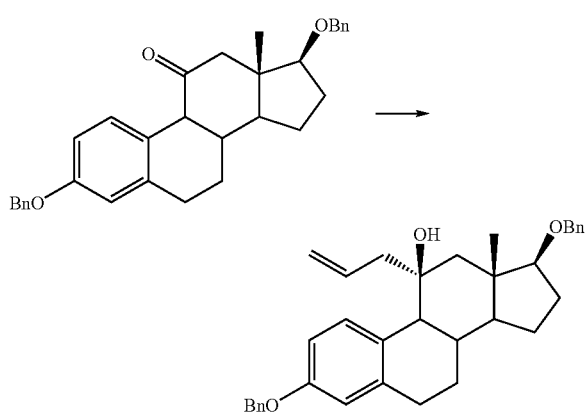

A solution of 3,17β-bis(benzyloxy)estra-1,3,5(10)-trien-11-one (148.8 mg, 0.318 mmol) in anhydrous tetrahydrofuran (2.5 ml) was cooled to −10° C. under argon atmosphere. To this solution, a 1.0 M solution of allyl magnesium bromide in anhydrous ether (1.5 ml, 1.5 mmol) was added dropwise, and the resulting mixture was stirred for 15 hours at room temperature. The reaction mixture was cooled to 0° C., followed by addition of water and saturated aqueous ammonium chloride. After the reaction mixture was extracted with ethyl acetate, the organic layer was washed with saturated aqueous sodium chloride, dried over anhydrous magnesium sulfate, and then filtered. After distilling off the solvent, the residue was purified by silica gel flash chromatography (eluent: hexane/ethyl acetate=6/1) to give 3,17β-bis(benzyloxy)-11α-(2-propenyl)estra-1,3,5(10)-trien-11β-ol (150.4 mg, Yield 93%).

$^1$H-NMR (270 MHz, CDCl$_3$): δ 7.79 (d, J=10 Hz, 1H, C1-H), 7.44–7.29 (m, 10H), 6.82–6.76 (m, 2H, C2 and C4-H), 6.00–5.85 (m, 1H, olefin-H), 5.20–5.12 (m, 2H, olefin-H), 5.04 (s, 2H, Ph—CH$_2$), 4.55 (s, 2H, Ph—CH$_2$), 3.44 (t, J=8 Hz, 1H, C17-H), 2.88 (dd, J=14, 8 Hz, 1H, allylic-CH$_2$), 2.78–2.58 (m, 2H), 2.50 (dd, J=14, 7 Hz, 1H, allylic-CH$_2$), 2.23 (d, J=11 Hz, 1H), 2.11 (d, J=14 Hz, 1H), 2.08–1.95 (m, 1H), 1.90–1.15 (m, 9H), 1.07(s, 3H, C18-H).

(Step 2)

Benzylidenebis(tricyclohexylphosphine)-dichlororuthenium (5.9 mg, 0.00717 mmol) was added to a solution of 3,17β-bis(benzyloxy)-11α-(2-propenyl)estra-1,3,5(10)-trien-11β-ol (65.5 mg, 0.129 mmol) and ethyl 2-(6,6,7,7,7-pentafluoroheptyl)-8-nonenoate (101.3 mg, 0.272 mmol) in dichloromethane (0.5 ml), followed by heating under reflux for 2.5 hours under argon atmosphere. After cooling, ethyl 2-(6,6,7,7,7-pentafluoroheptyl)-8-nonenoate (100 mg, 0.269 mmol) and benzylidenebis(tricyclohexylphosphine)-dichlororuthenium (6 mg, 0.00729 mmol) were added to the reaction mixture, which was then heated under reflux for 3 hours under argon atmosphere. After cooling, ethyl 2-(6,6,7,7,7-pentafluoroheptyl)-8-nonenoate (100 mg, 0.269 mmol) and benzylidenebis(tricyclohexylphosphine)-dichlororuthenium (6 mg, 0.00729 mmol) were further added to the reaction mixture, which was then heated under reflux for 6.5 hours under argon atmosphere and allowed to cool. Apart from this, benzylidenebis(tricyclohexylphosphine)-dichlororuthenium (6.8 mg, 0.00826 mmol) was added to a solution of 3,17β-bis(benzyloxy)-11α-(2-propenyl)estra-1,3,5(10)-trien-11β-ol (84.5 mg, 0.166 mmol) and ethyl 2-(6,6,7,7,7-pentafluoroheptyl)-8-nonenoate (124 mg, 0.333 mmol) in dichloromethane (0.5 ml), followed by heating under reflux for 2.5 hours under argon atmosphere. After cooling, ethyl 2-(6,6,7,7,7-pentafluoroheptyl)-8-nonenoate (124 mg, 0.333 mmol) and benzylidenebis(tricyclohexylphosphine)-dichlororuthenium (6.8 mg, 0.00826 mmol) were added to the reaction mixture, which was then heated under reflux for 3 hours under argon atmosphere. After cooling, ethyl 2-(6,6,7,7,7-pentafluoroheptyl)-8-nonenoate (124 mg, 0.333 mmol) and benzylidenebis(tricyclohexylphosphine)-dichlororuthenium (6.8 mg, 0.00826 mmol) were further added to the reaction mixture, which was then heated under reflux for 6.5 hours under argon atmosphere and allowed to cool. The thus prepared two reaction mixtures were combined and concentrated under reduced pressure. The residue was purified by silica gel flash chromatography (eluent: hexane/ethyl acetate=5/1) to give ethyl 10-[3,17β-bis(benzyloxy)-11β-hydroxyestra-1,3,5(10)-trien-11α-yl]-2-(6,6,7,7,7-pentafluoroheptyl)-8-decenoate (186.4 mg, Yield 74%).

¹H-NMR(270 MHz, CDCl₃): δ 7.79(d, J=100 Hz, 1H), 7.45–7.25(m, 10H), 6.82–6.72(m, 2H), 5.62–5.40(m, 2H, olefin-H), 5.04(s, 2H, Ph—CH₂), 4.55(s, 2H, Ph—CH₂), 4.13(q, J=7 Hz, 2H, COO—CH₂), 3.42(t, J=8 Hz, 1H), 2.95–1.14(m, 40H), 1.07(s, 3H).

(Step 3)

hours at room temperature under hydrogen atmosphere. After purging with nitrogen, 10% palladium carbon (74.0 mg) was added to the reaction mixture, followed by stirring for 15 hours at room temperature under hydrogen atmosphere. The reaction mixture was filtered and concentrated, the residue was dissolved in methanol (10 ml). 10% Palladium carbon (80 mg) was added again to the reaction mixture, followed by stirring for 2 days at room temperature under hydrogen atmosphere. After the reaction mixture was

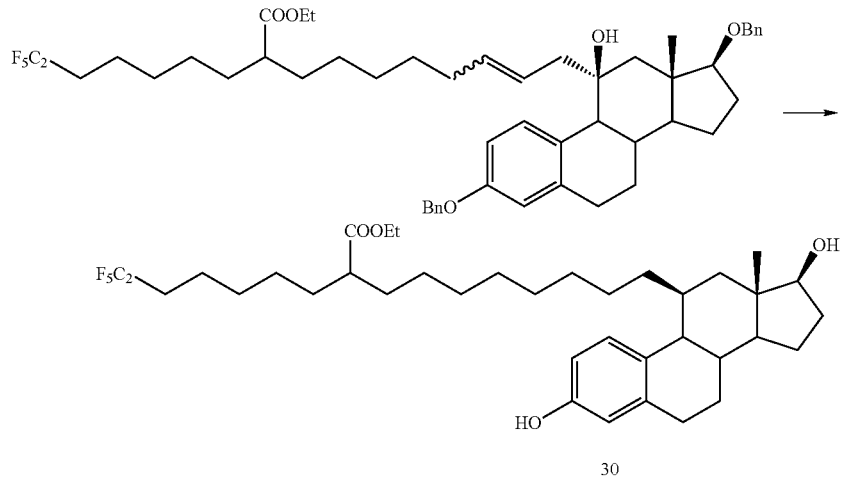

A 30% solution of HBr in acetic acid (2 ml) was added to a solution of ethyl 10-[3,17β-bis(benzyloxy)-11β-hydroxyestra-1,3,5(10)-trien-11α-yl]-2-(6,6,7,7,7-pentafluoroheptyl)-8-decenoate (155.4 mg, 0.182 mmol) in ethanol (8 mL), followed by stirring for 24 hours at 50° C. After cooling, the reaction mixture was poured into saturated aqueous sodium bicarbonate and extracted with ethyl acetate. The organic layer was washed with saturated aqueous sodium chloride, dried over anhydrous magnesium sulfate, and then filtered. After concentration under reduced pressure, the resulting residue was purified by silica gel flash chromatography (eluent: hexane/ethyl acetate=20/1) to give an oil. This oil was dissolved in a mixed solvent of ethanol (5 ml) and methanol (5 ml). 10% palladium carbon (78.8 mg) was added to the resulting solution followed by stirring for 14 filtered and concentrated, the residue was purified by silica gel flash chromatography (eluent: hexane/ethyl acetate=10/1) to give an oil. This oil was further purified using a silica gel plate (developing solvent: hexane/ethyl acetate=2/1) to give ethyl 10-[3,17β-dihydroxyestra-1,3,5(10)-trien-11β-yl]-2-(6,6,7,7,7-pentafluoroheptyl)decanoate (14.6 mg, Yield 12%).

¹H-NMR (270 MHz, CDCl₃): δ 7.00(d, J=8.6 Hz, 1H), 6.62(dd, J=8.6, 2.6 Hz, 1H), 6.55(d, J=2.6 Hz, 1H), 5.28(bs, 1H, Ar—OH), 4.15(q, J=7.3 Hz, 2H, COO—CH₂), 3.70(t, J=8.6 Hz, 1H), 2.90–1.10(m, 45H), 0.91(s, 3H).

Rf value: 0.45 (silica gel plate, developing solvent: hexane/ethyl acetate=2/1).

(Step 4)

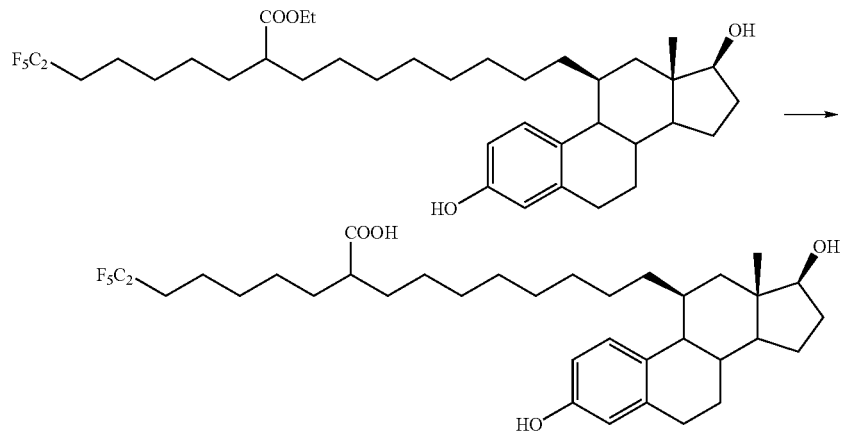

Ethyl 10-[3,17β-dihydroxyestra-1,3,5(10)-trien-11β-yl]-2-(6,6,7,7,7-pentafluoroheptyl)decanoate (11.1 mg, 0.0168 mmol) was dissolved in a mixed solvent of ethanol (0.5 ml) and tetrahydrofuran (0.5 ml). To this solution, 1N aqueous NaOH (0.5 ml) was added and the resulting mixture was heated under reflux for 5 hours. After cooling, saturated aqueous ammonium chloride was added to the reaction mixture, which was then extracted with ethyl acetate. The organic layer was washed with saturated aqueous sodium chloride, dried over anhydrous magnesium sulfate, and then filtered. After concentration under reduced pressure, the resulting residue was purified using a silica gel plate (developing solvent: hexane/ethyl acetate=1/1) to give 10-[3,17β-dihydroxyestra-1,3,5(10)-trien-11β-yl]-2-(6,6,7,7,7-pentafluoroheptyl)decanoic acid (5.3 mg, Yield 50%).

$^1$H-NMR(270 MHz, CDCl$_3$): δ 7.00(d, J=8.3 Hz, 1H), 6.62(d, J=8.3 Hz, 1H), 6.54(s, 1H), 3.73(t, J=8.1 Hz, 1H), 2.90–1.07(m, 42H), 0.92(s, 3H).

Mass (ESI): 653(M+Na).

Rf value: 0.22 (silica gel plate, developing solvent: hexane/ethyl acetate=1/1).

Example 13

Synthesis of 11-(3,17β-dihydroxyestra-1,3,5(10)-trien-7α-yl)-2-(4,4,5,5,5-penta-fluoropentyl)undecanoic acid (Step 1)

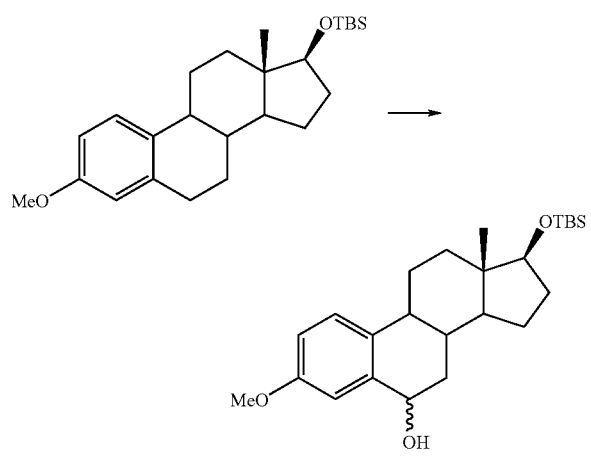

n-Butyllithium (2.5 M in hexane, 40 ml, 100 mmol) was added to potassium tert-butoxide (1M in tetrahydrofuran, 100 ml, 100 mmol) at −70° C. under nitrogen atmosphere, followed by addition of diisopropylamine (19.1 g, 100 mmol) at the same temperature. After the mixture was stirred for 10 minutes, 17β-(t-butyldimethylsiloxy)-3-methoxyestra-1,3,5(10)-triene (10 g, 25 mmol) synthesized by the method described in Tetrahedron Lett., 3223 (1988) and dissolved in tetrahydrofuran (40 ml) was added dropwise at −70° C. over 10 to 15 minutes, and the resulting mixture was stirred for 4 hours. Trimethyl borate (15.6 g, 150 mmol) was added to the reaction mixture, which was then warmed to ice cold temperature and stirred for 1 hour and further stirred with 30% hydrogen peroxide (35 ml) for 1 hour at room temperature. The reaction mixture was cooled again on ice and 10% aqueous sodium thiosulfate (150 ml) was added to stop the reaction. After the reaction mixture was extracted with ether, the organic layer was washed with water and saturated aqueous sodium chloride, dried over anhydrous magnesium sulfate, and then filtered. After distilling off the solvent, the residue was purified by silica gel flash chromatography (eluent: hexane/ethyl acetate=5/1→3/1) to give 17β-(t-butyl-dimethylsiloxy)-3-methoxyestra-1,3,5(10)-trien-6-ol (8.38 g, Yield 82%).

$^1$H-NMR(300 MHz, CDCl$_3$) δ 7.18 (d, J=8.5 Hz, 1H, C1-CH), 7.11 (d, J=2.7 Hz, 1H, C4-CH), 6.77 (dd, J=8.5, 2.7 Hz, 1H, C2-CH), 4.8 (m, 1H), 3.78 (s, 3H, C3-OCH3), 3.62 (m, 1H), 2.3–2.2 (m, 3H), 2.0–1.8 (m, 2H), 1.7–1.1 (m, 8H), 0.87 (s, 9H), 0.71 (s, 3H, C18-CH$_3$), 0.04 (s, 3H), 0.03 (s, 3H).

(Step 2)

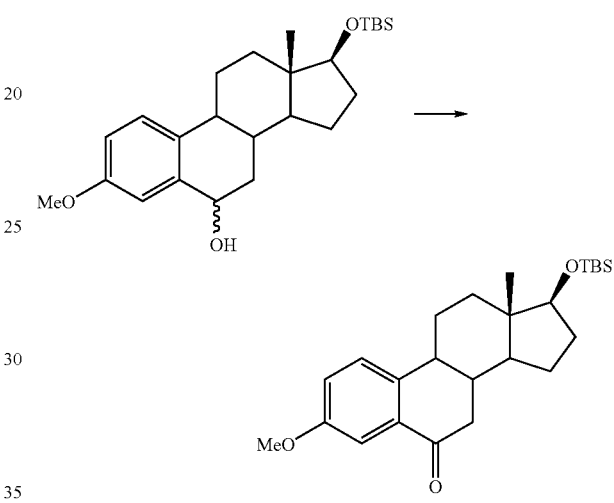

17β-(t-Butyldimethylsiloxy)-3-methoxyestra-1,3,5(10)-trien-6-ol (14.4 g, 34.5 mmol) was dissolved in dichloromethane (250 ml). Manganese dioxide (29 g) and molecular sieves 4A powder (7.2 g) were added to the resulting solution followed by stirring for 1 hour at room temperature. The reaction mixture was filtered through cellite and the filtrate was concentrated under reduced pressure. The residue was recrystallized from hexane to give 17β-(t-butyldimethylsiloxy)-3-methoxyestra-1,3,5(10)-trien-6-one (11.36 g, Yield 79%).

$^1$H-NMR(300 MHz, CDCl$_3$): δ 7.55 (d, J=3.0 Hz, 1H, C4-CH), 7.34 (d, J=8.5 Hz, 1H, C1-CH), 7.10 (dd, J=8.5, 3.0 Hz, 1H, C2-CH), 3.84 (s, 3H, C3-OCH$_3$), 3.66 (m, 1H), 2.74 (dd, J=16.8, 3.3 Hz, 1H), 2.5–2.3 (m, 2H), 2.19 (dd, J=16.8, 13.2 Hz, 1H), 2.0–1.8 (m, 3H), 1.7–1.2 (m, 5H), 0.89 (s, 9H), 0.75 (s, 3H, C18-CH$_3$), 0.04 (s, 3H), 0.03 (s, 3H).

mp. 159–160° C.

(Step 3)

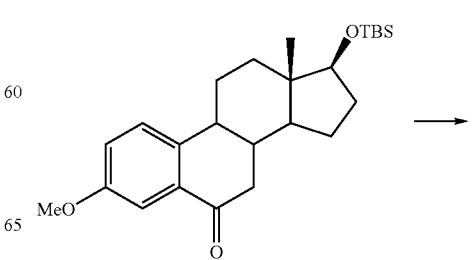

-continued

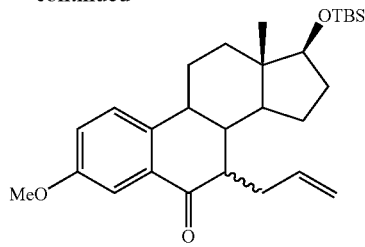

A solution of 17β-(t-butyldimethylsiloxy)-3-methoxyestra-1,3,5(10)-trien-6-one (2.12 g, 5 mmol) in anhydrous 1,2-dimethoxyethane (30 ml) was cooled to −70° C. under nitrogen atmosphere, and potassium hexamethyl-disilazide in solid form (1.1 g, 5.5 mmol) was added to the resulting solution followed by stirring for 1 hour while keeping the temperature at −70° C. Distilled allyl iodide (1.68 g, 10 mmol) was then added at −70° C. using a syringe and the reaction mixture was warmed to 0° C. over 1 hour. An hour later, water was added at 0° C. to the reaction mixture, which was then extracted with ether. The organic layer was washed with water and saturated aqueous sodium chloride, dried over anhydrous magnesium sulfate, and then filtered. After distilling off the solvent, the residue was purified by silica gel flash chromatography (eluent: hexane/ethyl acetate=20/1→15/1) to give 17β-(t-butyldimethylsiloxy)-3-methoxy-7αβ-(2-propenyl)estra-1,3,5(10)-trien-6-one (2.0 g, Yield 88%). (7α/7β ratio: about 1/6)

The above mixture was dissolved in sodium methoxide solution (0.1 M) and heated under reflux for 2 hours to give a mixture having a 7α/7β ratio of about 7/1.

$^1$H-NMR(300 MHz, CDCl$_3$, spectrum of 7α-substituted compound): δ 7.53 (d, 1H, J=2.8 Hz, C4-CH), 7.32 (d, 1H, J=8.5 Hz, C1-CH), 7.09 (dd, J=8.5, 2.8 Hz, 1H, C2-CH), 5.87–5.72 (m, 1H), 5.02–4.9 (m, 2H), 3.84 (s, 3H, C3-OCH$_3$), 3.68 (m, 1H), 2.77–2.64 (m, 1H), 2.6–2.54 (m, 1H), 2.4–2.3 (m, 2H), 2.22–2.06 (m, 2H), 2.0–1.85 (m, 2H), 1.65–1.2 (m, 6H), 0.9 (s, 9H), 0.75 (s, 3H, C18-CH$_3$), 0.05 (s, 3H), 0.03 (s, 3H).

(Step 4)

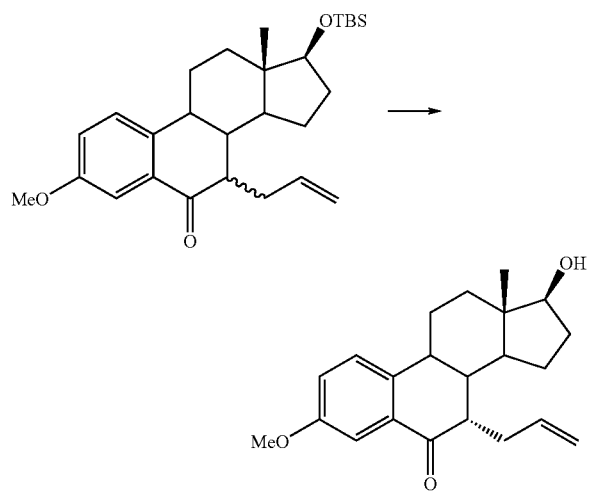

17β-(t-Butyldimethylsiloxy)-3-methoxy-7αβ-(2-propenyl)estra-1,3,5(10)-trien-6-one (5.78 g, 12.7 mmol) was dissolved in tetrahydrofuran (30 ml). To this solution, tetra-n-butylammonium fluoride (1M in tetrahydrofuran, 60 ml) was added, and the resulting mixture was heated under reflux for 4 hours under nitrogen atmosphere. After cooling, water was added to the reaction mixture, which was then extracted with ether. The organic layer was washed with saturated aqueous sodium chloride, dried over anhydrous sodium sulfate, and then filtered. The filtrate was concentrated under reduced pressure to give 17β-hydroxy-3-methoxy-7αβ-(2-propenyl)estra-1,3,5(10)-trien-6-one as a diastereomer mixture, which was then recrystallized from diisopropyl ether (70 ml) to give 17β-hydroxy-3-methoxy-7α-(2-propenyl)estra-1,3,5(10)-trien-6-one (2.61 g, Yield 60%) as a single isomer.

$^1$H-NMR(270 MHz, CDCl$_3$): δ 7.53(d, J=3.0 Hz, 1H, C4-CH), 7.32(d, J=8.5 Hz, 1H, C1-CH), 7.09(dd, J=8.5, 3.0 Hz, 1H, C2-CH), 5.84–5.74(m, 1H), 5.01–4.92(m, 2H, olefin-H), 3.84(s, 3H, C3-OCH$_3$), 3.84–3.75(m, 1H, C17-CH), 2.80–2.68(m, 1H, C9-CH), 2.63–2.52(m, 1H, C7-CH), 2.51–2.38(m, 2H, allyl-CH$_2$ and C11-CH$_2$), 2.24–2.05(m, 3H, allyl-CH$_2$ and C8-CH and C16-CH$_2$), 2.02–1.91(m, 1H, C11-CH$_2$), 1.71–1.33(m, 7H), 0.79(s, 3H, C18-CH$_3$).

mp 122–123° C.

(Step 5)

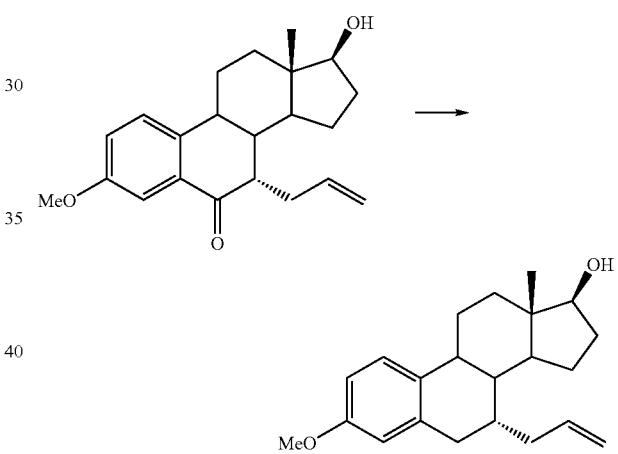

Triethylsilane (5 ml) and boron trifluoride diethyl etherate (5 ml) were added to a solution of 17β-hydroxy-3-methoxy-7α-(2-propenyl)estra-1,3,5(10)-trien-6-one (1.0 g, 2.9 mmol) in dichloromethane (20 mL) at 0° C. The resulting mixture was warmed to room temperature and stirred for 18 hours. After the reaction was completed, 10% aqueous potassium carbonate was added to the reaction mixture, which was then extracted with ethyl acetate. The organic layer was washed with saturated aqueous sodium chloride, dried over anhydrous sodium sulfate, and then filtered. After concentration under reduced pressure, the resulting residue was purified by silica gel column chromatography (eluent: hexane/ethyl acetate=2/1) to give 3-methoxy-7α-(2-propenyl)estra-1,3,5(10)-trien-17β-ol (935 mg, Yield 98%).

$^1$H-NMR(270 MHz, CDCl$_3$): δ 7.20(d, J=8.6 Hz, C1-1H), 6.71(dd, J=8.6, 2.4 Hz, C2-1H), 6.60(d, J=2.4 Hz, C4-1H), 5.86–5.72(m, 1H), 5.00–4.90(m, 2H, olefin-H), 3.77(s, 3H, C3-OCH$_3$), 3.77–3.71(m, 1H, C17-CH), 2.80–2.68(m, 1H, C9-CH), 2.63–2.52(m, 1H, C7-CH), 2.51–2.38(m, 2H, allyl-CH$_2$ and C11-CH$_2$), 2.24–2.05(m, 3H, allyl-CH$_2$ and C8-CH and C16-CH$_2$), 2.02–1.91(m, 1H, C11-CH$_2$), 1.71–1.33(m, 7H), 0.79(s, 3H, C18-CH$_3$).

(Step 6)

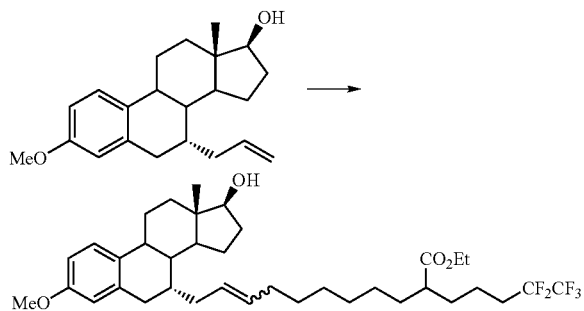

Benzylidenebis(tricyclohexyl-phosphine)-dichlororuthenium (98 mg, 0.11 mmol) was added to a solution of 3-methoxy-7α-(2-propenyl)estra-1,3,5(10)-trien-17β-ol (723 mg, 2.21 mmol) and ethyl 2-(4,4,5,5,5-pentafluoropentyl)-9-decenoate (1.59 g, 4.43 mmol) in dichloromethane (20 ml), followed by heating under reflux for 20 hours under argon atmosphere. After cooling, the reaction mixture was concentrated under reduced pressure and the resulting residue was purified by silica gel flash chromatography (eluent: hexane/ethyl acetate=4/1) to give ethyl 11-[17β-hydroxy-3-methoxyestra-1,3,5(10)-trien-7α-yl]-2-(4,4,5,5,5-pentafluoropentyl)-9-undecenoate (973 mg, Yield 67%).

$^1$H-NMR(270 MHz, CDCl$_3$): δ 7.20(d, J=8.6 Hz, 1H, C1-CH), 6.76–6.69(m, 1H, C2-CH), 6.63–6.58(m, 1H, C4-CH), 5.42–5.27(m, 2H, olefin-H), 4.15(q, J=7.1 Hz, 2H, COO—CH$_2$), 3.78–3.70(m, 4H, C17-CH and C3-OCH$_3$), 2.90–2.63(m, 2H), 2.41–2.22(m, 3H), 2.20–1.16(m, 34H), 0.78(s, 3H, C18-CH$_3$).

(Step 7)

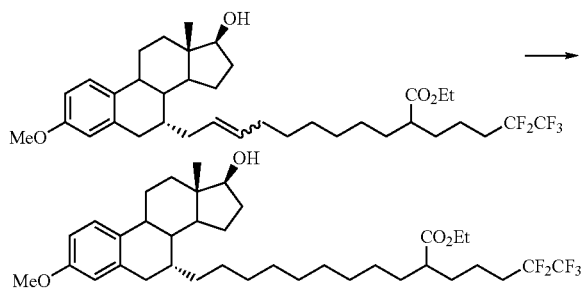

Ethyl 11-[17β-hydroxy-3-methoxyestra-1,3,5(10)-trien-7α-yl]-2-(4,4,5,5,5-pentafluoropentyl)-9-undecenoate (970 mg, 1.48 mmol) was dissolved in ethyl acetate (30 ml), and 10% palladium carbon (300 mg) was added to the resulting solution followed by stirring for 4 hours at room temperature under hydrogen atmosphere. The reaction mixture was filtered and concentrated to give ethyl 11-[17β-hydroxy-3-methoxyestra-1,3,5(10)-trien-7α-yl]-2-(4,4,5,5,5-pentafluoropentyl)undecanoate (946 mg, Yield 97%) as an oil.

$^1$H-NMR(270 MHz, CDCl$_3$): δ 7.20(d, J=8.6 Hz, 1H, C1-CH), 6.76–6.69(m, 1H, C2-CH), 6.63–6.58(m, 1H, C4-CH), 4.14(q, J=7.1 Hz, 2H, COO—CH$_2$), 3.77(s, 3H, C3-OCH$_3$), 3.74(t, J=8.4 Hz, 1H, C17-CH), 2.94–2.70(m, 2H), 2.40–2.24(m, 3H), 2.20–1.84(m, 4H), 1.80–0.96(m, 34H), 0.78(s, 3H, C18-CH$_3$).

(Step 8)

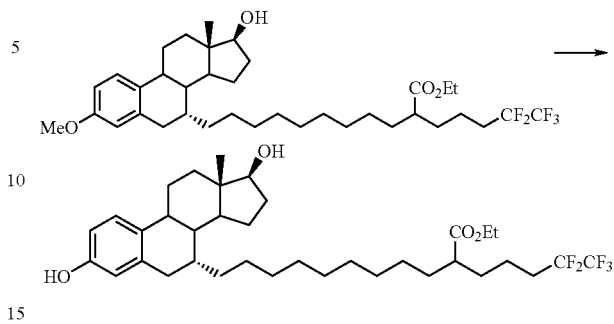

Ethyl 11-[17β-hydroxy-3-methoxyestra-1,3,5(10)-trien-7α-yl]-2-(4,4,5,5,5-pentafluoropentyl)undecanoate (946 mg, 1.43 mmol) was dissolved in dichloromethane (18 ml). To this solution, a 1M solution of borane tribromide in dichloromethane (4.3 ml, 4.3 mmol) was added dropwise at −78° C. The reaction mixture was warmed slowly and stirred for 3 hours at 0° C. Water was added to stop the reaction and the reaction mixture was extracted with ethyl acetate. The organic layer was washed with saturated aqueous sodium chloride, dried over anhydrous sodium sulfate, and then filtered. After concentration under reduced pressure, the resulting residue was purified by silica gel column chromatography (eluent: hexane/ethyl acetate=2/1) to give ethyl 11-[3,17β-dihydroxyestra-1,3,5(10)-trien-7α-yl]-2-(4,4,5,5,5-pentafluoro-pentyl)undecanoate (663 mg, Yield 72%).

$^1$H-NMR(270 MHz, CDCl$_3$): δ 7.14(d, J=8.4 Hz, 1H, C1-CH), 6.66–6.59 (m, 1H, C2-CH), 6.57–6.53(m, 1H, C4-CH), 5.10(brs, 1H, C3-OH), 4.15(q, J=7.1 Hz, 2H, COO—CH$_2$), 3.75(t, J=8.4 Hz, 1H, C17-CH), 2.94–2.68(m, 2H), 2.40–2.22(m, 3H), 2.20–1.84(m, 4H), 1.80–0.96(m, 34H), 0.78(s, 3H, C18-CH$_3$).

(Step 9)

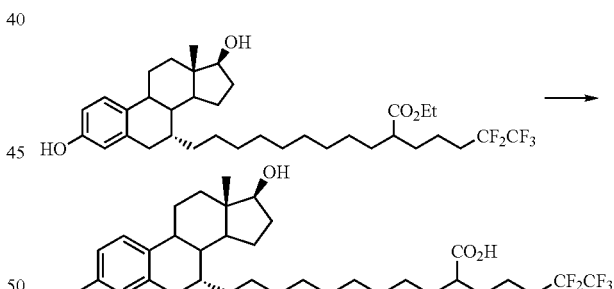

Ethyl 11-[3,17β-dihydroxyestra-1,3,5(10)-trien-7α-yl]-2-(4,4,5,5,5-pentafluoropentyl)undecanoate (660 mg, 1.03 mmol) was dissolved in a mixed solvent of ethanol (10 ml) and water (2.0 ml). To this solution, NaOH (820 mg, 20.5 mmol) was added, and the resulting mixture was heated for 4 hours at 60° C. After cooling, 2N aqueous hydrochloric acid was added to the reaction mixture, which was then extracted with ethyl acetate. The organic layer was washed with saturated aqueous sodium chloride, dried over anhydrous sodium sulfate, and then filtered. After concentration under reduced pressure, the resulting residue was purified by silica gel column chromatography (eluent: hexane/ethyl acetate=1/1) to give 11-[3,17β-dihydroxyestra-1,3,5(10)-trien-7α-yl]-2-(4,4,5,5,5-pentafluoropentyl)undecanoic acid (613 mg, Yield 97%).

¹H-NMR(270 MHz, CD₃OD): δ 7.07(d, J=8.4 Hz, 1H, C1-CH), 6.54 (dd, J=8.4, 2.3 Hz, 1H, C2-CH), 6.45(d, J=2.3 Hz, 1H, C4-CH), 3.67(t, J=8.3 Hz, 1H, C17-CH), 2.85–2.62 (m, 2H), 2.39–1.84(m, 7H), 1.80–0.96(m, 33H), 0.78(s, 3H, C18-CH₃).

Example 14

Synthesis of 10-[3,17β-dihydroxyestra-1,3,5(10)-trien-7α-yl]-2-(4,4,5,5,5-pentafluoropentyl)decanoic acid

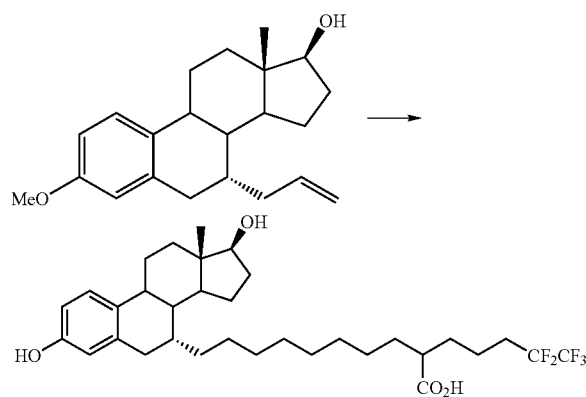

Starting with the 3-methoxy-7α-(2-propenyl)estra-1,3,5(10)-trien-17β-ol prepared in Example 13 and ethyl 2-(4,4,5,5,5-pentafluoropentyl)-8-nonenoate prepared separately, the same procedure as shown in Example 13 was repeated to give 10-[3,17β-dihydroxyestra-1,3,5(10)-trien-7α-yl]-2-(4,4,5,5,5-pentafluoropentyl)decanoic acid.

¹H-NMR(300 MHz, CDCl₃): (7.16(d, J=8.4 Hz, 1H, C1-CH), 6.63(dd, J=8.4 Hz, J=2.7 Hz, 1H, C2-CH), 6.55(s, 1H, C4-CH), 3.75(t, J=8.5 Hz, 1H, C17-CH), 3.60–3.35(brs, 1H, C3-OH), 2.82–2.73(m, 2H), 2.45–2.23(m, 4H), 2.20–0.96(m, 31H), 0.78(s, 3H, C18-CH₃).

Example 15

Synthesis of 10-[3,17β-dihydroxyestra-1,3,5(10)-trien-7α-yl]-2-(4,4,5,5,6,6,7,7,7-nonafluoroheptyl)decanoic acid

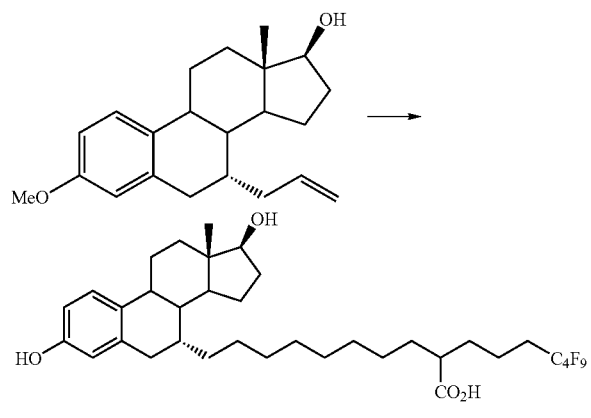

Starting with the 3-methoxy-7α-(2-propenyl)estra-1,3,5(10)-trien-17β-ol prepared in Example 13 and ethyl 2-(4,4,5,5,6,6,7,7,7-nonafluoroheptyl)-8-nonenoate prepared separately, the same procedure as shown in Example 13 was repeated to give 10-[3,17β-dihydroxyestra-1,3,5(10)-trien-7α-yl]-2-(4,4,5,5,6,6,7,7,7-nonafluoroheptyl)decanoic acid.

¹H-NMR (300 MHz; CDCl₃): (7.12(d, J=8.4 Hz, 1H), 6.68(dd, J=8.5, 2.4 Hz, 1H), 6.53(d, J=2.6 Hz, 1H), 3.68(t, J=8.5 Hz, 1H), 2.95–2.60(m, 2H), 2.47–2.19(m, 4H), 2.18–1.03(m, 31H), 0.69(s, 3H).

Example 16

Synthesis of 10-[3,17β-dihydroxyestra-1,3,5(10)-trien-7α-yl]-2-(3,3,4,4,5,5,6,6,6-nonafluorohexyl)decanoic acid

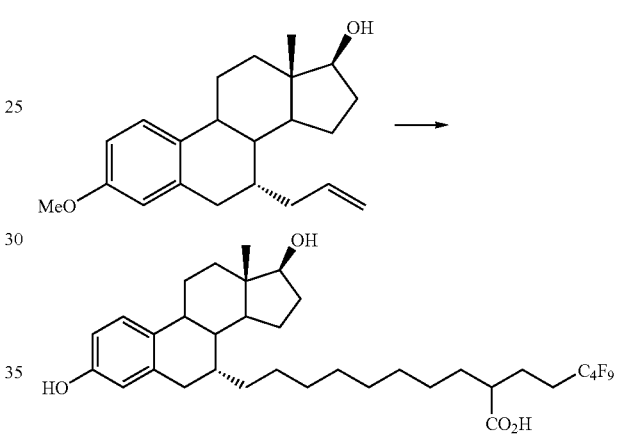

Starting with the 3-methoxy-7α-(2-propenyl)estra-1,3,5(10)-trien-17β-ol prepared in Example 13 and ethyl 2-(3,3,4,4,5,5,6,6,6-nonafluorohexyl)-8-nonenoate prepared separately, the same procedure as shown in Example 13 was repeated to give 10-[3,17β-dihydroxyestra-1,3,5(10)-trien-7α-yl]-2-(3,3,4,4,5,5,6,6,6-nonafluorohexyl)decanoic acid.

¹H-NMR (300 MHz; CDCl₃): (7.14(d, J=8.5 Hz, 1H), 6.62(dd, J=8.2, 2.1 Hz, 1H), 6.54(d, J=2.6 Hz, 1H), 3.77(t, J=8.1 Hz, 1H), 2.84–2.56(m, 2H), 2.44(m, 1H), 2.31(m, 2H), 2.18–1.02(m, 30H), 0.74(s, 3H).

Example 17

Synthesis of 10-[3,17β-dihydroxyestra-1,3,5(10)-trien-7α-yl]-2-(6,6,7,7,7-pentafluoroheptyl)decanoic acid

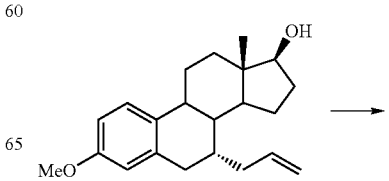

-continued

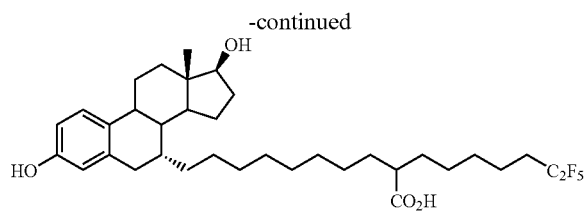

Starting with the 3-methoxy-7α-(2-propenyl)estra-1,3,5(10)-trien-17β-ol prepared in Example 13 and ethyl 2-(6,6,7,7,7-pentafluoroheptyl)-8-nonenoate prepared separately, the same procedure as shown in Example 13 was repeated to give 10-[3,17β-dihydroxyestra-1,3,5(10)-trien-7α-yl]-2-(6,6,7,7,7-pentafluoroheptyl)decanoic acid.

$^1$H-NMR (300 MHz; CDCl$_3$): (7.05(d, J=8.4 Hz, 1H), 6.65(dd, J=8.6, 2.6 Hz, 1H), 6.52(d, J=2.5 Hz, 1H), 3.75(t, J=8.4 Hz, 1H), 2.92–2.62(m, 2H), 2.33–2.12(m, 4H), 2.09–1.03(m, 35H), 0.75(s, 3H).

Example 18

Synthesis of 11-[3,17β-dihydroxyestra-1,3,5(10)-trien-7α-yl]-2-(4,4,5,5,6,6,7,7,7-nonafluoroheptyl)undecanoic acid

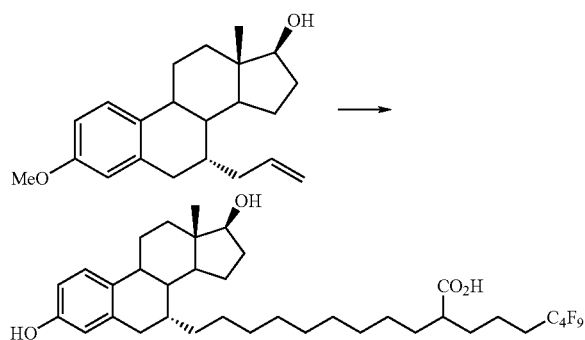

Starting with the 3-methoxy-7α-(2-propenyl)estra-1,3,5(10)-trien-17β-ol prepared in Example 13 and ethyl 2-(4,4,5,5,6,6,7,7,7-nonafluoroheptyl)-9-decenoate prepared separately, the same procedure as shown in Example 13 was repeated to give 11-[3,17β-dihydroxyestra-1,3,5(10)-trien-7α-yl]-2-(4,4,5,5,6,6,7,7,7-nonafluoroheptyl)undecanoic acid.

$^1$H-NMR(270 MHz, CDCl$_3$) δ 7.13(d, J=8.4 Hz, 1H, C1-CH), 6.62 (dd, J=8.4, 2.3 Hz, 1H, C2-CH), 6.53(d, J=2.3 Hz, 1H, C4-CH), 3.75(t, J=8.1 and 8.4 Hz, 1H, C17-CH), 2.85 (dd, J-4.8 and 16.7 Hz, 1H), 2.70(m, 1H), 2.39–1.88(m, 7H), 1.80–0.96(m, 33H), 0.78(s, 3H, C18-CH$_3$)

Example 19

Synthesis of 11-[3,17β-dihydroxyestra-1,3,5(10)-trien-7α-yl]-2-(3,3,4,4,5,5,6,6,6-nonafluorohexyl)undecanoic acid

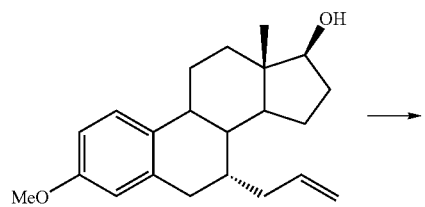

Starting with the 3-methoxy-7α-(2-propenyl)estra-1,3,5(10)-trien-17β-ol prepared in Example 13 and ethyl 2-(3,3,4,4,5,5,6,6,6-nonafluorohexyl)-9-decenoate prepared separately, the same procedure as shown in Example 13 was repeated to give 11-[3,17β-dihydroxyestra-1,3,5(10)-trien-7α-yl]-2-(3,3,4,4,5,5,6,6,6-nonafluorohexyl)undecanoic acid.

$^1$H-NMR(270 MHz, CD$_3$OD): δ 7.07(d, J=8.4 Hz, 1H, C1-CH), 6.53 (dd, J8.4, 2.2 Hz, 1H, C2-CH), 6.45(d, J=2.2 Hz, 1H, C4-CH), 3.67(t, J=8.1 Hz, 1H, C17-CH), 2.87–2.62 (m, 2H), 2.43–0.95(m, 35H), 0.78(s, 3H, C18-CH$_3$).

Example 20

Synthesis of 11-(3,17β-dihydroxyestra-1,3,5(10)-trien-11β-yl)-2-(3,3,4,4,5,5,6,6,6-nonafluorohexyl)undecanoic acid (Step 1)

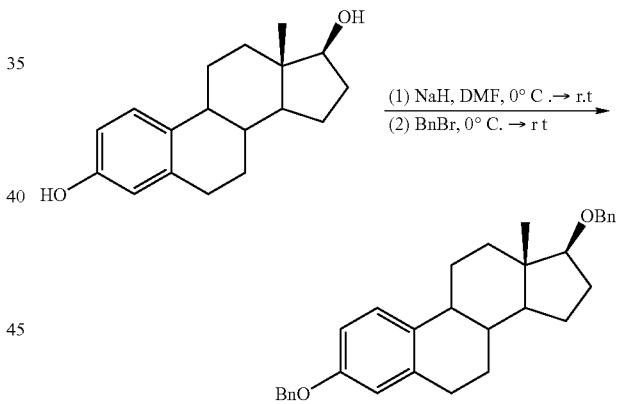

Dimethylformamide (11 ml) was added to β-estradiol (1.08 g, 4.0 mmol) under nitrogen atmosphere, followed by cooling on ice. Sodium hydride (480 mg of 60% suspension) was added to the reaction mixture followed by stirring for 10 minutes on ice and then stirred for 1 hour at room temperature. After cooling again on ice, Benzyl bromide (2.05 g, 12 mmol) was added to the reaction mixture followed by stirring for 10 minutes on ice and then stirred for 20 hours at room temperature. The reaction mixture was quenched with ice-cold water and extracted with ethyl acetate. The organic layer was washed with water and saturated aqueous sodium chloride, dried over anhydrous magnesium sulfate, and then filtered. The filtrate was concentrated under reduced pressure using an evaporator and the resulting residue was triturated with methanol to precipitate solids. The solids were collected by filtration and vacuum dried to give 3,17β-bis(benzyloxy)estra-1,3,5(10)-triene (1.72 g, Yield 95%).

¹H-NMR(300 MHz, CDCl₃): δ 7.45–7.20(m, 11H), 6.79 (dd, J=9.0 and 3.0 Hz, 1H, C3-CH), 6.72(d, J=2.7 Hz, 1H, C4-CH), 5.04(s, 2H), 4.56(s, 2H), 3.51(t, J=8.1, 1H), 2.88–2.83(m, 2H), 2.36–1.15(m, 13H), 0.88(s, 3H, C18-CH₃).

(Step 2)

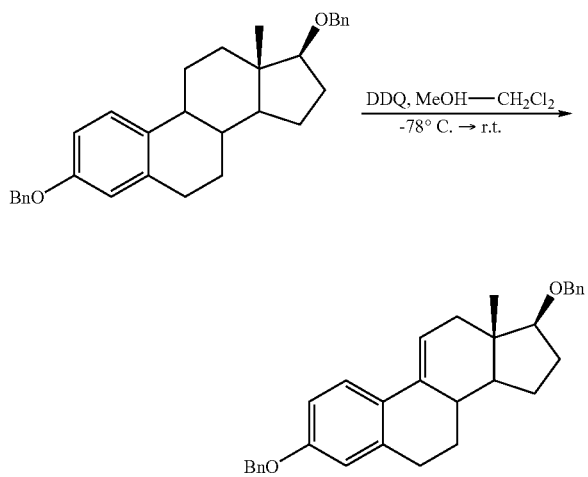

Dichloromethane (0.2 ml) and methanol (0.1 ml) were added to 3,17β-bis(benzyloxy)estra-1,3,5(10)-triene (45.2 mg, 0.1 mmol) under nitrogen atmosphere, followed by cooling to −78° C. 2,3-dichloro-5,6-dicyanobenzoquinone (22.7 mg, 0.1 mmol) was added to the reaction mixture followed by stirring for 10 minutes at −78° C. and then stirred for 3 hours at room temperature. The reaction mixture was quenched with saturated aqueous sodium bicarbonate and extracted with ethyl acetate. The organic layer was washed with water and saturated aqueous sodium chloride, dried over anhydrous magnesium sulfate, and then filtered. The filtrate was concentrated under reduced pressure using an evaporator and the resulting residue was purified by silica gel column chromatography (Merck Kieselgel 60, eluent: hexane/ethyl acetate=10/1→8/1) to give the desired compound 3,17β-bis(benzyloxy)estra-1,3,5(10),9(11)-tetraene (35.7 mg, Yield 80%).

¹H-NMR(300 MHz, CDCl₃): δ 7.54(d, J=9.0 Hz, 1H, C1-CH), 7.27–7.45(m, 10H), 6.80(dd, J=8.7 and 2.7 Hz, 1H, C3-CH), 6.69(d, J=2.4 Hz, 1H, C4-CH), 6.12(m, 1H), 5.05 (s, 2H), 4.56(s, 2H), 4.22(m, 1H), 3.60(t, J=8.7 Hz, 1H), 2.97–2.70(m, 2H), 2.43–1.09(m, 9H), 0.87(s, 3H, C18-CH₃).

(Step 3)

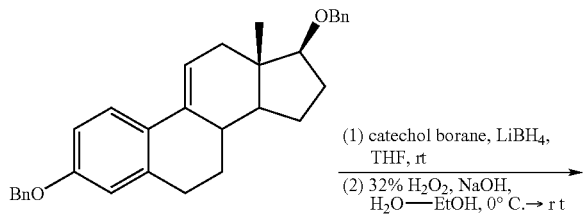

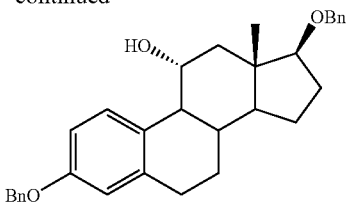

Catecholborane (1.0 M in tetrahydrofuran, 66.33 ml) was added to 3,17β-bis(benzyloxy)estra-1,3,5(10),9(11)-tetraene (27.17 g, 60.30 mmol) at room temperature under nitrogen atmosphere. Lithium borohydride (1.31 g, 60.30 mmol) was further added to the reaction mixture at room temperature, followed by stirring for 10 hours. Under ice-cooling, this mixture was added to a mixture of sodium hydroxide (24.12 g, 603.0 mmol), water (70 ml), ethanol (150 ml) and 30% hydrogen peroxide (150 ml), followed by stirring for 1 hour and 45 minutes on ice and then stirred for 3 hours at room temperature. Ether and water were added to the reaction mixture, which was then extracted with ether. The organic layer was washed sequentially with 10% aqueous sodium hydroxide, water and saturated aqueous sodium chloride, dried over anhydrous magnesium sulfate, and then filtered. The filtrate was concentrated under reduced pressure using an evaporator. The residue was purified by silica gel column chromatography (Merck Kieselgel 60, eluent: hexane/ethyl acetate=6/1→5.5/1) to give the desired compound 3,17β-bis(benzyloxy)estra-1,3,5(10)-trien-11α-ol (21.56 g, Yield 76%).

¹H-NMR(300 MHz, CDCl₃): δ 7.87(d, J=8.4 Hz, 1H, C1-CH), 7.27–7.45(m, 10H), 6.81(dd, J=8.7 and 2.7 Hz, 1H, C3-CH), 6.74(d, J=2.7 Hz, 1H, C4-CH), 5.05(s, 2H), 4.58(s, 2H), 4.22(m, 1H), 3.53(t, J=8.1, 1H), 2.82(m, 2H), 2.43(dd, J=12.2 and 5.4 Hz, 1H), 2.18–2.02(m, 2H), 1.91–1.84(m, 1H), 1.74–1.59(m, 2H), 1.49–1.27(m, 5H), 0.86(s, 3H, C18-CH3).

(Step 4)

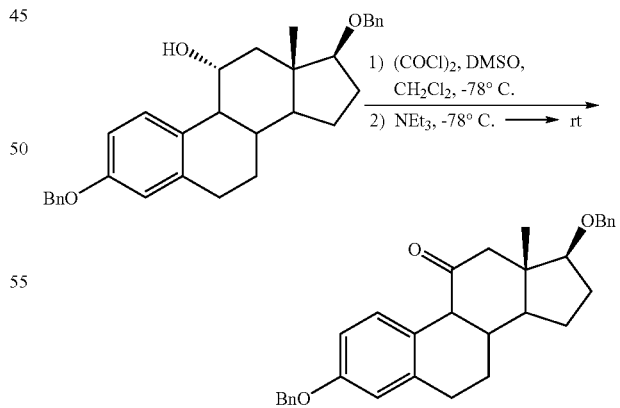

Dichloromethane (92.25 ml) was added to oxalyl dichloride (3.54 ml, 40.59 mmol) under nitrogen atmosphere and the resulting mixture was cooled to −78° C. To this mixture, a solution of dimethyl sulfoxide (5.76 ml, 81.18 mmol) diluted in dichloromethane (18.45 ml) was added dropwise. After the mixture was stirred for 2 minutes at −78° C., a solution of 3,17β-bis(benzyloxy)estra-1,3,5(10)-trien-11α-ol (17.29 g, 36.90 mmol) in dichloromethane (36.90 ml) was added dropwise, followed by stirring for 15 minutes at −78° C. Triethylamine (25.7 ml, 184.5 mmol) was added dropwise to the reaction mixture, which was then stirred for 5 minutes at −78° C. and warmed to room temperature. The reaction mixture was cooled again on ice, quenched by addition of ice and water, and then extracted with dichloromethane. The organic layer was washed with water and saturated aqueous sodium chloride, dried over anhydrous magnesium sulfate, and then filtered. The filtrate was concentrated under reduced pressure using an evaporator to give crude 3,17β-bis(benzyloxy)estra-1,3,5(10)-trien-11-one (crude 18.76 g, quant from crude $^1$H-NMR).

$^1$H-NMR(300 MHz, CDCl$_3$): δ 7.41–7.20(m, 11H), 6.82 (dd, J=8.4 and 2.7 Hz, 1H, C3-CH), 6.70(d, J=2.7 Hz, 1H, C4-CH), 5.03(s, 2H), 4.54(s, 2H), 3.72(t, J=8.1 Hz, 1H), 3.46(d, J=10.2 Hz, 1H), 2.84–2.66(m, 3H), 2.47(d, J=11.4 Hz, 1H), 2.23–2.13(m, 1H), 1.96–1.48(m, 8H), 0.86(s, 3H, C18-CH$_3$).

(Step 5)

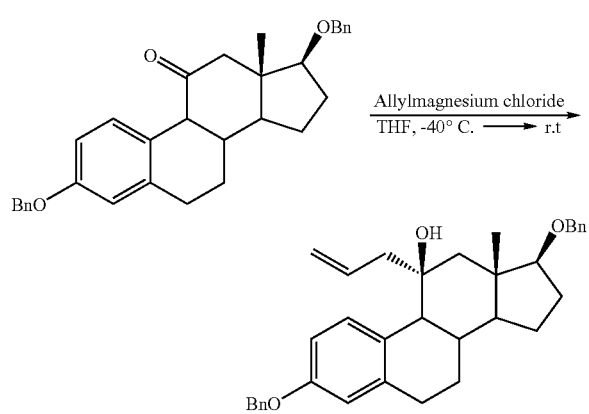

Tetrahydrofuran (280 ml) was added to the crude 3,17β-bis(benzyloxy)estra-1,3,5(10)-trien-11-one (35.7 g, 76.5 mmol) under nitrogen atmosphere, and the resulting mixture was cooled to −40° C. Allylmagnesium chloride (2.0 M in tetrahydrofuran, 50.0 ml, 100 mmol) was added dropwise to the mixture, which was then stirred for 10 minutes at −40° C. and for 1 hour at room temperature. The reaction mixture was cooled again on ice and quenched by addition of ice, water and saturated aqueous ammonium chloride. After the reaction mixture was extracted with ethyl acetate, the organic layer was washed with water and saturated aqueous sodium chloride, dried over anhydrous magnesium sulfate, and then filtered. The filtrate was concentrated under reduced pressure using an evaporator and hexane was added to the resulting residue to precipitate solids. The solids were collected by filtration and vacuum dried to give 3,17β-bis(benzyloxy)-11α-(2-propenyl)estra-1,3,5(10)-trien-11β-ol (35.81 g, Yield 90% from 3,17β-bis(benzyloxy)estra-1,3,5(10)-trien-11α-ol).

$^1$H-NMR (300 MHz, CDCl$_3$): d 7.82 (d, J=9.6 Hz, 1H, C1-H), 7.44–7.33 (m, 10H), 6.83–6.79 (m, 2H, C2 and C4-H), 6.01–5.87 (m, 1H, olefin-H), 5.21–5.13 (m, 2H, olefin-H), 5.06 (s, 2H), 4.57 (s, 2H), 3.46 (t, J=8.7 Hz, 1H, C17-H), 2.90 (dd, J=14.0 and 8.4 Hz, 1H, allylic-CH$_2$), 2.74–2.63 (m, 2H), 2.52 (dd, J=14.1 and 7.0 Hz, 1H, allylic-CH$_2$), 2.25 (d, J=10.8 Hz, 1H), 2.13 (d, J=14.1 Hz, 1H), 2.06–1.98 (m, 1H), 1.88–1.14 (m, 9H), 1.09(s, 3H, C18-H).

(Step 6)

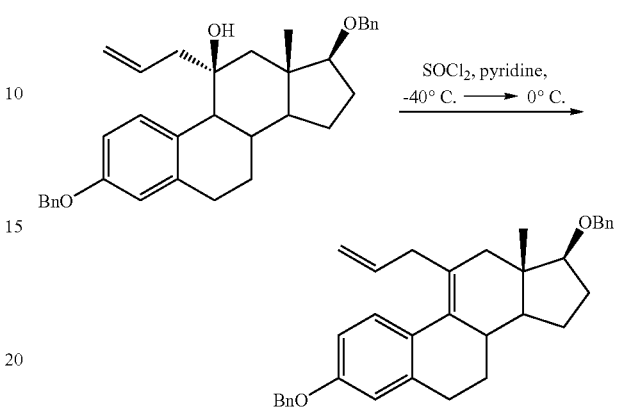

After a solution of 3,17β-bis(benzyloxy)-11α-(2-propenyl)estra-1,3,5(10)-trien-11β-ol (17.20 g, 33.80 mmol) in pyridine (135 ml) was cooled to −40° C. under nitrogen atmosphere, thionyl chloride (3.7 ml, 50.7 mmol) was added dropwise to the solution, which was then stirred for 10 minutes at −40° C. and for 1 hour on ice. The reaction mixture was quenched by addition of ice and water and then extracted with a mixed solvent of hexane and t-butyl methyl ether (hexane/t-butyl methyl ether=4/1). The organic layer was washed with water and saturated aqueous sodium chloride, dried over anhydrous magnesium sulfate, and then filtered. The filtrate was concentrated under reduced pressure using an evaporator and the resulting residue was triturated with methanol to precipitate solids. The solids were collected by filtration and vacuum dried to give 3,17β-bis(benzyloxy)-11-(2-propenyl)estra-1,3,5(10),9(11)-tetraene (14.92 g, Yield 90%).

$^1$H-NMR (300 MHz, CDCl$_3$): d 7.46–7.25 (m, 11H), 6.78–6.75 (m, 2H, C2 and C4-H), 6.01–5.89 (m, 1H, olefin-H), 5.18–5.09 (m, 2H, olefin-H), 5.06 (s, 2H), 4.58 (s, 2H), 3.58 (t, J=8.4 Hz, 1H, C17-H), 3.30 (dd, J=15.8 and 5.1 Hz, 1H, allylic-CH$_2$), 2.81–2.72 (m, 3H), 2.48 (d, J=17.4 Hz, 1H, allylic-CH$_2$), 2.16–1.36 (m, 9H), 0.90 (s, 3H, C18-H).

(Step 7)

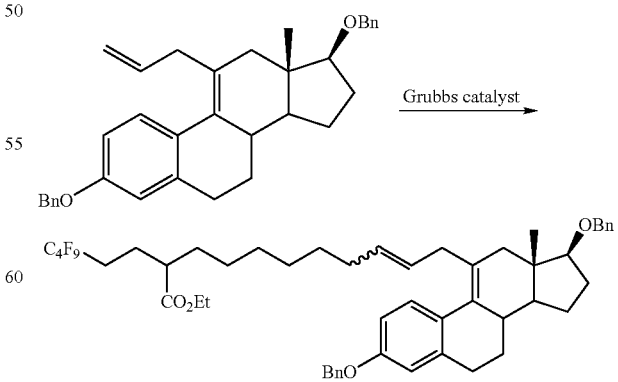

Benzylidenebis(tricyclohexylphosphine)-dichlororuthenium (90 mg, 0.1 mmol) was added to a solution of 3,17β-bis(benzyloxy)-11-(2-propenyl)estra-1,3,5(10),9(11)-tetraene (1.0 g, 2.0 mmol) and ethyl 2-(3,3,4,4,5,5,6,6,6-nonafluorohexyl)-9-decenoate (1.81 g, 4.1 mmol) in dichloromethane (20 ml), followed by heating under reflux for 5 hours under nitrogen atmosphere. After cooling, the reaction mixture was concentrated under reduced pressure and the resulting residue was purified by silica gel flash chromatography (eluent: hexane/ethyl acetate=4/1) to give ethyl 11-[3,17β-bis(benzyloxy)estra-1,3,5(10),9(11)-tetraen-11-yl]-2-(3,3,4,4,5,5,6,6,6-nonafluorohexyl)-9-undecenoate (863 mg, Yield 48%).

¹H-NMR(270 MHz, CDCl₃): δ 7.46–7.21 (m, 11H), 6.78–6.73(m, 2H), 5.50–5.42(m, 2H), 5.05(s, 2H), 4.57(d, J=2.5 Hz, 2H), 4.15(q, J=7.1 Hz, 2H, COO—CH₂), 3.60–3.52(m, 1H, C17-CH), 3.20–3.11(m, 1H), 2.82–2.68 (m, 3H), 2.51–2.22(m, 2H), 2.20–1.16(m, 28H), 0.87(s, 3H, C18-CH₃).

(Step 8)

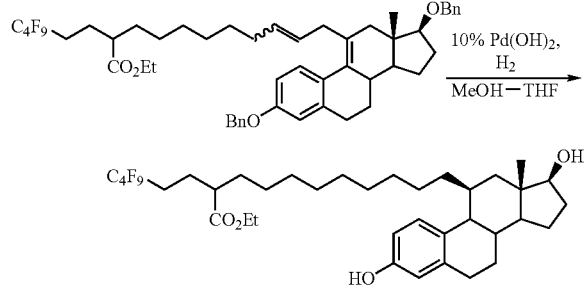

Ethyl 11-[3,17β-bis(benzyloxy)estra-1,3,5(10),9(11)-tetraen-11-yl]-2-(3,3,4,4,5,5,6,6,6-nonafluorohexyl)-9-undecenoate (500 mg, 0.55 mmol) was dissolved in a mixed solvent of methanol (10 ml) and tetrahydrofuran (1 ml), followed by addition of palladium hydroxide/carbon (150 mg) at room temperature. After purging with hydrogen, the reaction mixture was stirred for 23 hours at room temperature and then filtered. The solvent was concentrated under reduced pressure and the resulting residue was purified by silica gel column chromatography (hexane/ethyl acetate=4/1→3/1→2/1) to give ethyl 11-(3,17β-dihydroxyestra-1,3,5(10)-trien-11β-yl)-2-(3,3,4,4,5,5,6,6,6-nonafluorohexyl)undecanoate (287 mg, Yield 71%).

¹H-NMR(270 MHz, CDCl₃): δ 7.00(d, J=8.6 Hz, 1H, C1-CH), 6.62(d, J=8.5 Hz, 1H, C2-CH), 6.54(d, J=2.3 Hz, 1H, C4-CH), 5.03(brs, 1H, C3-OH), 4.17(q, J=7.1 Hz, 2H, COO—CH₂), 3.70(t, J=7.9 Hz, 1H, C17-CH), 2.83–2.60(m, 2H), 2.58–2.30(m, 3H), 2.24–1.74(m, 7H), 1.74–1.11(m, 29H), 0.92(s, 3H, C18-CH₃).

(Step 9)

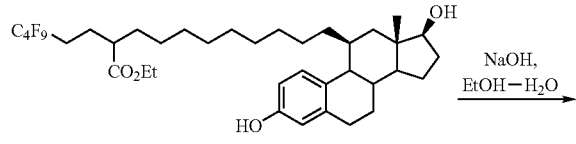

-continued

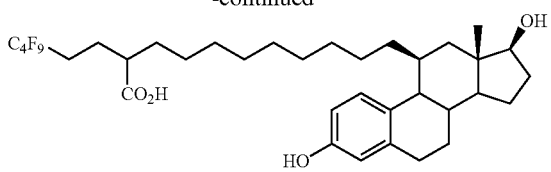

Ethyl 11-(3,17β-dihydroxyestra-1,3,5(10)-trien-11β-yl)-2-(3,3,4,4,5,5,6,6,6-nonafluorohexyl)undecanoate (747 mg, 1.02 mmol) was dissolved in a mixed solvent of ethanol (5 ml) and water (5 ml). To this solution, NaOH (82 mg, 2.04 mmol) was added, and the resulting mixture was heated for 15 hours at 60° C. After cooling, 2N aqueous hydrochloric acid was added to the reaction mixture, which was then extracted with ethyl acetate. The organic layer was washed with saturated aqueous sodium chloride, dried over anhydrous sodium sulfate, and then filtered. After concentration under reduced pressure, the resulting residue was purified by silica gel column chromatography (hexane/ethyl acetate=4/1→3/1→2/1) to give 11-(3,17β-dihydroxyestra-1,3,5(10)-trien-11β-yl)-2-(3,3,4,4,5,5,6,6,6-nonafluorohexyl)undecanoic acid (600 mg, Yield 84%).

¹H-NMR(270 MHz, CD₃OD): δ 6.95(d, J=8.3 Hz, 1H, C1-CH), 6.55(dd, J=8.3, 2.3 Hz, 1H, C2-CH), 6.47(d, J=2.3 Hz, 1H, C4-CH), 3.63(t, J=8.6 Hz, 1H, C17-CH), 2.85–2.58 (m, 2H), 2.55–2.34(m, 3H), 2.30–1.93(m, 2H), 1.91–1.75 (m, 3H), 1.75–1.10(m, 26H), 0.92(s, 3H, C18-CH3).

Example 21

Synthesis of 10-(3,17β-dihydroxyestra-1,3,5(10)-trien-11β-yl)-2-(4,4,5,5,5-pentafluoropentyl)decanoic acid

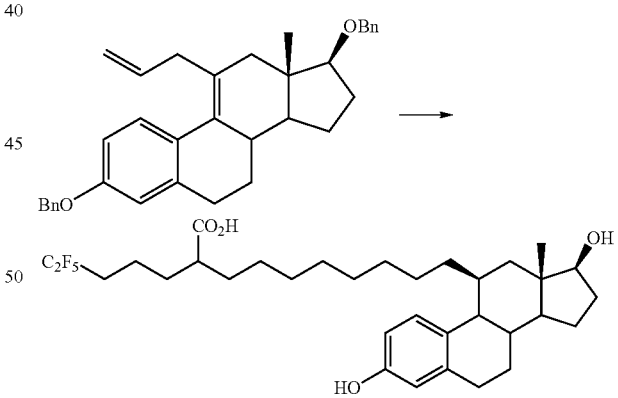

Starting with the 3,17β-bis(benzyloxy)-11-(2-propenyl)estra-1,3,5(10),9(11)-tetraene prepared in Example 20 and ethyl 2-(4,4,5,5,5-pentafluoro-pentyl)-8-nonenoate prepared separately, the same procedure as shown in Example 20 was repeated to give 10-(3,17β-dihydroxyestra-1,3,5(10)-trien-11β-yl)-2-(4,4,5,5,5-pentafluoropentyl)decanoic acid.

¹H-NMR(300 MHz, CDCl₃): (6.99(d, J=8.7 Hz, 1H, C1-CH), 6.62(d, J=8.2 Hz, 1H, C2-CH), 6.55(d, J=2.3 Hz, 1H, C4-CH), 4.87–3.82(brs, 1H, C3-OH), 3.73(t, J=7.4 Hz, 1H, C17-CH), 2.84–2.65(m, 2H), 2.51(m, 1H), 2.39(m, 2H), 2.24–1.12(m, 32H), 0.91(s, 3H, C18-CH₃).

Example 22

Synthesis of 10-(3,17β-dihydroxyestra-1,3,5(10)-trien-11β-yl)-2-(4,4,5,5,6,6,7,7,7-nonafluoroheptyl)decanoic acid

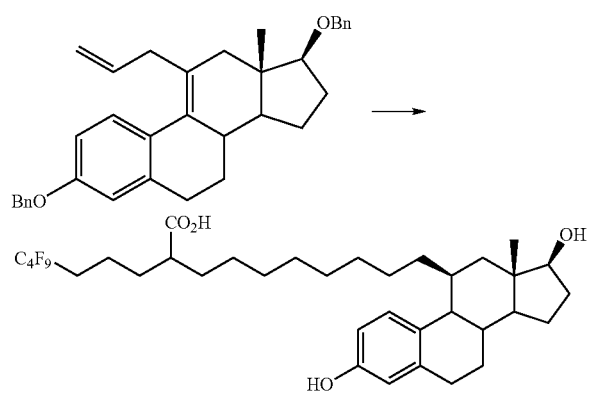

Starting with the 3,17β-bis(benzyloxy)-11-(2-propenyl)estra-1,3,5(10),9(11)-tetraene prepared in Example 20 and ethyl 2-(4,4,5,5,6,6,7,7,7-nonafluoroheptyl)-8-nonenoate prepared separately, the same procedure as shown in Example 20 was repeated to give 10-(3,17β-dihydroxyestra-1,3,5(10)-trien-11β-yl)-2-(4,4,5,5,6,6,7,7,7-nonafluoroheptyl)decanoic acid.

$^1$H-NMR(300 MHz, CDCl$_3$): (7.11(d, J=8.3 Hz, 1H, C1-CH), 6.62(d, J=8.6 Hz, 1H, C2-CH), 6.54(d, J=2.7 Hz, 1H, C4-CH), 3.94–3.07(brs, 1H, C3-OH), 3.72(t, J=7.4 Hz, 1H, C17-CH), 2.82–2.62(m, 2H), 2.52(m, 1H), 2.40(m, 2H), 2.23–1.11(m, 32H), 0.91(s, 3H, C18-CH$_3$)

Example 23

Synthesis of 10-(3,17β-dihydroxyestra-1,3,5(10)-trien-11β-yl)-2-(3,3,4,4,5,5,6,6,6-nonafluorohexyl)decanoic acid

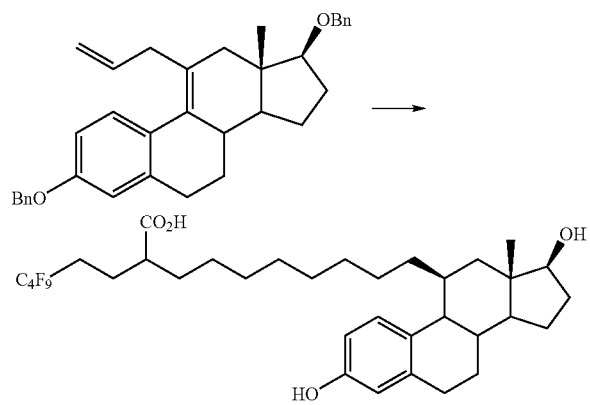

Starting with the 3,17β-bis(benzyloxy)-11-(2-propenyl)estra-1,3,5(10),9(11)-tetraene prepared in Example 20 and ethyl 2-(3,3,4,4,5,5,6,6,6-nonafluorohexyl)-8-nonenoate prepared separately, the same procedure as shown in Example 20 was repeated to give 10-(3,17β-dihydroxyestra-1,3,5(10)-trien-11β-yl)-2-(3,3,4,4,5,5,6,6,6-nonafluorohexyl)decanoic acid.

$^1$H-NMR (300 MHz; CDCl$_3$): (=7.07(d, J=8.5 Hz, 1H), 6.65(dd; J=8.2, 2.1 Hz, 1H), 6.47(d, J=2.6 Hz, 1H), 3.82(t, J=8.2 Hz, 1H), 2.91–2.58(m, 2H), 2.53–2.23(m, 3H), 2.19–1.89(m, 4H), 1.85–1.02(m, 26H), 0.92(s, 3H).

Example 24

Synthesis of 11-(3,17β-dihydroxyestra-1,3,5(10)-trien-11β-yl)-2-(4,4,5,5,5-pentafluoropentyl)undecanoic acid

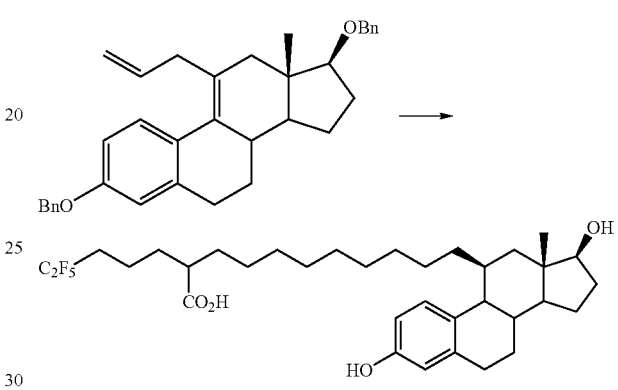

Starting with the 3,17β-bis(benzyloxy)-11-(2-propenyl)estra-1,3,5(10),9(11)-tetraene prepared in Example 20 and ethyl 2-(4,4,5,5,5-pentafluoro-pentyl)-9-decenoate prepared separately, the same procedure as shown in Example 20 was repeated to give 11-(3,17β-dihydroxyestra-1,3,5(10)-trien-11β-yl)-2-(4,4,5,5,5-pentafluoropentyl)undecanoic acid.

$^1$H-NMR (270 MHz; CDCl$_3$): (7.00(d, J=8.4 Hz, 1H), 6.59(dd, J=8.7, 2.7 Hz, 1H), 6.54(d, J=2.7 Hz, 1H), 3.73–3.71(m, 1H), 2.88–2.82(m, 2H), 2.58–2.33(m, 3H), 2.24–1.18(m, 34H), 0.92(s, 3H).

Example 25

Synthesis of 11-(3,17β-dihydroxyestra-1,3,5(10)-trien-11β-yl)-2-(4,4,5,5,6,6,7,7,7-nonafluoroheptyl)undecanoic acid

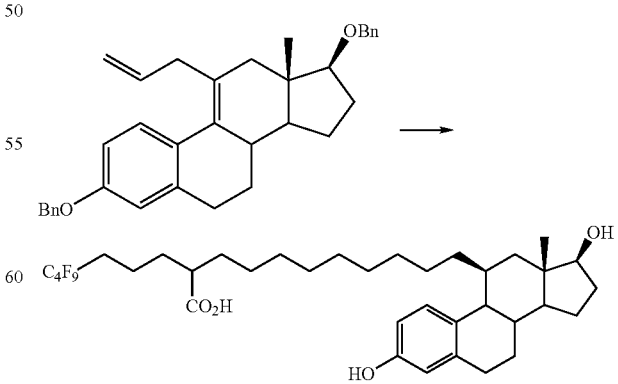

Starting with the 3,17β-bis(benzyloxy)-11-(2-propenyl)estra-1,3,5(10),9(11)-tetraene prepared in Example 20 and ethyl 2-(4,4,5,5,6,6,7,7,7-nonafluoroheptyl)-9-decenoate prepared separately, the same procedure as shown in Example 20 was repeated to give 11-(3,17β-dihydroxyestra-1,3,5(10)-trien-11β-yl)-2-(4,4,5,5,6,6,7,7,7-nonafluoroheptyl)undecanoic acid.

$^1$H-NMR(270 MHz, CD$_3$OD): δ 7.07(d, J=8.4 Hz, 1H, C1-CH), 6.54 (dd, J=8.4, 2.3 Hz, 1H, C2-CH), 6.45(d, J=2.3 Hz, 1H, C4-CH), 3.67(t, J=8.3 Hz, 1H, C17-CH), 2.85–2.62 (m, 2H), 2.05–1.80(m, 7H), 1.80–0.96(m, 32H), 0.91(s, 3H, C18-CH$_3$)

Example 26

Synthesis of 10-(3,17β-dihydroxyestra-1,3,5(10)-trien-11β-yl)-2-(6,6,7,7,7-pentafluoroheptyl)decanoic acid

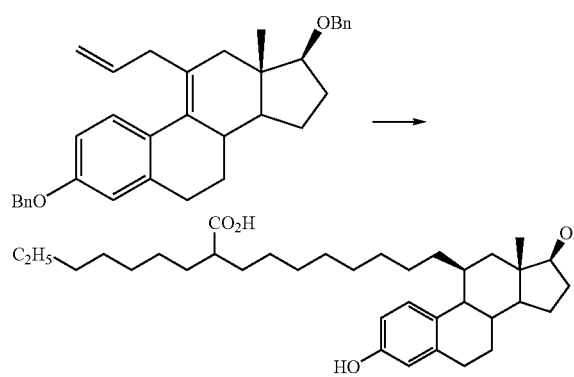

The 10-(3,17β-dihydroxyestra-1,3,5(10)-trien-11β-yl)-2-(6,6,7,7,7-pentafluoroheptyl)decanoic acid prepared in Example 12 could also be synthesized by a procedure analogous to Example 20, starting with 3,17β-bis(benzyloxy)-11-(2-propenyl)estra-1,3,5(10),9(11)-tetraene and separately prepared ethyl 2-(6,6,7,7,7-pentafluoroheptyl)-8-nonenoate.

Example 27

Synthesis of 12-[6-hydroxy-2-(4-hydroxyphenyl)naphth-1-yl]-2-(4,4,5,5,5-pentafluoropentyl)dodecanoic acid

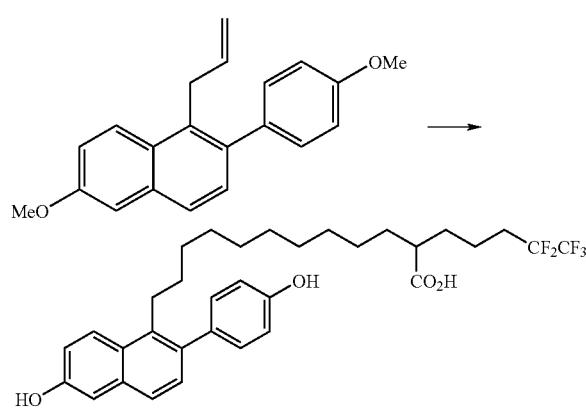

Starting with 6-methoxy-2-(4-methoxyphenyl)-1-(2-propenyl)naphthalene and separately prepared diethyl 2-(8-nonenyl)-2-(4,4,5,5,5-pentafluoropentyl)malonate, the same procedures as shown in Examples 1, 2 and 3 were repeated to give 12-[6-hydroxy-2-(4-hydroxyphenyl)naphth-1-yl]-2-(4,4,5,5,5-pentafluoropentyl)dodecanoic acid.

$^1$H-NMR(270 MHz, CDCl$_3$): δ 7.98 (d, J=9 Hz, 1H, Ar—H), 7.53 (d, J=8 Hz, 1H, Ar—H), 7.28–7.12 (m, 5H, Ar—H), 6.89 (d, J=9 Hz, 2H, Ar—H), 2.96–2.90 (m, 2H, naphtyl-CH$_2$—), 2.44–2.42 (m, 1H, —CHCO$_2$), 2.18–1.18 (m, 24H, alkyl-H).

Example 28

Synthesis of 11-[6-hydroxy-2-(4-hydroxyphenyl)naphth-1-yl]-2-(3,3,4,4,5,5,6,6,6-nonafluorohexyl)undecanoic acid

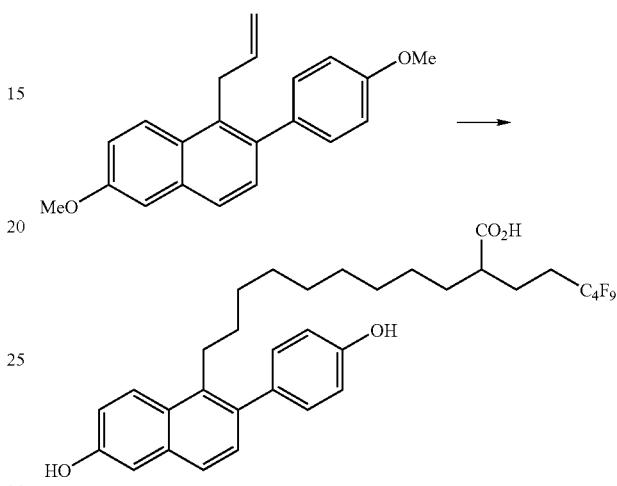

Starting with 6-methoxy-2-(4-methoxyphenyl)-1-(2-propenyl)naphthalene and separately prepared diethyl 2-(7-octenyl)-2-(3,3,4,4,5,5,6,6,6-nonafluorohexyl)malonate, the same procedures as shown in Examples 1, 2 and 3 were repeated to give 11-[6-hydroxy-2-(4-hydroxyphenyl)naphth-1-yl]-2-(3,3,4,4,5,5,6,6,6-nonafluorohexyl)undecanoic acid.

$^1$H-NMR(300 MHz, CDCl$_3$): δ 7.98(d, J=8.9 Hz, 1H, Ar—H), 7.53 (d, J=8.4 Hz, 1H, Ar—H), 7.13–7.28(m, 5H, Ar—H), 6.89(d, J=8.5 Hz, 2H, Ar—H), 2.92(t, J=8.1 Hz, 2H, naphthyl-CH$_2$), 2.46–2.48(m, 1H, CHCO$_2$H), 1.95–2.20 (m, 2H, CH$_2$CF$_2$), 1.18–2.11(m, 18H, alkyl-H)

Mass(ESI): 667(M+1)

Example 29

Synthesis of 12-[6-hydroxy-2-(4-hydroxy-2-methylphenyl)-naphth-1-yl]-2-(4,4,5,5,5-pentafluoropentyl)dodecanoic acid

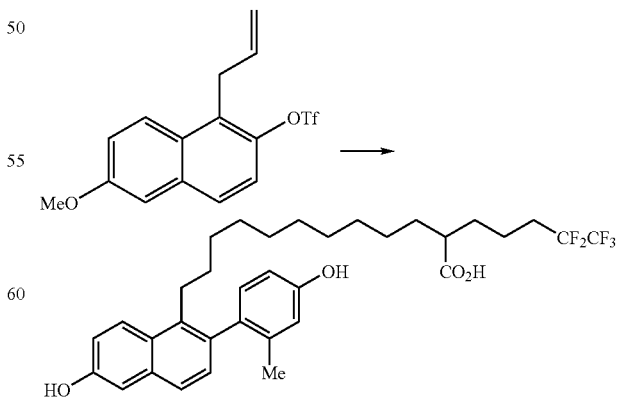

Starting with the 6-methoxy 1-(2-propenyl)-2-naphthyl trifluoromethanesulfonate prepared in Example 1 and 4-methoxy-2-methylphenylboronic acid prepared separately, the same procedures as shown in Examples 1, 2 and 3 were repeated to give 12-[6-hydroxy-2-(4-hydroxy-2-methylphenyl)naphth-1-yl]-2-(4,4,5,5,5-pentafluoropentyl)dodecanoic acid.

$^1$H-NMR(270 MHz, CDCl$_3$): δ 7.97 (d, J=8.9 Hz, 1H), 7.53 (d, J=8.4 Hz, 1H), 7.19–7.10 (m, 3H), 7.02 (d, J=8.3 Hz, 1H), 6.77 (d, J=2.1 Hz, 1H), 6.70 (dd, J=8.3, 2.1 Hz, 1H), 4.8 (br, 3H), 3.0–2.8 (m, 1H), 2.7–2.5 (m, 1H), 2.5–2.3 (m, 1H), 2.1–1.9 (m, 2H), 1.99 (s, 3H, CH3), 1.8–1.0 (m, 22H).

Example 30

Synthesis of 12-[2-(2-ethyl-4-hydroxyphenyl)-6-hydroxynaphth-1-yl]-2-(4,4,5,5,5-pentafluoropentyl)dodecanoic acid

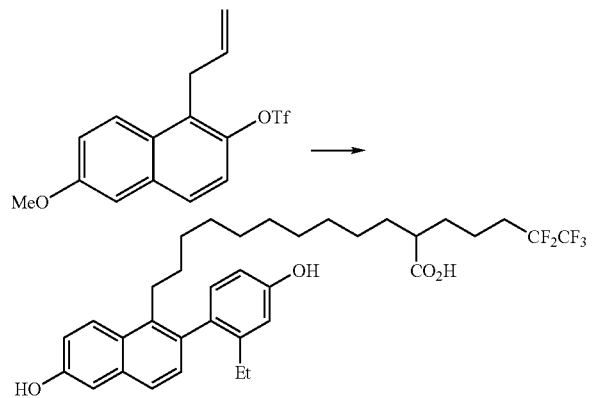

Starting with the 6-methoxy 1-(2-propenyl)-2-naphthyl trifluoromethanesulfonate prepared in Example 1 and 2-ethyl-4-methoxyphenylboronic acid prepared separately, the same procedures as shown in Examples 1, 2 and 3 were repeated to give 12-[2-(2-ethyl-4-hydroxyphenyl)-6-hydroxynaphth-1-yl]-2-(4,4,5,5,5-pentafluoropentyl)dodecanoic acid.

$^1$H-NMR(300 MHz, CDCl$_3$): δ 7.97 (d, J=9.1 Hz, 1H, Ar—H), 7.52(d, J=8.4 Hz, 1H, Ar—H), 7.06–7.23(m, 3H, Ar—H), 6.85(d, J=8.2 Hz, 1H, Ar—H), 6.79(d, J=2.6 Hz, 1H, Ar—H), 6.61(dd, J=8.2, 2.6 Hz, 1H, Ar—H), 2.81–2.93 (m, 1H, naphthyl-CH$_2$), 2.49–2.75(m, 1H, naphthyl-CH$_2$), 2.39–2.50(m, 1H, CHCO$_2$H), 2.18–2.29(m, 2H, ArCH$_2$CH$_3$), 1.91–2.12(m, 2H, CH$_2$CF$_2$), 0.95–1.72(m, 25H, alkyl-H)

Mass(ESI): 623(M+1)

Example 31

Synthesis of 12-[2-(2-fluoro-4-hydroxyphenyl)-6-hydroxynaphth-1-yl]-2-(4,4,5,5,5-pentafluoropentyl)dodecanoic acid

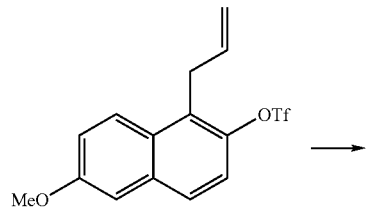

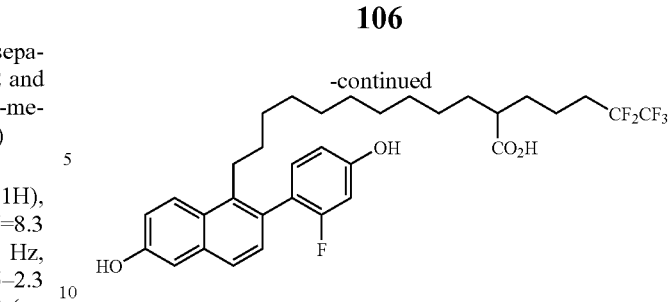

Starting with the 6-methoxy 1-(2-propenyl)-2-naphthyl trifluoromethanesulfonate prepared in Example 1 and 2-fluoro-4-methoxyphenylboronic acid prepared separately, the same procedures as shown in Examples 1, 2 and 3 were repeated to give 12-[2-(2-fluoro-4-hydroxyphenyl)-6-hydroxynaphth-1-yl]-2-(4,4,5,5,5-pentafluoropentyl)dodecanoic acid.

$^1$H-NMR(300 MHz, CDCl$_3$): δ 7.97(d, J=9.1 Hz, 1H, Ar—H), 7.52(d, J=8.5 Hz, 1H, Ar—H), 7.06–7.25(m, 4H, Ar—H), 6.64–6.69(m, 2H, Ar—H), 2.81–2.90(m, 2H, naphthyl-CH$_2$), 2.40–2.50(m, 1H, CHCO$_2$H), 1.90–2.10(m, 2H, CH$_2$CF$_2$), 1.05–1.75(m, 22H, alkyl-H)

Mass(ESI): 613 (M+1)

Example 32

Synthesis of 12-[6-hydroxy-2-(4-hydroxy-2-trifluoromethyl-phenyl)naphth-1-yl]-2-(4,4,5,5,5-pentafluoropentyl)dodecanoic acid

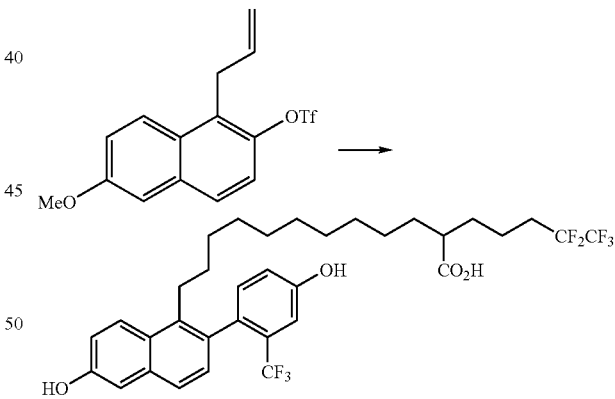

Starting with the 6-methoxy 1-(2-propenyl)-2-naphthyl trifluoromethanesulfonate prepared in Example 1 and 4-methoxy-2-trifluoromethylphenylboronic acid prepared separately, the same procedures as shown in Examples 1, 2 and 3 were repeated to give 12-[6-hydroxy-2-(4-hydroxy-2-trifluoromethylphenyl)naphth-1-yl]-2-(4,4,5,5,5-pentafluoropentyl)dodecanoic acid.

$^1$H-NMR(270 MHz, CDCl$_3$): δ 7.96 (d, J=9 Hz, 1H, Ar—H), 7.50 (d, J=8 Hz, 1H, Ar—H), 7.24–7.01 (m, 6H, Ar—H), 2.89–2.84 (m, 1H), 2.51–2.42 (m, 2H), 2.11–1.15 (m, 24H, alkyl-H).

Example 33

Synthesis of 12-[2-(3-fluoro-4-hydroxyphenyl)-6-hydroxynaphth-1-yl]-2-(4,4,5,5,5-pentafluoropentyl) dodecanoic acid

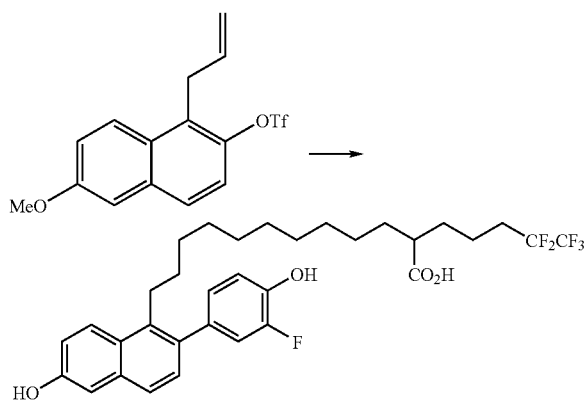

Starting with the 6-methoxy 1-(2-propenyl)-2-naphthyl trifluoromethanesulfonate prepared in Example 1 and 3-fluoro-4-methoxyphenylboronic acid prepared separately, the same procedures as shown in Examples 1, 2 and 3 were repeated to give 12-[2-(3-fluoro-4-hydroxyphenyl)-6-hydroxynaphth-1-yl]-2-(4,4,5,5,5-pentafluoropentyl)dodecanoic acid.

$^1$H-NMR(270 MHz, CDCl$_3$): δ 7.96 (d, J=9 Hz, 1H, Ar—H), 7.51 (d, J=8 Hz, 1H, Ar—H), 7.24–6.95 (m, 6H, Ar—H), 2.94–2.88 (m, 2H, naphtyl-CH$_2$—), 2.39 (m, 1H, —CHCO$_2$), 2.16–1.18 (m, 24H, alkyl-H).

Example 34

Synthesis of 12-[2-(3,5-difluoro-4-hydroxyphenyl)-6-hydroxynaphth-1-yl]-2-(4,4,5,5,5-pentafluoropentyl)dodecanoic acid

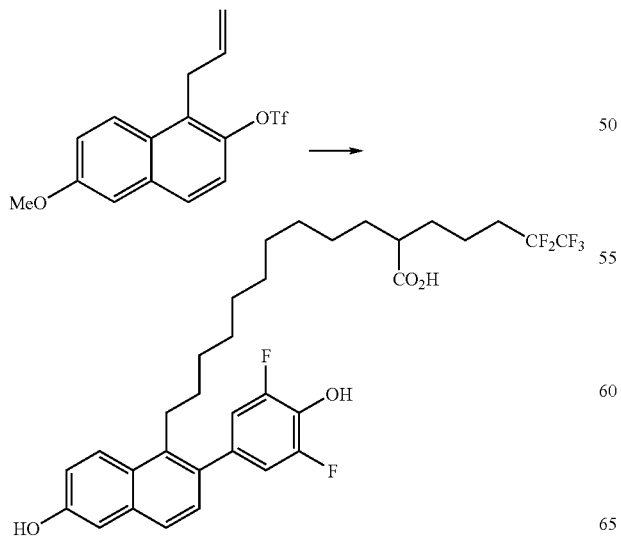

Starting with the 6-methoxy 1-(2-propenyl)-2-naphthyl trifluoromethanesulfonate prepared in Example 1 and 3,5-difluoro-4-methoxyphenylboronic acid prepared separately, the same procedures as shown in Examples 1, 2 and 3 were repeated to give 12-[2-(3,5-difluoro-4-hydroxyphenyl)-6-hydroxynaphth-1-yl]-2-(4,4,5,5,5-pentafluoropentyl)dodecanoic acid.

$^1$H-NMR(300 MHz, CDCl$_3$): δ 7.98(d, J=9.9 Hz, 1H, Ar—H), 7.53(d, J=8.5 Hz, 1H, Ar—H), 7.14–7.26(m, 3H, Ar—H), 6.85–6.90(m, 2H, Ar—H), 2.88–2.94(m, 2H, naphthyl-CH$_2$), 2.39–2.48(m, 1H, CHCO$_2$H), 2.01–2.12(m, 2H, CH$_2$CF$_2$), 1.24–1.88(m, 21H, alkyl-H).

Mass(ESI): 631(M+1)

Example 35

Synthesis of 12-[2-(4-fluorophenyl)-6-hydroxynaphth-1-yl]2-(4,4,5,5,5-pentafluoropentyl)dodecanoic acid

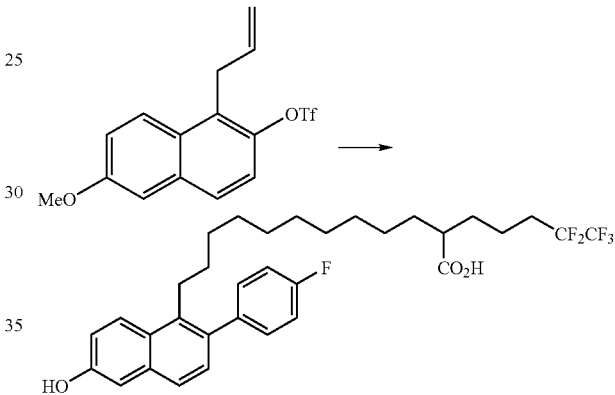

Starting with the 6-methoxy 1-(2-propenyl)-2-naphthyl trifluoromethanesulfonate prepared in Example 1 and 4-fluorophenylboronic acid prepared separately, the same procedures as shown in Examples 1, 2 and 3 were repeated to give 12-[2-(4-fluorophenyl)-6-hydroxynaphth-1-yl]-2-(4,4,5,5,5-pentafluoropentyl)dodecanoic acid.

$^1$H-NMR(270 MHz, CDCl$_3$): δ 7.98 (d, J=9 Hz, 1H, Ar—H), 7.54 (d, J=8 Hz, 1H, Ar—H), 7.31–7.07 (m, 7H, Ar—H), 2.93–2.87 (m, 2H, naphtyl-CH$_2$—), 2.46–2.35 (m, 1H, —CHCO$_2$), 2.15–1.14 (m, 24H, alkyl-H).

Example 36

Synthesis of (2R)-11-(3,17β-dihydroxyestra-1,3,5(10)-trien-7α-yl)-2-(3,3,4,4,5,5,6,6,6-nonafluorohexyl)undecanoic acid (Step 1)

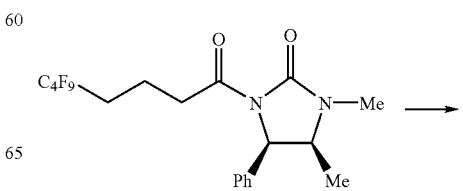

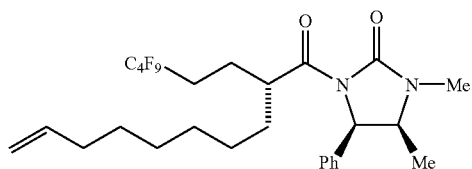

Anhydrous tetrahydrofuran (10 ml) was added to (4S,5R)-3,4-dimethyl-1-(5,5,6,6,7,7,8,8,8-nonafluorooctanoyl)-5-phenylimidazolidin-2-one (1.20 g, 2.5 mmol) under nitrogen atmosphere, and the resulting mixture was cooled to −78° C. Lithium bis(trimethylsilyl)amide (2.75 ml, 1.0 M in tetrahydrofuran, 2.75 mmol) was added to the mixture, which was then stirred for 1 hour. After addition of 8-bromo-1-octene (714 mg, 3.0 mmol) and HMPA (1.25 ml) at −78° C., the reaction mixture was warmed with stirring up to −50° C. over 2 hours and up to 0° C. over 30 minutes, and then stirred for 12 hours at 0° C. The reaction mixture was quenched with saturated aqueous ammonium chloride at 0° C., and then extracted with a mixed solvent of ethyl acetate and n-hexane (3:7). The organic layer was washed sequentially with saturated aqueous potassium bisulfate, saturated aqueous sodium chloride, saturated aqueous sodium bicarbonate and saturated aqueous sodium chloride, dried over anhydrous magnesium sulfate, and then filtered. The filtrate was concentrated under reduced pressure using an evaporator and the resulting residue was purified by silica gel column chromatography (Kanto Kagaku, silica gel 60 (spherical, neutral), 40–100 μm, eluent: ethyl acetate/n-hexane=1/5 3/7) to give (4S,5R)-3,4-dimethyl-1-[(2R)-2-(3,3,4,4,5,5,6,6,6-nonafluorohexyl)-9-decenoyl]-5-phenylimidazolidin-2-one (1.37 g, Yield 93%).

Optical purity: 95.5% de, as measured by HPLC (column: Daicel Chiralpack AD, φ0.46×25 cm, solvent: n-hexane/isopropanol=97/3, flow rate: 0.5 ml/min, detection wavelength: 206 nm)

$^1$H-NMR(270 MHz, CDCl$_3$): δ 7.32–7.13 (m, 5H), 5.87–5.72 (m, 1H), 5.34(d, J=8.9 Hz, 1H), 5.02–4.91 (m, 2H), 4.10–3.86 (m, 2H), 2.84 (s, 3H), 2.19–1.08 (m, 16H), 0.82 (d, J=6.5 Hz, 3H).

(Step 2)

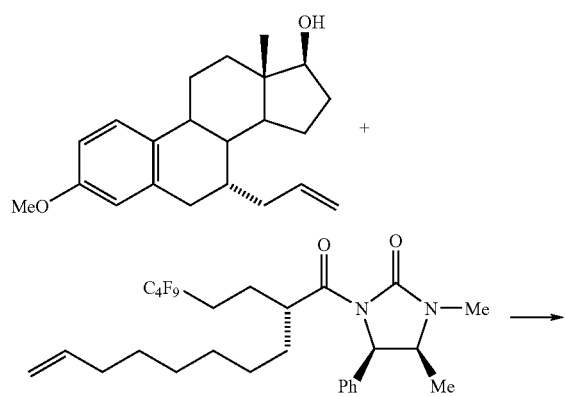

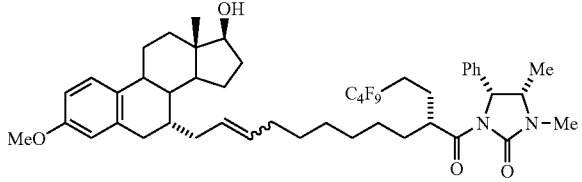

3-Methoxy-7α-(2-propenyl)estra-1,3,5(10)-trien-17β-ol (377 mg, 1.16 mmol) and (4S,5R)-3,4-dimethyl-1-[(2R)-2-(3,3,4,4,5,5,6,6,6-nonafluorohexyl)-9-decenoyl]-5-phenylimidazolidin-2-one (1.36 g, 2.31 mmol) were dissolved in anhydrous dichloromethane (12 ml) at room temperature under nitrogen atmosphere. To this solution, benzylidenebis(tricyclohexylphosphine)dichlororuthenium (47.5 mg, 5.78×10$^{-2}$ mmol) was added, and the resulting mixture was heated under reflux for 5 hours under nitrogen atmosphere. After cooling, the reaction mixture was filtered through an alumina pad. The filtrate was concentrated under reduced pressure and the resulting residue was purified by silica gel flash chromatography (Kanto Kagaku, silica gel 60 (spherical, neutral), 40–100 μm, eluent: ethyl acetate/n-hexane=1/1) to give a mixture of (4S,5R)-3,4-dimethyl-1-[(2R,9E)-11-(17β-hydroxy-3-methoxyestra-1,3,5(10)-trien-7α-yl)-2-(3,3,4,4,5,5,6,6,6-nonafluorohexyl)-9-undecenoyl]-5-phenylimidazolidin-2-one and (4S,5R)-3,4-dimethyl-1-[(2R,9Z)-11-(17β-hydroxy-3-methoxyestra-1,3,5(10)-trien-7α-yl)-2-(3,3,4,4,5,5,6,6,6-nonafluorohexyl)-9-undecenoyl]-5-phenylimidazolidin-2-one (579 mg, Yield 57%).

$^1$H-NMR(300 MHz, CDCl$_3$): δ 7.33–7.12 (m, 6H), 6.73–6.69 (m, 1H), 6.61–6.56 (m, 1H), 5.42–5.25 (m, 3H), 4.05–3.87 (m, 2H), 3.77–3.70 (m, 4H), 2.90–2.71 (m, 5H), 2.38–1.06 (m, 31H), 0.83–0.78 (m, 6H).

(Step 3)

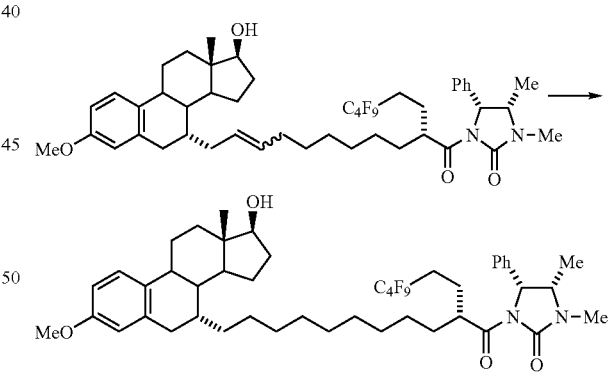

The mixture of (4S,5R)-3,4-dimethyl-1-[(2R,9E)-11-(17β-hydroxy-3-methoxyestra-1,3,5(10)-trien-7α-yl)-2-(3,3,4,4,5,5,6,6,6-nonafluorohexyl)-9-undecenoyl]-5-phenylimidazolidin-2-one and (4S,5R)-3,4-dimethyl-1-[(2R,9Z)-11-(17β-hydroxy-3-methoxyestra-1,3,5(10)-trien-7α-yl)-2-(3,3,4,4,5,5,6,6,6-nonafluorohexyl)-9-undecenoyl]-5-phenylimidazolidin-2-one (579 mg, 653 μmol) was dissolved in ethyl acetate (14 ml), followed by addition of 10% palladium carbon (58 mg) at room temperature. After purging with hydrogen, the reaction mixture was stirred for 19 hours at room temperature. After the reaction mixture was filtered through cellite, the solvent was concentrated under reduced pressure. The residue was purified by silica gel column chromatography (Kanto Kagaku, silica gel 60 (spherical, neutral), 40–100 μm, eluent: ethyl acetate/n-hexane=1/1) to give (4S,5R)-3,4-dimethyl-1-[(2R)-11-(17β-hydroxy-3-methoxyestra-1,3,5(10)-trien-7α-yl)-2-(3,3,4,4,5,5,6,6,6-nonafluorohexyl)undecanoyl]-5-phenylimidazolidin-2-one (579 mg, Yield 100%).

$^1$H-NMR(300 MHz, CDCl$_3$): δ 7.33–7.11 (m, 6H), 6.73–6.70 (m, 1H), 6.69–6.62 (m, 1H), 5.33 (d, J=7.8 Hz, 1H), 4.05–3.86 (m, 2H), 3.79–3.71 (m, 1H), 3.77 (s, 3H), 2.94–2.72 (m, 2H), 2.84 (s, 3H), 2.38–0.99 (m, 35H), 0.82 (d, J=5.9 Hz, 3H), 0.78 (s, 3H).

(Step 4)

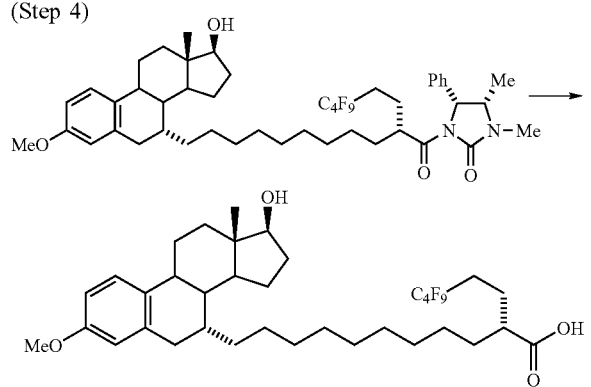

(4S,5R)-3,4-Dimethyl-1-[(2R)-11-(17β-hydroxy-3-methoxyestra-1,3,5(10)-trien-7α-yl)-2-(3,3,4,4,5,5,6,6,6-nonafluorohexyl)undecanoyl]-5-phenylimidazolidin-2-one (445 mg, 0.50 mmol) was dissolved in anhydrous ethylene glycol dimethyl ether (5 ml) under nitrogen atmosphere and then cooled to 0° C. To this solution, tetra-n-butylammonium hydroxide solution (40% w/w, 649 mg, 1.0 mmol) and aqueous hydrogen peroxide (30% w/w, 113 mg, 1.0 mmol) were added, and the resulting mixture was stirred for 1.5 hours at room temperature. The reaction mixture was quenched with saturated aqueous sodium thiosulfate, acidified with saturated aqueous potassium bisulfate, and then extracted with ethyl acetate. The organic layer was washed with saturated aqueous sodium chloride, dried over anhydrous magnesium sulfate, and then filtered. The filtrate was concentrated under reduced pressure using an evaporator and the resulting residue was purified by silica gel column chromatography (Wako gel C-200, eluent: ethyl acetate/n-hexane=4/6→8/2) to give (2R)-11-(17β-hydroxy-3-methoxyestra-1,3,5(10)-trien-7α-yl)-2-(3,3,4,4,5,5,6,6,6-nonafluorohexyl)undecanoic acid (360 mg, Yield 100%) and (4R,5S)-1,5-dimethyl-4-phenylimidazolidin-2-one (93 mg, Yield 98%).

$^1$H-NMR(300 MHz, CDCl$_3$): δ 7.21–7.18 (m, 1H), 6.73–6.69 (m, 1H), 6.62–6.61 (m, 1H), 6.30 (bs, 1H), 3.79–3.71 (m, 1H), 3.77 (s, 3H), 2.93–2.72 (m, 2H), 2.47–1.01 (m, 36H), 0.78 (s, 3H).

(Step 5)

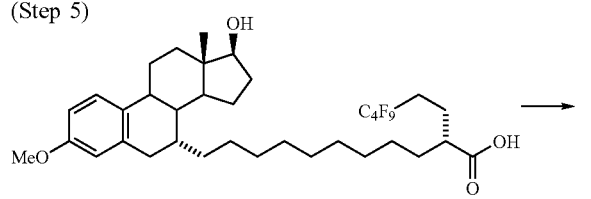

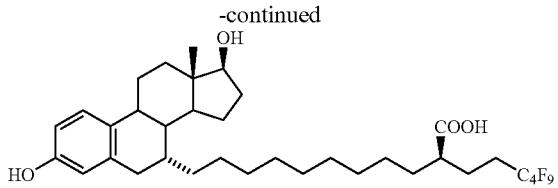

Anhydrous dichloromethane (10 ml) was added to (2R)-11-(17β-hydroxy-3-methoxyestra-1,3,5(10)-trien-7α-yl)-2-(3,3,4,4,5,5,6,6,6-nonafluorohexyl)undecanoic acid (358 mg, 0.50 mmol) under nitrogen atmosphere and the resulting mixture was cooled to −78° C. Boron tribromide (1.0 M in tetrahydrofuran, 3.0 ml, 3.0 mmol) was added dropwise to the mixture, which was then stirred on ice for 2.5 hours. The reaction mixture was cooled again to −78° C. and quenched with saturated aqueous sodium bicarbonate over 1 hour. After the reaction mixture was extracted with ethyl acetate, the organic layer was washed sequentially with saturated aqueous potassium bisulfate, saturated aqueous sodium chloride, saturated aqueous sodium bicarbonate and saturated aqueous sodium chloride, dried over anhydrous magnesium sulfate, and then filtered. The filtrate was concentrated under reduced pressure using an evaporator and the resulting residue was purified by silica gel column chromatography (Wako gel C-200, eluent: ethyl acetate/n-hexane=4/6) to give (2R)-11-(3,17β-dihydroxyestra-1,3,5(10)-trien-7α-yl)-2-(3,3,4,4,5,5,6,6,6-nonafluorohexyl)undecanoic acid (231 mg, Yield 60%) as a yellow amorphous mass.

Chemical purity: 99.05% and 98.63% at detection wavelengths of 280 and 219 nm, respectively, as measured by HPLC (column: YMC-Pack ODS-A, A-312 φ0.6×15 cm, solvent: H$_2$O/MeCN/TFA=30/70/0.1, flow rate: 1.0 ml/min)

Optical purity: 96.3% de, as measured by HPLC (column: Daicel Chiralpack AD, φ0.46×25 cm, solvent: n-hexane/isopropanol/TFA=90/10/0.1, flow rate: 0.5 ml/min, detection wavelength: 280 nm)

$^1$H-NMR(270 MHz, CDCl$_3$): δ 7.16–7.13 (m, 1H), 6.64–6.60 (m, 1H), 6.55–6.54 (m, 1H), 3.74 (t, J=8.6 Hz, 1H), 2.91–2.67 (m, 2H), 2.50–1.01 (m, 36H), 0.78 (s, 3H).

Example 37

Synthesis of (2R)-10-(3,17β-dihydroxyestra-1,3,5(10)-trien-7α-yl)-2-(4,4,5,5,6,6,7,7,7-nonafluoroheptyl)decanoic acid

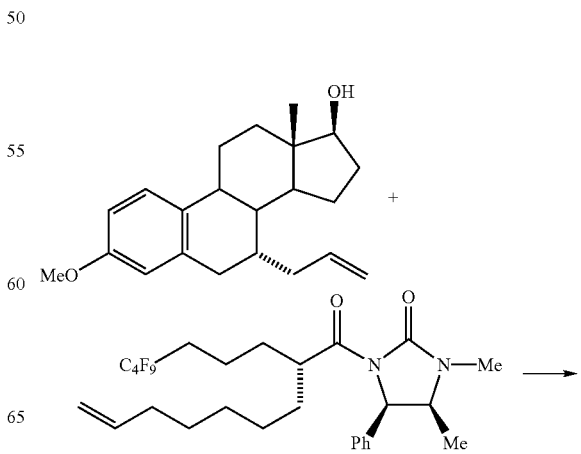

-continued

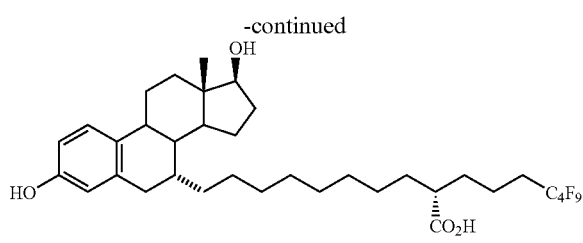

Starting with 3-methoxy-7α-(2-propenyl)estra-1,3,5(10)-trien-17β-ol and the (4S,5R)-3,4-dimethyl-1-[(2R)-2-(4,4,5,5,6,6,7,7,7-nonafluoroheptyl)-8-nonenoyl]-5-phenylimidazolidin-2-one prepared separately by a procedure analogous to Example 36, analogous procedure to Example 36 was repeated to give (2R)-10-(3,17β-dihydroxyestra-1,3,5(10)-trien-7α-yl)-2-(4,4,5,5,6,6,7,7,7-nonafluoroheptyl)decanoic acid.

$^1$H-NMR (300 MHz; CDCl$_3$): δ 7.12(d, J=8.4 Hz, 1H), 6.68(dd, J=8.5, 2.4 Hz, 1H), 6.53(d, J=2.6 Hz, 1H), 3.68(t, J=8.5 Hz, 1H), 2.95–2.60(m, 2H), 2.47–2.19(m, 4H), 2.18–1.03(m, 31H), 0.69(s, 3H).

Example 38

Synthesis of (2S)-10-(3,17β-dihydroxyestra-1,3,5(10)-trien-7α-yl)-2-(4,4,5,5,6,6,7,7,7-nonafluoroheptyl)decanoic acid

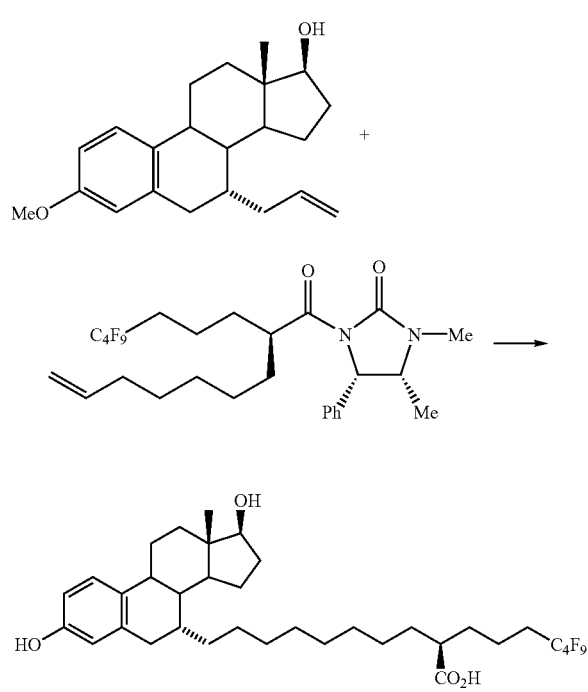

Stating with 3-methoxy-7α-(2-propenyl)estra-1,3,5(10)-trien-17β-ol and the (4R,5S)-3,4-dimethyl-1-[(2S)-2-(4,4,5,5,6,6,7,7,7-nonafluoroheptyl)-8-nonenoyl]-5-phenylimidazolidin-2-one prepared separately by a procedure analogous to Example 36, analogous procedure to Example 36 was repeated to give (2S)-10-(3,17β-dihydroxyestra-1,3,5(10)-trien-7α-yl)-2-(4,4,5,5,6,6,7,7,7-nonafluoroheptyl)decanoic acid.

$^1$H-NMR (300 MHz; CDCl$_3$): δ 7.12(d, J=8.4 Hz, 1H), 6.68(dd, J=8.5, 2.4 Hz, 1H), 6.53(d, J=2.6 Hz, 1H), 3.68(t, J=8.5 Hz, 1H), 2.95–2.60(m, 2H), 2.47–2.19(m, 4H), 2.18–1.03(m, 31H), 0.69(s, 3H).

Example 39

Synthesis of (2R)-11-[3,17β-dihydroxyestra-1,3,5 (10)-trien-11β-yl]-2-(3,3,4,4,5,5,6,6,6-nonafluorohexyl)undecanic acid (Step 1)

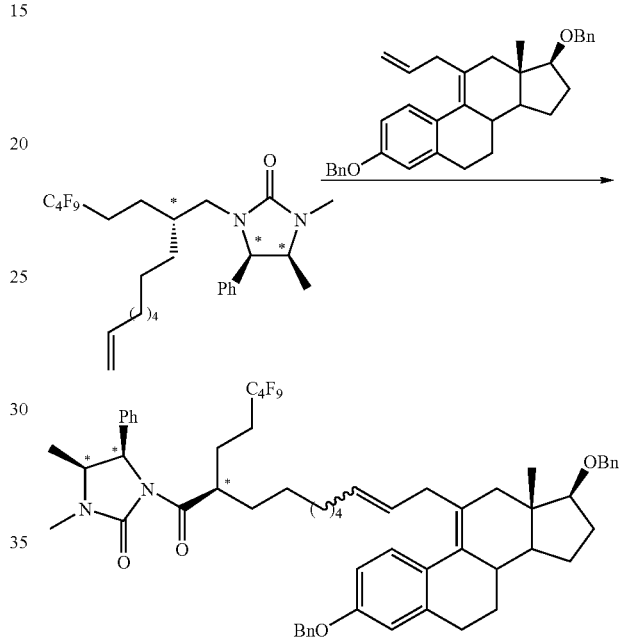

3,17β-Bis(benzyloxy)-11-(2-propenyl)estra-1,3,5(10),9 (11)-tetraene (491 mg, 1.00 mmol) and the (4S,5R)-3,4-dimethyl-1-[(2R)-2-(3,3,4,4,5,5,6,6,6-nonafluorohexyl)-9-decenoyl]-5-phenylimidazolidin-2-one (1.18 g, 2.00 mmol) prepared in Example 36 were dissolved in anhydrous dichloromethane (10 ml) at room temperature under nitrogen atmosphere, mixed with benzylidene-bis(tricyclohexylphosphine)-dichlororuthenium (41 mg, 0.05 mmol), and then heated under reflux followed by stirring for 6 hours under nitrogen atmosphere. After cooling, the reaction mixture was concentrated under reduced pressure and the resulting residue was purified by silica gel flash chromatography (eluent: ethyl acetate/n-hexane=3/7) to give a mixture of (4S,5R)-1-{(2R,9E)-11-[3,17β-bis(benzyloxy)estra-1,3,5(10),9(11)-tetraen-11-yl]-2-(3,3,4,4,5,5,6,6,6-nonafluorohexyl)-9-undecenoyl}-3,4-dimethyl-5-phenylimidazolidin-2-one and (4S,5R)-1-{(2R,9Z)-11-[3,17β-bis(benzyloxy)estra-1,3,5 (10),9(11)-tetraen-11-yl]-2-(3,3,4,4,5,5,6,6,6-nonafluorohexyl)-9-undecenoyl}-3,4-dimethyl-5-phenylimidazolidin-2-one (664 mg, Yield 63%).

$^1$H-NMR(270 MHz, CDCl$_3$): δ 7.45–7.10(m, 16H), 6.78–6.70(m, 2H), 5.58–5.40(m, 2H), 5.32(d, J=8.7 Hz, 1H), 5.04(s, 2H), 4.65–4.50(m, 2H), 4.10–3.80(m, 2H), 3.62–3.50(m, 1H), 3.22–3.05(m, 1H), 2.83(s, 3H), 2.80–2.60(m, 3H), 2.52–2.30(m, 1H), 2.20–1.0(m, 25H), 0.87(s, 3H, C18-CH$_3$), 0.81(d, J=6.6 Hz, 3H).

(Step 2)

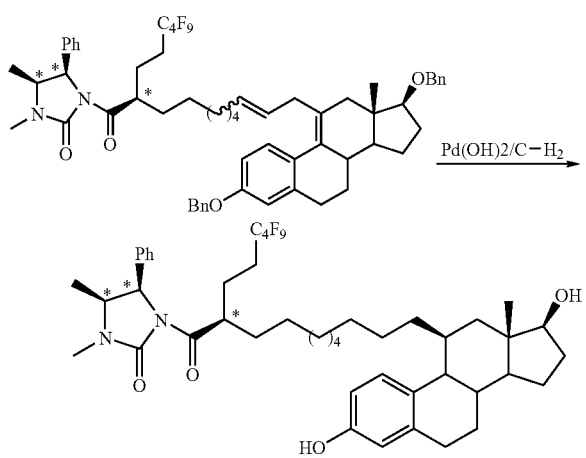

The mixture of (4S,5R)-1-{(2R,9E)-11-[3,17β-bis-(benzyloxy)estra-1,3,5(10),9(11)-tetraen-11-yl]-2-(3,3,4,4,5,5,6,6,6-nonafluorohexyl)-9-undecenoyl}-3,4-dimethyl-5-phenylimidazolidin-2-one and (4S,5R)-1-{(2R,9Z)-11-[3,17β-bis(benzyloxy)estra-1,3,5(10),9(11)-tetraen-11-yl]-2-(3,3,4,4,5,5,6,6,6-nonafluorohexyl)-9-undecenoyl}-3,4-dimethyl-5-phenylimidazolidin-2-one (283 mg, 0.27 mmol) was dissolved in a mixed solvent of methanol (12 ml) and tetrahydrofuran (1.2 ml), followed by addition of palladium hydroxide/carbon (85 mg) at room temperature. After purging with hydrogen, the reaction mixture was stirred for 1 day at room temperature. After the reaction mixture was filtered, the solvent was concentrated under reduced pressure. The residue was purified by silica gel column chromatography (eluent: ethyl acetate/n-hexane=3/7) to give (4S,5R)-1-{(2R)-11-[3,17β-dihydroxyestra-1,3,5(10)-trien-11β-yl]-2-(3,3,4,4,5,5,6,6,6-nonafluorohexyl)undecanoyl}-3,4-dimethyl-5-phenylimidazolidin-2-one (164 mg, Yield 70%).

$^1$H-NMR(300 MHz, CDCl$_3$): δ 7.36–7.12(m, 5H), 6.94–6.88(m, 1H), 6.56–6.52 (m, 1H), 6.44–6.36(m, 1H), 5.64(s, 1H), 5.35(d, J=8.7 Hz, 1H), 5.70–5.15(m, 3H), 4.38(s, 3H), 4.40–2.60(m, 36H), 2.43(s, 3H), 2.34(d, J=6.6 Hz, 3H).

(Step 3)

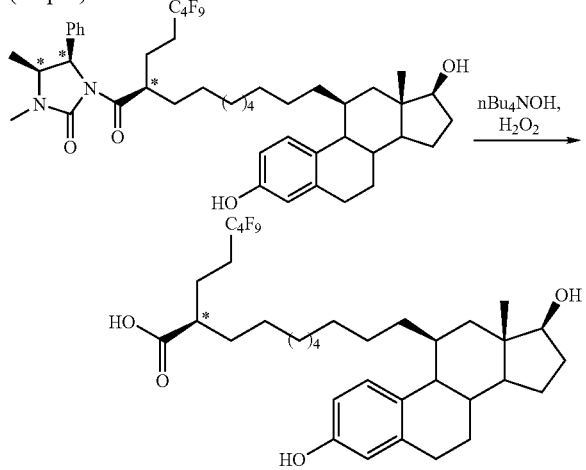

(4S,5R)-1-{(2R)-11-[3,17β-Dihydroxyestra-1,3,5(10)-trien-11β-yl]-2-(3,3,4,4,5,5,6,6,6-nonafluorohexyl)undecanoyl}-3,4-dimethyl-5-phenylimidazolidin-2-one (140 mg, 0.16 mmol) was dissolved in DME (3 ml). To this solution, tetra-n-butylammonium hydroxide solution (40% w/w, 312 mg, 0.48 mmol) and aqueous hydrogen peroxide (30% w/w, 56 mg, 0.48 mmol) were added, and the resulting mixture was stirred for 2 hours at room temperature. The reaction mixture was quenched with 10% aqueous sodium sulfite, acidified with 2N hydrochloric acid, and then extracted with ethyl acetate. The organic layer was washed with saturated aqueous sodium chloride, dried over anhydrous magnesium sulfate, and then filtered. The filtrate was concentrated under reduced pressure and the resulting residue was purified by silica gel column chromatography (Wako gel C-200, eluent: ethyl acetate/n-hexane=3/7), then by preparative HPLC (YMC-ODS-5-B (3×25 cm), eluent: acetonitrile/water/trifluoroacetic acid=90/10/0.1, flow rate: 18 mL/min), to give the desired compound (2R)-11-[3,17β-dihydroxyestra-1,3,5(10)-trien-11β-yl]-2-(3,3,4,4,5,5,6,6,6-nonafluorohexyl)undecanic acid (58 mg, Yield 52%).

$^1$H-NMR(300 MHz, CDCl$_3$): δ 7.00(d, J=8.4 Hz, 1H, C1-CH), 6.55(dd, J=8.4, 2.4 Hz, 1H, C2-CH), 6.54(d, J=2.4 Hz, 1H, C4-CH), 3.75(t, J=7.5 Hz, 1H), 2.85–1.10(m, 38H), 0.92(s, 3H, C18-CH3).

Chemical purity: 98.4%, as measured by HPLC (column: YMC-Pack ODS-A, A-312 φ0.6×15 cm, solvent: H$_2$O/MeCN/TFA=30/70/0.1, flow rate: 1.0 ml/min, detection wavelength: 220 nm)

Optical purity: 95.7%de, as measured by HPLC (column: Daicel Chiralpack AD, φ0.46×25 cm, solvent: n-hexane/i-propanol/TFA=92/8/0.08, flow rate: 0.5 ml/min, detection wavelength: 280 nm)

Test Example 1

Anti-estrogenic Activity (Oral Administration)

Test compounds were assayed for their oral anti-estrogenic activity in the following manner. In this experiment, the compounds prepared in Examples 5, 12, 14–33, 37 and 38 were used as test compounds. As control compounds, those having the same structures in the parent scaffold as the test compounds were used, that is, ZM189154 for Examples 5 and 27–33 and ICI182780 for Examples 12, 14–26, 37 and 38.

To determine anti-estrogenic activity, mice (ICR, weight 30±2 g) which had been ovariectomized 2 weeks before were subcutaneously administered with 17β-estradiol-benzoate (Sigma) in an amount of 0.1 μg/mouse for 3 days and the degree by which the test compound inhibited the increase in uterine weight was measured. In this experiment, each of the test and control compounds was suspended in 5% arabic gum solution and orally administered for 3 days on a once-a-day basis. After 24 hours from the last administration, the test animals were sacrificed and the uteri were removed and weighed. The results obtained are shown in Table 2 below.

TABLE 2

Anti-estrogenic activity in ovariectomized mice administered with 17β-estradiol (oral administration, 3 days)

| Test compound/dose (p.o., 3 days) | | |
|---|---|---|
| Compound | mg/kg | Inhibition (%) |
| Example 5 | 10 | 67 |
| Example 27 | 10 | 64 |
| Example 28 | 10 | 68 |
| Example 29 | 10 | 80 |

TABLE 2-continued

Anti-estrogenic activity in ovariectomized mice administered with 17β-estradiol (oral administration, 3 days)

Test compound/dose (p.o., 3 days)

| Compound | mg/kg | Inhibition (%) |
|---|---|---|
| Example 30 | 10 | 58 |
| Example 31 | 10 | 75 |
| Example 32 | 10 | 73 |
| Example 33 | 10 | 64 |
| ZM189154 | 10 | 42 |
| Example 12 | 10 | 97 |
| Example 14 | 10 | 87 |
| Example 15 | 10 | 96 |
| Example 16 | 10 | 98 |
| Example 17 | 10 | 94 |
| Example 18 | 10 | 85 |
| Example 19 | 10 | 92 |
| Example 20 | 10 | 94 |
| Example 21 | 10 | 99 |
| Example 22 | 10 | 98 |
| Example 23 | 10 | 98 |
| Example 24 | 10 | 98 |
| Example 25 | 10 | 93 |
| Example 26 | 10 | 96 |
| Example 37 | 10 | 101 |
| Example 38 | 10 | 100 |
| ICI182780 | 10 | 51 |

The results shown in Table 2 above indicate that the compounds having a side chain of general formula (1) according to the present invention show a superior inhibitory activity against the estradiol-induced increase in uterine weight, as compared to the anti-estrogenic control compounds ZM189154 and ICI182780 which have the same parent scaffold but no such side chain.

INDUSTRIAL APPLICABILITY

The compounds of the present invention have a side chain of general formula (1). This side chain allows the compounds of the present invention to show an improved bioavailability and a significantly increased activity following oral administration, as compared to the conventional compounds lacking that side chain, such as compounds having low activity following oral administration, compounds having anti-tumor activity, compounds having estrogenic activity or compounds having anti-estrogenic activity. The compounds of the present invention are therefore advantageous in pharmaceutical use.

What is claimed is:

1. A compound having the following formula (2):

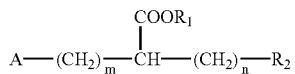
(2)

in which
$R_1$ represents a hydrogen atom or a salt-forming metal,
$R_2$ represents a linear or branched $C_1$–$C_7$ halogenoalkyl group,
m represents an integer of 2 to 14,
n represents an integer of 2 to 7, and
A represents a group selected from the following formulae (5) to (8), (10) to (16) and (21) to (24):

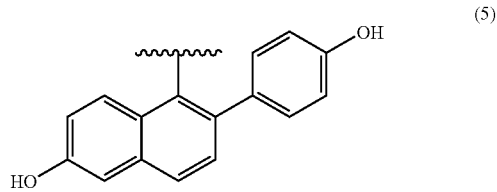
(5)

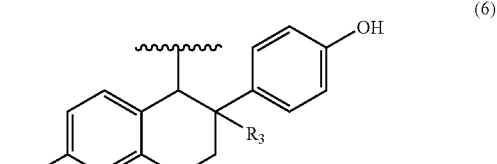
(6)

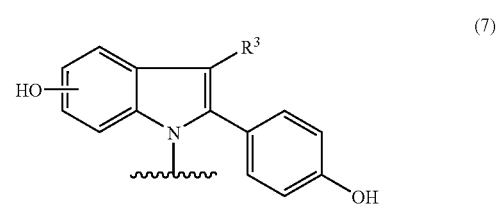
(7)

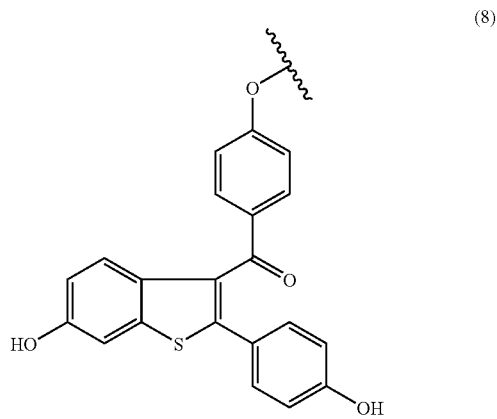
(8)

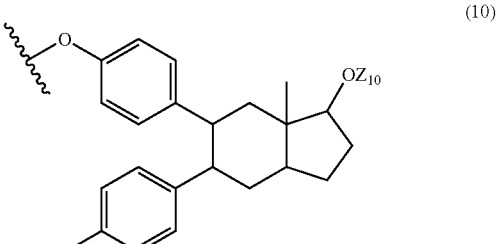
(10)

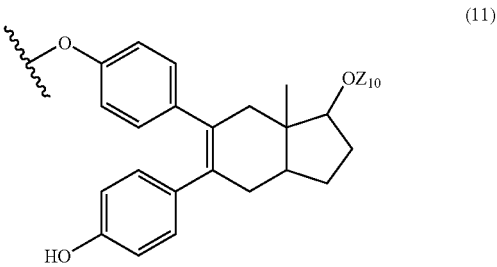
(11)

-continued

(12)
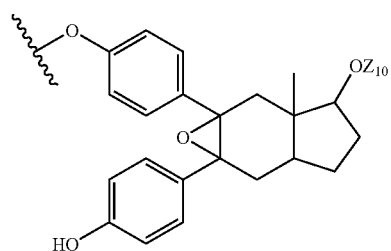

(13)
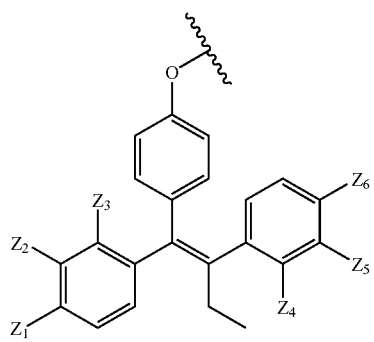

(14)
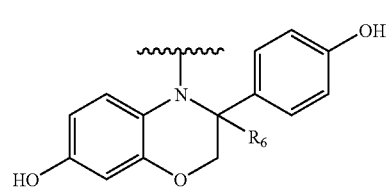

(15)
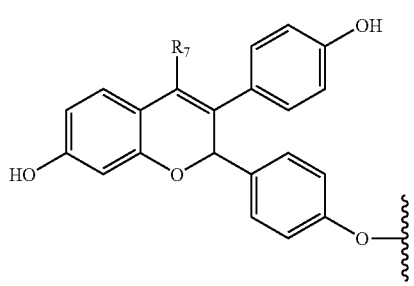

(16)
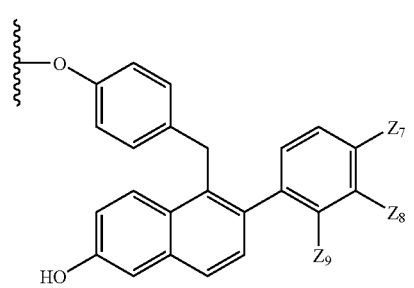

-continued

(21)
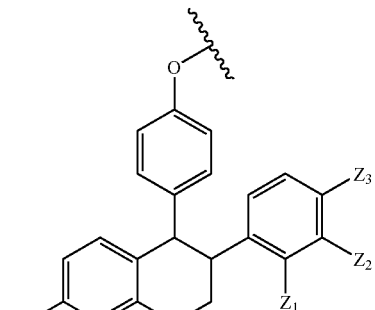

(22)
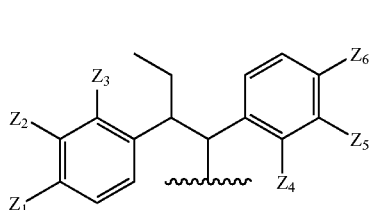

(23)
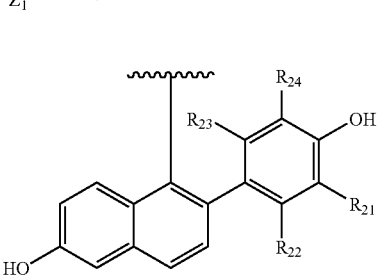

in which
in formulae (6), (7), and (14), each of $R_3$ and $R_6$ represents a linear or branched $C_1$–$C_5$ alkyl group,
in formulae (10), (11) and (12), $Z_{10}$ represents a hydrogen atom or an acyl group,
in formulae (13), (21) and (22), each of $Z_1$, $Z_2$, $Z_3$, $Z_4$, $Z_5$ and $Z_6$ independently represents a hydrogen atom, a hydroxyl group or a linear or branched $C_1$–$C_5$ alkyl group,
in formula (15), $R_7$ represents a hydrogen atom or a linear or branched $C_1$–$C_5$ alkyl group,
in formula (16), each of $Z_7$, $Z_8$ and $Z_9$ independently represents a hydrogen atom or a hydroxyl group,
in formula (23), each of $R_{21}$, $R_{22}$, $R_{23}$ and $R_{24}$ independently represents a hydrogen atom, a linear or branched $C_1$–$C_5$ alkyl group, a linear or branched $C_1$–$C_7$ halogenoalkyl group, a halogen atom or an acyl group, or an enantiomer of the compound, or a pharmaceutically acceptable salt of the compound or enantiomer thereof.

2. The compound or an enantiomer thereof, or a pharmaceutically acceptable salt of the compound or an enantiomer thereof according to claim 1, wherein $R_2$ is a linear or branched $C_1$–$C_5$ perhalogenoalkyl group or a group of the following general formula (9):

(9)
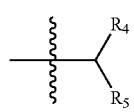

in which each of $R_4$ and $R_5$ which may be the same or different represents a linear or branched $C_1$–$C_3$ perhalogenoalkyl group.

3. The compound or an enantiomer thereof, or a pharmaceutically acceptable salt of the compound or an enantiomer thereof according to claim 2, wherein a halogen atom in the halogenoalkyl group is a fluorine atom.

4. An anti-estrogenic pharmaceutical composition comprising the compound according to claim 1 as an active ingredient.

5. The compound or an enantiomer thereof, or a pharmaceutically acceptable salt of the compound or an enantiomer thereof according to claim 1, wherein a halogen atom in the halogenoalkyl group is a fluorine atom.

6. The compound or an enantiomer thereof, or a pharmaceutically acceptable salt of the compound or an enantiomer thereof according to claim 2 wherein A is a group of formula (5), (6), (7), (8), (10), (11), (12), (13), (14), (15), (16), (21), (22) or (23), and m is an integer of 4 to 10.

7. The compound or an enantiomer thereof, or a pharmaceutically acceptable salt of the compound or an enantiomer thereof according to claim 1, wherein a carbon atom in formula (2), to which —COOR is attached, takes R- or S-configuration.

8. The compound or an enantiomer thereof, or a pharmaceutically acceptable salt of the compound or enantiomer thereof according to claim 2, wherein a carbon atom in formula (2), to which —COOR is attached, takes R- or S-configuration.

9. A pharmaceutical composition comprising the compound according to claim 1 as an active ingredient.

10. A pharmaceutical composition comprising the compound according to claim 2 as an active ingredient.

11. A pharmaceutical composition comprising the compound according to claim 3 as an active ingredient.

12. A method for treating breast cancer comprising administering to a patient in need thereof a compound according to claim 1.

13. A method for treating breast cancer comprising administering to a patient in need thereof a compound according to claim 2.

14. A method for treating breast cancer comprising administering to a patient in need thereof a compound according to claim 3.

* * * * *